United States Patent
Chang et al.

(10) Patent No.: US 10,022,438 B2
(45) Date of Patent: Jul. 17, 2018

(54) METHOD OF ENHANCING KSHV LANA1 IMMUNOGENICITY

(71) Applicant: University of Pittsburgh—Of the Commonwealth System of Higher Education, Pittsburgh, PA (US)

(72) Inventors: Yuan Chang, Pittsburgh, PA (US); Patrick S. Moore, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/179,124

(22) Filed: Jun. 10, 2016

(65) Prior Publication Data
US 2016/0331833 A1 Nov. 17, 2016

Related U.S. Application Data

(60) Division of application No. 13/334,657, filed on Dec. 22, 2011, now Pat. No. 9,402,895, which is a continuation-in-part of application No. 13/221,040, filed on Aug. 30, 2011, now abandoned, which is a continuation of application No. 12/191,698, filed on Aug. 14, 2008, now abandoned.

(60) Provisional application No. 60/955,898, filed on Aug. 15, 2007, provisional application No. 61/427,225, filed on Dec. 27, 2010.

(51) Int. Cl.
| | |
|---|---|
| A01N 63/00 | (2006.01) |
| A01N 65/00 | (2009.01) |
| A61K 48/00 | (2006.01) |
| A61K 39/245 | (2006.01) |
| C07K 14/005 | (2006.01) |
| A61K 39/12 | (2006.01) |
| C12N 7/00 | (2006.01) |
| A61K 39/00 | (2006.01) |

(52) U.S. Cl.
CPC ............ *A61K 39/245* (2013.01); *A61K 39/12* (2013.01); *C07K 14/005* (2013.01); *C12N 7/00* (2013.01); *A61K 2039/54* (2013.01); *A61K 2039/55505* (2013.01); *A61K 2039/585* (2013.01); *C07K 2319/60* (2013.01); *C12N 2710/16422* (2013.01); *C12N 2710/16434* (2013.01); *C12N 2710/16471* (2013.01)

(58) Field of Classification Search
None
See application file for complete search history.

(56) References Cited

U.S. PATENT DOCUMENTS

| | | |
|---|---|---|
| 9,402,895 B2 * | 8/2016 | Chang |
| 2002/0137020 A1 | 9/2002 | Chang et al. |
| 2003/0133948 A1 | 7/2003 | Robertson et al. |
| 2006/0233770 A1 | 10/2006 | Ambinder et al. |
| 2008/0213834 A1 | 9/2008 | Reed et al. |
| 2009/0022748 A1 | 1/2009 | Chang et al. |
| 2009/0068211 A1 | 3/2009 | Chang et al. |
| 2009/0203545 A1 | 8/2009 | Lindner et al. |
| 2011/0265195 A1 | 10/2011 | Chang et al. |
| 2011/0311567 A1 | 12/2011 | Chang et al. |

FOREIGN PATENT DOCUMENTS

WO 2007047759 A1 4/2007

OTHER PUBLICATIONS

Aboulafia DM. Kaposi sarcoma flares during effective antiretroviral treatment. AIDS Read. Apr. 2005;15(4):190-1.
Ballestas ME, Chatis PA, Kaye KM. Efficient persistence of extrachromosomal KSHV DNA mediated by latency-associated nuclear antigen. Science. Apr. 23, 1999;284(5414):641-4.
Basta S, Stoessel R, Basler M, van den Broek M, Groettrup M. Cross-presentation of the long-lived lymphocytic choriomeningitis virus nucleoprotein does not require neosynthesis and is enhanced via heat shock proteins. J Immunol. Jul. 15, 2005;175(2):796-805.
Brinster RL, Brunner S, Joseph X, Levey IL. Protein degradation in the mouse blastocyst. J Biol Chem. Mar. 25, 1979;254(6):1927-31.
Canham M, Talbot SJ. A naturally occurring C-terminal truncated isoform of the latent nuclear antigen of Kaposi's sarcoma-associated herpesvirus does not associate with viral episomal DNA. J Gen Virol. Jun. 2004;85(Pt 6):1363-9.
Chambers WH, Bozik ME, Brissette-Storkus SC, Basse P, Redgate E, Watkins S, Boggs SS. NKR-P1+ cells localize selectively in Rat 9L gliosarcomas but have reduced cytolytic function. Cancer Res. Aug. 1, 1996;56(15):3516-25.
Chang Y, Cesarman E, Pessin MS, Lee F, Culpepper J, Knowles DM, Moore PS. Identification of herpesvirus-like DNA sequences in AIDS-associated Kaposi's sarcoma. Science. Dec. 16, 1994;266(5192):1865-9.
Corte-Real S, Collins C, Aires da Silva F, Simas JP, Barbas CF 3rd, Chang Y, Moore P, Goncalves J. Intrabodies targeting the Kaposi sarcoma-associated herpesvirus latency antigen inhibit viral persistence in lymphoma cells. Blood. Dec. 1, 2005;106(12):3797-802. Epub Aug. 9, 2005.
Coscoy L, Ganem D. PHD domains and E3 ubiquitin ligases: viruses make the connection. Trends Cell Biol. Jan. 2003;13(1):7-12.
Dantuma NP, Heessen S, Lindsten K, Jellne M, Masucci MG. Inhibition of proteasomal degradation by the gly-Ala repeat of Epstein-Barr virus is influenced by the length of the repeat and the strength of the degradation signal. Proc Natl Acad Sci U S A. Jul. 18, 2000;97(15):8381-5.
Dantuma NP, Lindsten K, Glas R, Jellne M, Masucci MG. Short-lived green fluorescent proteins for quantifying ubiquitin/proteasome-dependent proteolysis in living cells. Nat Biotechnol. May 2000;18(5):538-43.
Davenport MG, Pagano JS. Expression of EBNA-1 mRNA is regulated by cell cycle during Epstein-Barr virus type I latency. J Virol. Apr. 1999;73(4):3154-61.
Dittmer D, Lagunoff M, Renne R, Staskus K, Haase A, Ganem D. A cluster of latently expressed genes in Kaposi's sarcoma-associated herpesvirus. J Virol. Oct. 1998;72(10):8309-15.

(Continued)

*Primary Examiner* — Nora Rooney
(74) *Attorney, Agent, or Firm* — The Webb Law Firm

(57) ABSTRACT

An immunogenically-enhanced Kaposi sarcoma-associated herpesvirus latency-associated nuclear antigen 1 ("KSHV LANA1") polypeptide and related methods of eliciting an immune response to KSHV LANA1 are provided. Also described herein is a novel polypeptide capable of inhibiting degradation of a protein or retarding synthesis of a protein when attached to or incorporated within that protein.

14 Claims, 26 Drawing Sheets

(56) References Cited

OTHER PUBLICATIONS

Figures 2B, 3:
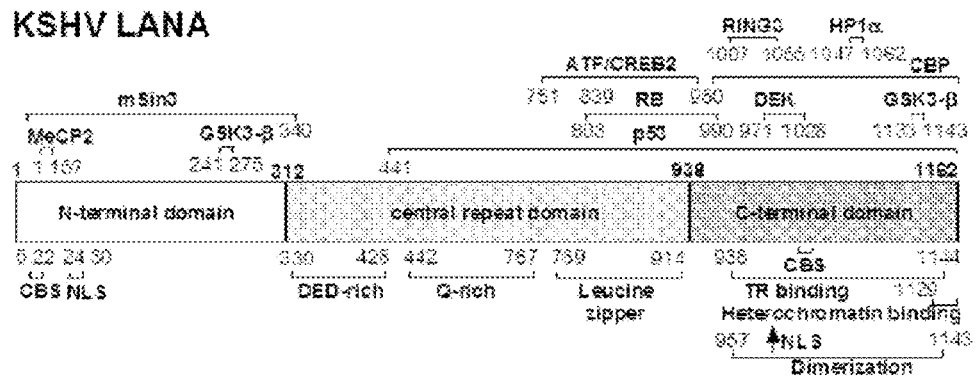

Friborg J Jr, Kong W, Hottiger MO, Nabel GJ. p53 inhibition by the LANA protein of KSHV protects against cell death. Nature. Dec. 23-30, 1999;402(6764):889-94.

Fujimuro M, Hayward SD. The latency-associated nuclear antigen of Kaposi's sarcoma-associated herpesvirus manipulates the activity of glycogen synthase kinase-3beta. J Virol. Jul. 2003;77(14):8019-30.

Fung TK, Siu WY, Yam CH, Lau A, Poon RY. Cyclin F is degraded during G2-M by mechanisms fundamentally different from other cyclins. J Biol Chem. Sep. 20, 2002;277(38):35140-9. Epub Jul. 16, 2002.

Gao SJ, Zhang YJ, Deng JH, Rabkin CS, Flore O, Jenson HB.Molecular polymorphism of Kaposi's sarcoma-associated herpesvirus (Human herpesvirus 8) latent nuclear antigen: evidence for a large repertoire of viral genotypes and dual infection with different viral genotypes. J Infect Dis. Nov. 1999;180(5)1466-76.

Gao SJ, Kingsley L, Hoover DR, Spira TJ, Rinaldo CR, Saah A, Phair J, Detels R, Parry P, Chang Y, Moore PS. Seroconversion to antibodies against Kaposi's sarcoma-associated herpesvirus-related latent nuclear antigens before the development of Kaposi's sarcoma. N Engl J Med. Jul. 25, 1996;335(4):233-41.

Gao SJ, Kingsley L, Li M, Zheng W, Parravicini C, Ziegler J, Newton R, Rinaldo CR, Saah A, Phair J, Detels R, Chang Y, Moore PS. KSHV antibodies among Americans, Italians and Ugandans with and without Kaposi's sarcoma. Nat Med. Aug. 1996;2(8):925-8.

Gaiter AC, Shu MA, Hu J, Renne R. DNA binding and modulation of gene expression by the latency-associated nuclear antigen of Kaposi's sarcoma-associated herpesvirus. J Virol. Sep. 2001;75(17):7882-92.

Giezeman-Smits KM, Okada H, Brissette-Storkus CS, Villa LA, Attanucci J, Lotze MT, Pollack IF, Bozik ME, Chambers WH. Cytokine gene therapy of gliomas: induction of reactive CD4+ T cells by interleukin-4-transfected 9L gliosarcoma is essential for protective immunity. Cancer Res. May 1, 2000;60(9):2449-57.

Gill J, Bourboulia D, Wilkinson J, Hayes P, Cope A, Marcelin AG, Calvez V, Gotch F, Boshoff C, Gazzard B. Prospective study of the effects of antiretroviral therapy on Kaposi sarcoma—associated herpesvirus infection in patients with and without Kaposi sarcoma. J Acquir Immune Defic Syndr. Dec. 1, 2002;31(4):384-90.

Godfrey A, Anderson J, Papanastasiou A, Takeuchi Y, Boshoff C. Inhibiting primary effusion lymphoma by lentiviral vectors encoding short hairpin RNA. Blood. Mar. 15, 2005;105(6):2510-8. Epub Nov. 30, 2004.

Grossman SR, Deato ME, Brignone C, Chan HM, Kung AL, Tagami H, Nakatani Y, Livingston DM. Polyubiquitination of p53 by a ubiquitin ligase activity of p300. Science. Apr. 11, 2003;300(5617):342-4.

Heessen S, Masucci MG, Dantuma NP. The UBA2 domain functions as an intrinsic stabilization signal that protects Rad23 from proteasomal degradation. Mol Cell. Apr. 15, 2005;18(2):225-35.

Herrera JL, Fernández-Montesinos R, González-Rey E, Delgado M, Pozo D. Protective role for plasmid DNA-mediated VIP gene transfer in non-obese diabetic mice. Ann N Y Acad Sci. Jul. 2006;1070:337-41.

Hu J, Garber AC, Renne R. The latency-associated nuclear antigen of Kaposi's sarcoma-associated herpesvirus supports latent DNA replication in dividing cells. J Virol. Nov. 2002;76(22):11677-87.

Kaspar M, Dienemann A, Schulze C, Sprenger F. Mitotic degradation of cyclin A is mediated by multiple and novel destruction signals. Curr Biol. May 1, 2001;11(9):685-90.

Kedes DH, Operskalski E, Busch M, Kohn R, Flood J, Ganem D. The seroepidemiology of human herpesvirus 8 (Kaposi's sarcoma-associated herpesvirus): distribution of infection in KS risk groups and evidence for sexual transmission. Nat Med. Aug. 1996;2(8):918-24.

Kedes DH, Lagunoff M, Renne R, Ganem D. Identification of the gene encoding the major latency-associated nuclear antigen of the Kaposi's sarcoma-associated herpesvirus. J Clin Invest. Nov. 15, 1997;100(10):2606-10.

Kellam P, Bourboulia D, Dupin N, Shotton C, Fisher C, Talbot S, Boshoff C, Weiss RA. Characterization of monoclonal antibodies raised against the latent nuclear antigen of human herpesvirus 8. J Virol. Jun. 1999;73(6):5149-55.

Kellam P, Boshoff C, Whitby D, Matthews S, Weiss RA, Talbot SJ. Identification of a major latent nuclear antigen, LNA-1, in the human herpesvirus 8 genome. J Hum Virol. Nov.-Dec. 1997;1(1):19-29.

Komatsu T, Ballestas ME, Barbera AJ, Kaye KM. The KSHV latency-associated nuclear antigen: a multifunctional protein. Front Biosci. Mar. 1, 2002;7:d726-30.

Lee SP, Brooks JM, Al-Jarrah H, Thomas WA, Haigh TA, Taylor GS, Humme S, Schepers A, Hammerschmidt W, Yates JL, Rickinson AB, Blake NW.CD8 T cell recognition of endogenously expressed epstein-barr virus nuclear antigen 1. J Exp Med. May 17, 2004;199(10):1409-20.

Levitskaya J, Coram M, Levitsky V, Imreh S, Steigerwald-Mullen PM, Klein G, Kurilla MG, Masucci MG.Inhibition of antigen processing by the internal repeat region of the Epstein-Barr virus nuclear antigen-1. Nature. Jun. 22, 1995;375(6533):685-8.

Levitskaya J, Sharipo A, Leonchiks A, Ciechanover A, Masucci MG. Inhibition of ubiquitin/proteasome-dependent protein degradation by the Gly-Ala repeat domain of the Epstein-Barr virus nuclear antigen 1. Proc Natl Acad Sci U S A. Nov. 11, 1997;94(23):12616-21.

Lieberman PM, Hu J, Renne R. Maintenance and Replication During Latency. 2006. In A. Arvin, A. Mocarski, P.S. Moore, B. Roizman, and R.J. Whitley (ed.), Human Herpesviruses: Biology, Therapy and Immunoprophylaxis, pp. 379-402, 2007. Cambridge University Press.

Lindow M, Nansen A, Bartholdy C, Stryhn A, Hansen NJ, Boesen TP, Wells TN, Schwartz TW, Thomsen AR. The virus-encoded chemokine vMIP-II inhibits virus-induced Tc1-driven inflammation. J Virol. Jul. 2003;77(13):7393-400.

Liu WJ, Gao F, Zhao KN, Zhao W, Fernando GJ, Thomas R, Frazer IH. Codon modified human papillomavirus type 16 E7 DNA vaccine enhances cytotoxic T-lymphocyte induction and anti-tumour activity. Virology. Sep. 15, 2002;301(1):43-52.

Lorenzo ME, Ploegh HL, Tirabassi RS. Viral immune evasion strategies and the underlying cell biology. Semin Immunol. Feb. 2001;13(1):1-9.

Miller L, Alber G, Varin-Blank N, Ludowyke R, Metzger H. Transmembrane signaling in P815 mastocytoma cells by transfected IgE receptors. J Biol Chem. Jul. 25, 1990;265(21):12444-53.

Miseki T, Kawakami H, Natsuizaka M, Darmanin S, Cui HY, Chen J, Fu Q, Okada F, Shindo M, Higashino F, Asaka M, Hamuro J, Kobayashi M. Suppression of tumor growth by intra-muscular transfer of naked DNA encoding adrenomedullin antagonist. Cancer Gene Ther. Jan. 2007;14(1):39-44. Epub Jul. 14, 2006.

Moore MW, Carbone FR, Bevan MJ. Introduction of soluble protein into the class I pathway of antigen processing and presentation. Cell. Sep. 9, 1988;54(6):777-85.

Moore PS, Chang Y. Kaposi's sarcoma-associated herpesvirus. 2001. In D. Knipe, P. Howley, D. Griffin, R. Lamb, M. Martin, and S. Straus (ed.). Fields Virology, p. 2803-2833. Fourth ed., vol. 2. Lippincott, Williams & Wilkins.

Moore PS, Gao SJ, Dominguez G, Cesarman E, Lungu O, Knowles DM, Garber R, Pellett PE, McGeoch DJ, Chang Y. Primary characterization of a herpesvirus agent associated with Kaposi's sarcomae. J Virol. Jan. 1996;70(1):549-58.

Mortellaro A, Hernandez RJ, Guerrini MM, Carlucci F, Tabucchi A, Ponzoni M, Sanvito F, Doglioni C, Di Serio C, Biasco L, Follenzi A, Naldini L, Bordignon C, Roncarolo MG, Aiuti A . . . Ex vivo gene therapy with lentiviral vectors rescues adenosine deaminase (ADA)-deficient mice and corrects their immune and metabolic defects. Blood. Nov. 1, 2006;108(9):2979-88. Epub Jul. 11, 2006.

Nguyen HG, Chinnappan D, Urano T, Ravid K. Mechanism of Aurora-B degradation and its dependency on intact KEN and

(56) References Cited

OTHER PUBLICATIONS

A-boxes: identification of an aneuploidy-promoting property. Mol Cell Biol. Jun. 2005;25(12):4977-92.

Okada H, Tsugawa T, Sato H, Kuwashima N, Gambotto A, Okada K, Dusak JE, Fellows-Mayle WK, Papworth GD, Watkins SC, Chambers WH, Potter DM, Storkus WJ, Pollack IF. Delivery of interferon-alpha transfected dendritic cells into central nervous system tumors enhances the antitumor efficacy of peripheral peptide-based vaccines. Cancer Res. Aug. 15, 2004;64(16):5830-8.

Okada H, Attanucci J, Giezeman-Smits KM, Brissette-Storkus C, Fellows WK, Gambotto A, Pollack LF, Pogue-Geile K, Lotze MT, Bozik ME, Chambers WH. Immunization with an antigen identified by cytokine tumor vaccine-assisted SEREX (CAS) suppressed growth of the rat 9L glioma in vivo. Cancer Res. Mar. 15, 2001;61(6):2625-31.

Osman M, Kubo T, Gill J, Neipel F, Becker M, Smith G, Weiss R, Gazzard B, Boshoff C, Gotch F. Identification of human herpesvirus 8-specific cytotoxic T-cell responses. J Virol. Jul. 1999;73(7):6136-40.

Pamer E, Cresswell P. Mechanisms of MHC class I—restricted antigen processing. Annu Rev Immunol. 1998;16:323-58.

Patel GV, Masucci MG, Winberg G, Klein G. Expression of the Epstein-Barr virus encoded EBNA-1 gene in stably transfected human and murine cell lines. Int J Cancer. Oct. 15, 1988;42(4):592-8.

Pfleger CM, Kirschner MW. The KEN box: an APC recognition signal distinct from the D box targeted by Cdh1. Genes Dev. Mar. 15, 2000;14(6):655-65.

Ponder KP. Gene therapy for hemophilia. Curr Opin Hematol. Sep. 2006;13(5):301-7.

Prell RA, Kerkvliet NI. Involvement of altered B7 expression in dioxin immunotoxicity: B7 transfection restores the CTL but not the autoantibody response to the P815 mastocytoma. J Immunol. Mar. 15, 1997;158(6):2695-703.

Qian SB, Bennink JR, Yewdell JW. Quantitating defective ribosome products. Methods Mol Biol. 2005;301:271-81.

Radkov SA, Kellam P, Boshoff C. The latent nuclear antigen of Kaposi sarcoma-associated herpesvirus targets the retinoblastoma-E2F pathway and with the oncogene Hras transforms primary rat cells. Nat Med. Oct. 2000;6(10):1121-7.

Rainbow L, Platt GM, Simpson GR, Sarid R, Gao SJ, Stoiber H, Herrington CS, Moore PS, Schulz TF.The 222- to 234-kilodalton latent nuclear protein (LNA) of Kaposi's sarcoma-associated herpesvirus (human herpesvirus 8) is encoded by orf73 and is a component of the latency-associated nuclear antigen. J Virol. Aug. 1997;71(8):5915-21.

Renwick N, Weverling GJ, Schulz T, Goudsmit J. Timing of human immunodeficiency virus type 1 and human herpesvirus 8 infections and length of the Kaposi's sarcoma-free period in coinfected persons. J Infect Dis. May 1, 2001;183(9)1427.

Rock KL, Goldberg AL. Degradation of cell proteins and the generation of MHC class I-presented peptides. Annu Rev Immunol. 1999;17:739-79.

Sand R, Wiezorek JS, Moore PS, Chang Y. Characterization and cell cycle regulation of the major Kaposi's sarcoma-associated herpesvirus (human herpesvirus 8) latent genes and their promoter. J Virol. Feb. 1999;73(2):1438-46.

Sarid R, Olsen SJ, Moore PS. Kaposi's sarcoma-associated herpesvirus: epidemiology, virology, and molecular biology. Adv Virus Res. 1999;52:139-232.

Schubert U, Antón LC, Gibbs J, Norbury CC, Yewdell JW, Bennink JR. Rapid degradation of a large fraction of newly synthesized proteins by proteasomes. Nature. Apr. 13, 2000;404(6779):770-4.

Schulz TF, Sheldon J, Greensill J. Kaposi's sarcoma associated herpesvirus (KSHV) or human herpesvirus 8 (HHV8). Virus Res. Jan. 30, 2002;82(1-2):115-26.

Seyfang A, Jin JH. Multiple site-directed mutagenesis of more than 10 sites simultaneously and in a single round. Anal Biochem. Jan. 15, 2004;324(2):285-91.

Sharipo A, Imreh M, Leonchiks A, Imreh S, Masucci MG. A minimal glycine-alanine repeat prevents the interaction of ubiquitinated I kappaB alpha with the proteasome: a new mechanism for selective inhibition of proteolysis. Nat Med. Aug. 1998;4(8):939-44.

Sharipo A, Imreh M, Leonchiks A, Brändén C, Masucci MG. cis-Inhibition of proteasomal degradation by viral repeats: impact of length and amino acid composition. FEBS Lett. Jun. 15, 2001;499(1-2):137-42.

Shelburne CP, Huff TF. Inhibition of kit expression in P815 mouse mastocytoma cells by a hammerhead ribozyme. Clin Immunol. Oct. 1999;93(1):46-58.

Sitas F, Carrara H, Beral V, Newton R, Reeves G, Bull D, Jentsch U, Pacella-Norman R, Bourboulia D, Whitby D, Boshoff C, Weiss R. Antibodies against human herpesvirus 8 in black South African patients with cancer. N Engl J Med. Jun. 17, 1999;340(24):1863-71.

Srinivasan V, Komatsu T, Ballestas ME, Kaye KM. Definition of sequence requirements for latency-associated nuclear antigen 1 binding to Kaposi's sarcoma-associated herpesvirus DNA. J Virol. Dec. 2004;78(24):14033-8.

Standifer, N. E. Panagiotopoulos, C. Tan, R. Current approaches for the prediction and identification of CD8 T-cell epitopes in type 1 diabetes. Curr Opin Endocrinol Diabetes, 2005; 12(4):298-302.

Szekely L, Kiss C, Mattsson K, Kashuba E, Pokrovskaja K, Juhasz A, Holmvall P, Klein G. Human herpesvirus-8-encoded LNA-1 accumulates in heterochromatin-associated nuclear bodies. J Gen Virol. Nov. 1999;80 ( Pt 11)2889-900.

Taylor JL, Bennett HN, Snyder BA, Moore PS, Chang Y. Transcriptional analysis of latent and inducible Kaposi's sarcoma-associated herpesvirus transcripts in the K4 to K7 region. J Virol. Dec. 2005;79(24):15099-106.

Tellam J, Connolly G, Green KJ, Miles JJ, Moss DJ, Burrows SR, Khanna R. Endogenous presentation of CD8+ T cell epitopes from Epstein-Barr virus-encoded nuclear antigen 1. J Exp Med. May 17, 2004;199(10):1421-31.

Tomescu C, Law WK, Kedes DH. Surface downregulation of major histocompatibility complex class I, PE-CAM, and ICAM-1 following de novo infection of endothelial cells with Kaposi's sarcoma-associated herpesvirus. J Virol. Sep. 2003;77(17):9669-84.

Varshaysky A. The N-end rule: functions, mysteries, uses. Proc Natl Acad Sci U S A. Oct. 29, 1996;93(22):12142-9.

Verma SC, Borah S, Robertson ES.Latency-associated nuclear antigen of Kaposi's sarcoma-associated herpesvirus up-regulates transcription of human telomerase reverse transcriptase promoter through interaction with transcription factor Sp1. J Virol. Oct. 2004;78(19):10348-59.

Wang QJ, Huang XL, Rappocciolo G, Jenkins FJ, Hildebrand WH, Fan Z, Thomas EK, Rinaldo CR Jr. Identification of an HLA A*0201-restricted CD8(+) T-cell epitope for the glycoprotein B homolog of human herpesvirus 8. Blood. May 1, 2002;99(9):3360-6.

Wang QJ, Jenkins FJ, Jacobson LP, Kingsley LA, Day RD, Zhang ZW, Meng YX, Pellett PE, Kousoulas KG, Baghian A, Rinaldo CR Jr. Primary human herpesvirus 8 infection generates a broadly specific CD8(+) T-cell response to viral lytic cycle proteins. Blood. Apr. 15, 2001;97(8):2366-73.

Wang QJ, Jenkins FJ, Jacobson LP, Meng YX, Pellett PE, Kingsley LA, Kousoulas KG, Baghian A, Rinaldo CR Jr. CD8+ cytotoxic T lymphocyte responses to lytic proteins of human herpes virus 8 in human immunodeficiency virus type 1-infected and -uninfected individuals. J Infect Dis. Sep. 2000;182(3):928-32. Epub Aug. 17, 2000.

Wilkinson J, Cope A, Gill J, Bourboulia D, Hayes P, Imami N, Kubo T, Marcelin A, Calvez V, Weiss R, Gazzard B, Boshoff C, Gotch F. Identification of Kaposi's sarcoma-associated herpesvirus (KSHV)-specific cytotoxic T-lymphocyte epitopes and evaluation of reconstitution of KSHV-specific responses in human immunodeficiency virus type 1-Infected patients receiving highly active antiretroviral therapy. J Virol. Mar. 2002;76(6):2634-40.

Wu S, Kumar KU, Kaufman RJ. Identification and requirement of three ribosome binding domains in dsRNA-dependent protein kinase (PKR). Biochemistry. Sep. 29, 1998;37(39):13816-26.

(56) References Cited

OTHER PUBLICATIONS

Yamano H, Tsurumi C, Gannon J, Hunt T. The role of the destruction box and its neighbouring lysine residues in cyclin B for anaphase ubiquitin-dependent proteolysis in fission yeast: defining the D-box receptor. EMBO J. Oct. 1, 1998;17(19):5670-8.

Yang T, Witham TF, Villa L, Erff M, Attanucci J, Watkins S, Kondziolka D, Okada H, Pollack IF, Chambers WH. Glioma-associated hyaluronan induces apoptosis in dendritic cells via inducible nitric oxide synthase: implications for the use of dendritic cells for therapy of gliomas. Cancer Res. May 1, 2002;62(9):2583-91.

Yewdell JW, Antón LC, Bennink JR. Defective ribosomal products (DRiPs): a major source of antigenic peptides for MHC class I molecules? J Immunol. Sep. 1, 1996;157(5):1823-6.

Yin Y, Manoury B, Fåhraeus R. Self-inhibition of synthesis and antigen presentation by Epstein-Barr virus-encoded EBNA1. Science. Sep. 5, 2003;301(5638):1371-4.

Zaldumbide A, Ossevoort M, Wiertz EJ, Hoeben RC. In cis inhibition of antigen processing by the latency-associated nuclear antigen I of Kaposi sarcoma herpes virus. Mol Immunol. Feb. 2007;44(6):1352-60. Epub Jul. 7, 2006.

Zhang YJ, Deng JH, Rabkin C, Gao SJ. Hot-spot variations of Kaposi's sarcoma-associated herpesvirus latent nuclear antigen and application in genotyping by PCR-RFLP. J Gen Virol. Aug. 2000;81(Pt 8):2049-58.

Zhao KN, Liu WJ, Frazer IH. Codon usage bias and A+T content variation in human papillomavirus genomes. Virus Res. Dec. 2003;98(2):95-104.

Ilyinskii et al., 2008, Vaccine, vol. 26; 2177-2185.

Amigorena et al., Cur. Opin. Immunol., 2010, vol. 22: 109-117.

Rock, Immunity, 2005, vol. 25: 523-525.

Janeway and Travers, 1997, Immunobiology, p. 4:15.

Persson et al., "Multiple mRNA species for the precursor to an adenovirus-encoded glycoprotein: Identification and structure of the signal sequence", Proc. Natl. Acad. Sci., Nov. 1980, pp. 6349-6353, vol. 77, No. 11.

Kwun et al, "Kaposi's Sarcoma-Associated Herpesvirus Latency-Associated Nuclear Antigen 1 Mimics Epstein-Barr Virus EBNA1 Immune Evasion through Central Repeat Domain Effects on Protein Processing", Journal of Virology, Aug. 2007, pp. 8225-8235, vol. 81, No. 15.

Tscharke et al., "Identification of poxvirus CD8+T cell determinants to enable rational design and characterization of smallpox vaccines", JEM, Jan. 3, 2005, pp. 95-104, vol. 201, No. 1.

English et al., "Autophagy enhances the presentation of endogenous viral antigens on MHC class I molecules during HSV-1 infection", Nature Immunology, May 2009, pp. 480-487, vol. 10, No. 5.

Coscoy, "Immune evasion by Kaposi's sarcoma-associated herpesvirus", Immunology, May 2007, pp. 391-401, vol. 7.

Glenn et al., "Identification of a spliced gene from Kaposi's Sarcoma-Associated Herpesvirus encoding a protein with similarities to latent membrane proteins 1 and 2A of Epstein-Barr Virus", J. Virol. 1999, pp. 6953-6963, vol. 73, No. 8.

\* cited by examiner

```
   1 mapqgmrlrs qrstgapltr qscrkrnrsp ercdlgddlh lqprrkhvad sidgrecgph
  61 tlpipgsptv ftsglpafvs sptlpvapip spapatplpp pallppvtts sspippshpv
 121 spgttdthsp spalpptqsp essqrpplss ptqrpdsstp mrpppsqqtt pphspttppp
 181 eppskaspds lapstlrslr krrlsspqgp stlnplcqsp pvspprcdfs nrsvyppwat
 241 espiyvqsss dqdtpprqpp tspislqsss psegswqddt amlvilasis essacknskec
 301 sennqagedn gdneiskesq vdkddsdnkd deesqetdes deeddeedde addeeddeed
 361 deeddeedde eddeeddeed deeddeeede eedeeedeee edeedddded nedeeddeee
 421 dkkedeedgg dgnktlsiqs sqqqqepqqq epqqqepqqq eplqepqqqe pqqqepqqqe
 481 plqepqgqep qqqeplqepq qqepqqqepq qqepqqqepq qqepqqqepq qqepqqqepq
 541 qqepqqqepq qrepqqrepq qrepqqrepq qrepqqrepq qrepqqrepq qrepqqqdeq
 601 qqdeqqqdeq qqdeqqqdeq qqdeqqqdeq qqdeqqqdeq qqdeqqqdeq qqdeqqqdeq
 661 qqdeqqqdeq qqdeqqqdeq qqdeqqqdeq qqdeqqqdeq eqqdeqeqqd eqeqqdeqqq
 721 deqqqqdeqq qqdeqqqqde qqqqdeqqqq deqeqqseqe qqeeqeqels eqsqeledqs
 781 qeleeqsqel eeqeqeleeq eqeleeqeqs leeqeqelee qeqeleeqeq sleeqeqels
 841 eqeveeqeqe veeqeqeqse qeleevseqe qeqeeqseqe leevseqeeq eleeveeqee
 901 qeleevseqe qqeleevseq eqqqveqqeq etveepillh qsssedemev dypvvstheq
 961 lassppqdnt pdddpqpqps rsyryvlrts pphrpgvrmr rvpvthpkkp hpryqqppvp
1021 yrgiddcpak arpqhlfyrr flgkdgrrdp kcqwkfavif wqndpyglkk lsqafqfggv
1081 kagpvsclph pgpdqspity cvyvycqnkd tskkvqmsrl aweashplag nlqssivkfk
1141 kplpltqpge nqgpqdspqe mt
```

Figures 1, 8A:
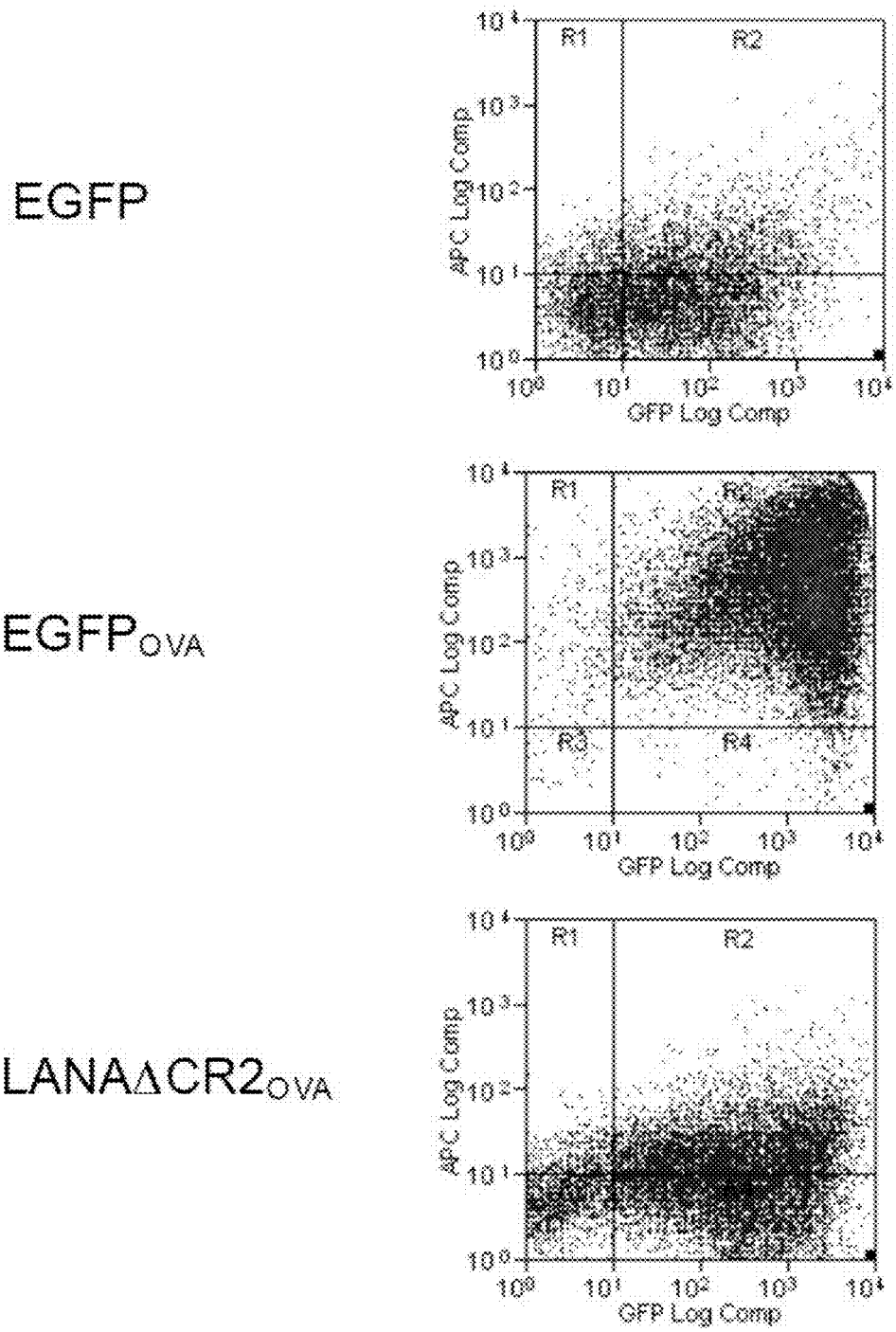

*Fig. 1*

```
   1 atggcgcccc cgggaatgcg cctgaggtcg ggaggagca ccggcgcgcc cttaacgaga
  61 ggaagttgta ggaaacgaaa caggtctccg gaaagatgtg accttggcga tgacctacat
 121 ctacaaccgc gaaggaagca tgtcgccgac tccatgacg gccggaatg tggaccccac
 181 accttgccta tacctggaag tccacaagtg ttcacatccg ggctgccagc atttgtgtct
 241 agtcctactt taccggtggc tcccattcct tcaccgctc ccgcaacacc tttacctcca
 301 ccggcactct tacccccgt aaccacgtct tcctcccaa tccctccatc ccatcctgtg
 361 tctccgggga ccaggatac tcattctcca tctcctgcat tgccaccac gcagtctcca
 421 gagtcttctc aaaggccacc gcttcaagt cctacaggaa ggccagactc ttcaacacct
 481 atgcgtccgc caccctcgca gcagactaca ctccacact cacccacgac tcctccaccc
 541 gagcctccct ccaagactgtc accagactct ttagctccgt ctaccctgcg tagcctgaga
 601 aaaagaagc tatcgtcccc ccaaggtccc tctacactaa accaaatatg tcagtcgccc
 661 ccagtctctc ccctagatg tgacttcgcc aaccgtagtg tgtaccccc atgggccaca
 721 gagtccccga tctacgtggg atcatccagc gatggcgata ctccgccacg ccaaccgcct
 781 acatctccca tctccatagg atcatcatcc ccgtctgagg gatcctgggg tgatgacaca
 841 gccatgttgg tgctccttgc ggagattgca gaagaagcat ccaagaatga aaaagaatgt
 901 tccgaaaata atcaggctgg cgaggataat ggggacaacg agattagcaa ggaaagtcag
 961 gttgacaagg atgacaatga caataaggat gatgaggagg agcaggagac agatgaggag
1021 gacgaggagg atgacgagga ggatgacgag gaggatgacg aggaggatga cgaggaggat
1081 gacgaggagg atgacgagga ggatgacgag gaggatgacg aggaggatga cgaggaggat
1141 gacgaggagg atgacgagga ggagacgag gacgaggacg aggaggagga cgaggaggag
1201 gaggacgagg aggatgacga tgatgaggac aatgaggacg aggaggatga cgaggaggag
1261 gacaagaagg aggacgagga ggacggggc gatggaaaca aaacgttgag catccaaagt
1321 tcacaacagc agcaggagcc acaacagcag gagccacagc agcaggagcc acagcagcag
1381 gagccctgc aggagccaca acagcaggag ccacagcagc aggagccaca gcagcaggag
1441 ccctgcagg agccacaaca gcaggagcca cagcagcagg agccctgca ggagccacaa
1501 cagcaggagc cacaacagca ggagccacag cagcaggagc cacagcagca ggagccacag
1561 cagcaggagc cacagcagca ggagccacag cagcaggagc cacagcagca ggagccacag
1621 cagcaggagc cacagcagca ggagccacag cagcgggagc cacagcagcg ggagcccag
1681 cagcgggagc cacagcagcg ggagccacag cagcgggagc cacagcagcg ggagccacag
1741 cagcgggagc cacagcagcg ggagccacag cagcgggagc cacagcagca ggatgagcag
1801 cagcaggatg agcagcagca ggatgagcag cagcaggatg agcagcagca ggatgagcag
1861 cagcaggatg agcagcagca ggatgagcag cagcaggatg agcagcagca ggatgagcag
1921 cagcaggatg agcagcagca ggatgagcag cagcaggatg agcagcagca ggatgagcag
1981 cagcaggatg agcagcagca ggatgagcag cagcaggatg agcagcagca ggatgagcag
2041 cagcaggatg agcagcagca ggatgagcag cagcaggatg agcagcagca ggatgagcag
2101 gagcagcagg atgagcagga gcagcaggat gagcaggagc agcaggatga gcagcagcag
2161 gatgagcagc agcagcagga tgagcagcag cagcaggatg agcagcagca gcaggatgag
2221 cagcagcagc aggatgagca gcagcagcag gatgaacagg agcagcagga ggagcaggag
2291 cagcaggagg agcaggagca ggagttagag gagcaggagc aggagttaga ggatcaggag
2341 caggagttag aggagcagga gcaggagtta ggggagcagg agcaggagtt agaggagcag
2401 gagcaggagt tagaggagca ggagcaggag ttagaggagc aggagcagga gttagaggag
2461 caggagcagg agttagagga gcaggagcag gagttagagg agcaggagca ggagttagag
2521 gagcaggagg tggaagagca agagcaggag gtggaagagc aagagcagga gcaggaagag
2581 caggaattag aggaggtgga ggagcaagag caggagcagg aggagcagga ggagcaggag
2641 ttagaggagg tggaagagca ggaagagcag gagttagagg aggtggaaga gcaggaagag
2701 caggagttag aggaggtgga agagcaggag caggagcagg agttagaggt ggaagagcag
2761 gagcagcagg ggtggaaca gcaggagcag gagacggtgg aagagccat aatcttgcac
2821 gggtcgtcat ccgaggacga aatggaagtg gattaccctg ttgttagcac acatgaacaa
2881 attgccagta gccaccagg agataataca ccagacgatg accaacaacc tggccatct
2941 cgcgaatacc gctatgtact cagaacatca ccacccaca gacctggagt tcgtatgagg
3001 cgcgttccag ttacccaccc aaaaaagcca catccaagat accaacaacc accggtccct
3061 tacagacaga tagatgattg tcctgccaaa gctaggccac aacacatctt ttatagaccgc
3121 tttttgggaa aggatggaag acgagatcca aagtgtcaat ggaagtttgc agtgatttt
3181 tgggcaatg accatacgg acttaaaaaa ttatctcagg ccttccagtt tggaggagta
```

*Fig. 2A*

```
3241 aaggcaggcc ccgtgtcctg cttgcccac cctggaccag accagtcgcc cataacttac
3301 tgtgtatatg tgtattgtca gaacaaagac acaagtaaga aagtacaaat ggcccgccta
3361 gcctgggaag ctagtcaccc cctggcagga aacctacaat cttccatagt taagtttaaa
3421 aagccctgc cattaaccca gccaggggaa aaccaaggtc ctggggactc tccacaggaa
3481 atgacataa
```

| | | | | | | |
|---|---|---|---|---|---|---|
| A*010101 | A*010102 | A*0102 | A*0103 | A*0104N | A*0106 | A*0107 |
| A*0108 | A*0109 | A*020101 | A*020102 | A*020103 | A*020104 | A*020105 |
| A*020106 | A*020107 | A*020108 | A*020109 | A*0202 | A*0203 | A*0204 |
| A*0205 | A*0206 | A*0207 | A*0208 | A*0209 | A*0210 | A*0211 |
| A*0212 | A*0213 | A*0214 | A*0215N | A*0216 | A*021701 | A*021702 |
| A*0218 | A*0219 | A*022001 | A*022002 | A*0221 | A*0222 | A*0224 |
| A*0225 | A*0226 | A*0227 | A*0228 | A*0229 | A*0230 | A*0231 |
| A*0232N | A*0233 | A*0234 | A*0235 | A*0236 | A*0237 | A*0238 |
| A*0239 | A*0240 | A*0241 | A*0242 | A*0243N | A*0244 | A*0245 |
| A*0246 | A*0247 | A*0248 | A*0249 | A*0250 | A*0251 | A*0252 |
| A*0253N | A*0254 | A*0255 | A*0256 | A*0257 | A*0258 | A*0259 |
| A*0260 | A*0261 | A*0262 | A*03010101 | A*03010102N | A*030102 | A*030103 |
| A*0302 | A*0303N | A*0304 | A*0305 | A*0306 | A*0307 | A*0308 |
| A*0309 | A*0310 | A*0311N | A*110101 | A*110102 | A*1102 | A*1103 |
| A*1104 | A*1105 | A*1106 | A*1107 | A*1108 | A*1109 | A*1110 |
| A*1111 | A*1112 | A*1113 | A*1114 | A*2301 | A*2302 | A*2303 |
| A*2304 | A*2305 | A*2306 | A*2307N | A*2308N | A*2309 | |
| A*24020101 | A*24020102L | A*240202 | A*240203 | A*240204 | A*240301 | A*240302 |
| A*2404 | A*2405 | A*2406 | A*2407 | A*2408 | A*2409N | A*2410 |
| A*2411N | A*2413 | A*2414 | A*2415 | A*2417 | A*2418 | A*2419 |
| A*2420 | A*2421 | A*2422 | A*2423 | A*2424 | A*2425 | A*2426 |
| A*2427 | A*2428 | A*2429 | A*2430 | A*2431 | A*2432 | A*2433 |
| A*2434 | A*2435 | A*2436N | A*2437 | A*2438 | A*2501 | A*2502 |
| A*2503 | A*2504 | A*2601 | A*2602 | A*2603 | A*2604 | A*2605 |
| A*2606 | A*2607 | A*2608 | A*2609 | A*2610 | A*2611N | A*2612 |
| A*2613 | A*2614 | A*2615 | A*2616 | A*2617 | A*2618 | |
| A*29010101 | A*29010102N | A*290201 | A*290202 | A*2903 | A*2904 | A*2905 |
| A*2906 | A*2907 | A*2908N | A*2909 | A*3001 | A*3002 | A*3003 |
| A*3004 | A*3006 | A*3007 | A*3008 | A*3009 | A*3010 | A*3011 |
| A*3012 | A*310102 | A*3102 | A*3103 | A*3104 | A*3105 | A*3106 |
| A*3107 | A*3108 | A*3109 | A*3201 | A*3202 | A*3203 | A*3204 |
| A*3205 | A*3206 | A*3207 | A*3301 | A*3302 | A*3303 | A*3305 |
| A*3306 | A*3307 | A*3401 | A*3402 | A*3403 | A*3404 | A*3405 |
| A*3601 | A*3602 | A*3603 | A*3604 | A*4301 | A*6601 | A*6602 |
| A*6603 | A*6604 | A*680101 | A*680102 | A*6802 | A*680301 | A*680302 |
| A*6804 | A*6805 | A*6806 | A*6807 | A*6808 | A*6809 | A*6810 |
| A*6811N | A*6812 | A*6813 | A*6814 | A*6815 | A*6816 | A*6817 |
| A*6818N | A*6819 | A*6820 | A*6821 | A*6822 | A*6823 | A*6824 |
| A*6901 | A*7401 | A*7402 | A*7403 | A*7404 | A*7405 | A*7406 |
| A*7407 | A*7408 | A*7409 | A*8001 | B*070201 | B*070202 | B*070203 |
| B*0703 | B*0704 | B*0705 | B*0706 | B*0707 | B*0708 | B*0709 |
| B*0710 | B*0711 | B*0712 | B*0713 | B*0714 | B*0715 | B*0716 |
| B*0717 | B*0718 | B*0719 | B*0720 | B*0721 | B*0722 | B*0723 |
| B*0724 | B*0725 | B*0726 | B*0727 | B*0728 | B*0729 | B*0730 |
| B*0731 | B*0801 | B*0802 | B*0803 | B*0804 | B*0805 | B*0806 |
| B*0807 | B*0808N | B*0809 | B*0810 | B*0811 | B*0812 | B*0813 |
| B*0814 | B*0815 | B*0816 | B*0817 | B*0818 | B*0819N | B*1301 |
| B*1302 | B*1303 | B*1304 | B*1306 | B*1307N | B*1308 | B*1309 |
| B*1310 | B*1311 | B*1401 | B*1402 | B*1403 | B*1404 | B*1405 |
| B*140601 | B*140602 | B*15010101 | B*15010102N | B*150102 | B*150103 | B*150104 |
| B*1502 | B*1503 | B*1504 | B*1505 | B*1506 | B*1507 | B*1508 |
| B*1509 | B*1510 | B*151101 | B*151102 | B*1512 | B*1513 | B*1514 |

*Fig. 4A*

| | | | | | | |
|---|---|---|---|---|---|---|
| B*1515 | B*1516 | B*15170101 | B*15170102 | B*1518 | B*1519 | B*1520 |
| B*1521 | B*1523 | B*1524 | B*1525 | B*1526N | B*1527 | B*1528 |
| B*1529 | B*1530 | B*1531 | B*1532 | B*1533 | B*1534 | B*1535 |
| B*1536 | B*1537 | B*1538 | B*1539 | B*1540 | B*1542 | B*1543 |
| B*1544 | B*1545 | B*1546 | B*1547 | B*1548 | B*1549 | B*1550 |
| B*1551 | B*1552 | B*1553 | B*1554 | B*1555 | B*1556 | B*1557 |
| B*1558 | B*1560 | B*1561 | B*1562 | B*1563 | B*1564 | B*1565 |
| B*1566 | B*1567 | B*1568 | B*1569 | B*1570 | B*1571 | B*1572 |
| B*1573 | B*1574 | B*1575 | B*1576 | B*180101 | B*180102 | B*1802 |
| B*1803 | B*1804 | B*1805 | B*1806 | B*1807 | B*1808 | B*1809 |
| B*1810 | B*1811 | B*1812 | B*1813 | B*1814 | B*1815 | B*1817N |
| B*1818 | B*2701 | B*2702 | B*2703 | B*2704 | B*270502 | B*270503 |
| B*270504 | B*270505 | B*270506 | B*2706 | B*2707 | B*2708 | B*2709 |
| B*2710 | B*2711 | B*2712 | B*2713 | B*2714 | B*2715 | B*2716 |
| B*2717 | B*2718 | B*2719 | B*2720 | B*2721 | B*2723 | B*2724 |
| B*2725 | B*350101 | B*350102 | B*3502 | B*3503 | B*3504 | B*3505 |
| B*3506 | B*3507 | B*3508 | B*350901 | B*350902 | B*3510 | B*3511 |
| B*3512 | B*3513 | B*3514 | B*3515 | B*3516 | B*3517 | B*3518 |
| B*3519 | B*3520 | B*3521 | B*3522 | B*3523 | B*3524 | B*3525 |
| B*3526 | B*3527 | B*3528 | B*3529 | B*3530 | B*3531 | B*3532 |
| B*3533 | B*3534 | B*3535 | B*3536 | B*3537 | B*3538 | B*3539 |
| B*3540N | B*3541 | B*3542 | B*3543 | B*3544 | B*3545 | B*3701 |
| B*3702 | B*3703N | B*3704 | B*3705 | B*3801 | B*380201 | B*380202 |
| B*3803 | B*3804 | B*3805 | B*3806 | B*3807 | B*3808 | B*3809 |
| B*390101 | B*390103 | B*390104 | B*390201 | B*390202 | B*3903 | B*3904 |
| B*3905 | B*390601 | B*390602 | B*3907 | B*3908 | B*3909 | B*3910 |
| B*3911 | B*3912 | B*3913 | B*3914 | B*3915 | B*3916 | B*3917 |
| B*3918 | B*3919 | B*3920 | B*3922 | B*3923 | B*3924 | B*3925N |
| B*3926 | B*3927 | B*400101 | B*400102 | B*400103 | B*4002 | B*4003 |
| B*4004 | B*4005 | B*40060101 | B*40060102 | B*4007 | B*4008 | B*4009 |
| B*4010 | B*4011 | B*4012 | B*4013 | B*401401 | B*401402 | B*4015 |
| B*4016 | B*4018 | B*4019 | B*4020 | B*4021 | B*4022N | B*4023 |
| B*4024 | B*4025 | B*4026 | B*4027 | B*4028 | B*4029 | B*4030 |
| B*4031 | B*4032 | B*4033 | B*4034 | B*4035 | B*4036 | B*4037 |
| B*4038 | B*4039 | B*4040 | B*4042 | B*4043 | B*4044 | B*4045 |
| B*4101 | B*4102 | B*4103 | B*4104 | B*4105 | B*4106 | B*4201 |
| B*4202 | B*4204 | B*4205 | B*44020101 | B*44020102S | B*440202 | B*440203 |
| B*440301 | B*440302 | B*4404 | B*4405 | B*4406 | B*4407 | B*4408 |
| B*4409 | B*4410 | B*4411 | B*4412 | B*4413 | B*4414 | B*4415 |
| B*4416 | B*4417 | B*4418 | B*4419N | B*4420 | B*4421 | B*4422 |
| B*4423N | B*4424 | B*4425 | B*4426 | B*4427 | B*4428 | B*4429 |
| B*4430 | B*4431 | B*4432 | B*4433 | B*4434 | B*4435 | B*4501 |
| B*4502 | B*4503 | B*4504 | B*4505 | B*4506 | B*4601 | B*4602 |
| B*47010101 | B*47010102 | B*4702 | B*4703 | B*4704 | B*4801 | B*4802 |
| B*4803 | B*4804 | B*4805 | B*4806 | B*4807 | B*4901 | B*4902 |
| B*4903 | B*5001 | B*5002 | B*5004 | B*510101 | B*510102 | B*510103 |
| B*510104 | B*510105 | B*510201 | B*510202 | B*5103 | B*5104 | B*5105 |
| B*5106 | B*5107 | B*5108 | B*5109 | B*5110 | B*5111N | B*5112 |
| B*511301 | B*511302 | B*5114 | B*5115 | B*5116 | B*5117 | B*5118 |
| B*5119 | B*5120 | B*5121 | B*5122 | B*5123 | B*5124 | B*5126 |
| B*5127N | B*5128 | B*5129 | B*5130 | B*5131 | B*5132 | B*5133 |
| B*5134 | B*520101 | B*520102 | B*520103 | B*520104 | B*5202 | B*5203 |

*Fig. 4B*

| | | | | | | |
|---|---|---|---|---|---|---|
| B*5204 | B*5205 | B*5301 | B*5302 | B*5303 | B*5304 | B*5305 |
| B*5306 | B*5307 | B*5308 | B*5309 | B*5401 | B*5402 | B*5501 |
| B*5502 | B*5503 | B*5504 | B*5505 | B*5507 | B*5508 | B*5509 |
| B*5510 | B*5511 | B*5512 | B*5513 | B*5601 | B*5602 | B*5603 |
| B*5604 | B*560501 | B*560502 | B*5606 | B*5607 | B*5608 | B*5609 |
| B*5610 | B*5611 | B*570101 | B*570102 | B*5702 | B*570301 | B*570302 |
| B*5704 | B*5705 | B*5706 | B*5707 | B*5708 | B*5709 | B*5801 |
| B*5802 | B*5804 | B*5805 | B*5806 | B*5807 | B*5808 | B*5901 |
| B*670101 | B*670102 | B*6702 | B*7301 | B*7801 | B*780201 | B*780202 |
| B*7803 | B*7804 | B*7805 | B*8101 | B*8201 | B*8202 | B*8301 |

A.

B.

Figure 8B:
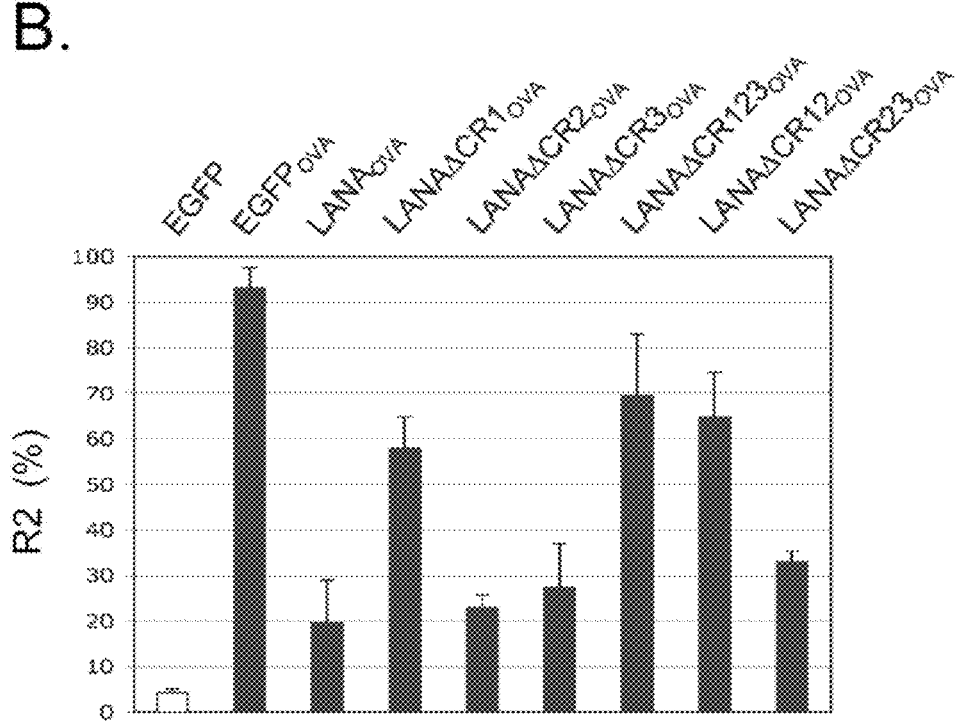
Figures 1, 8C:
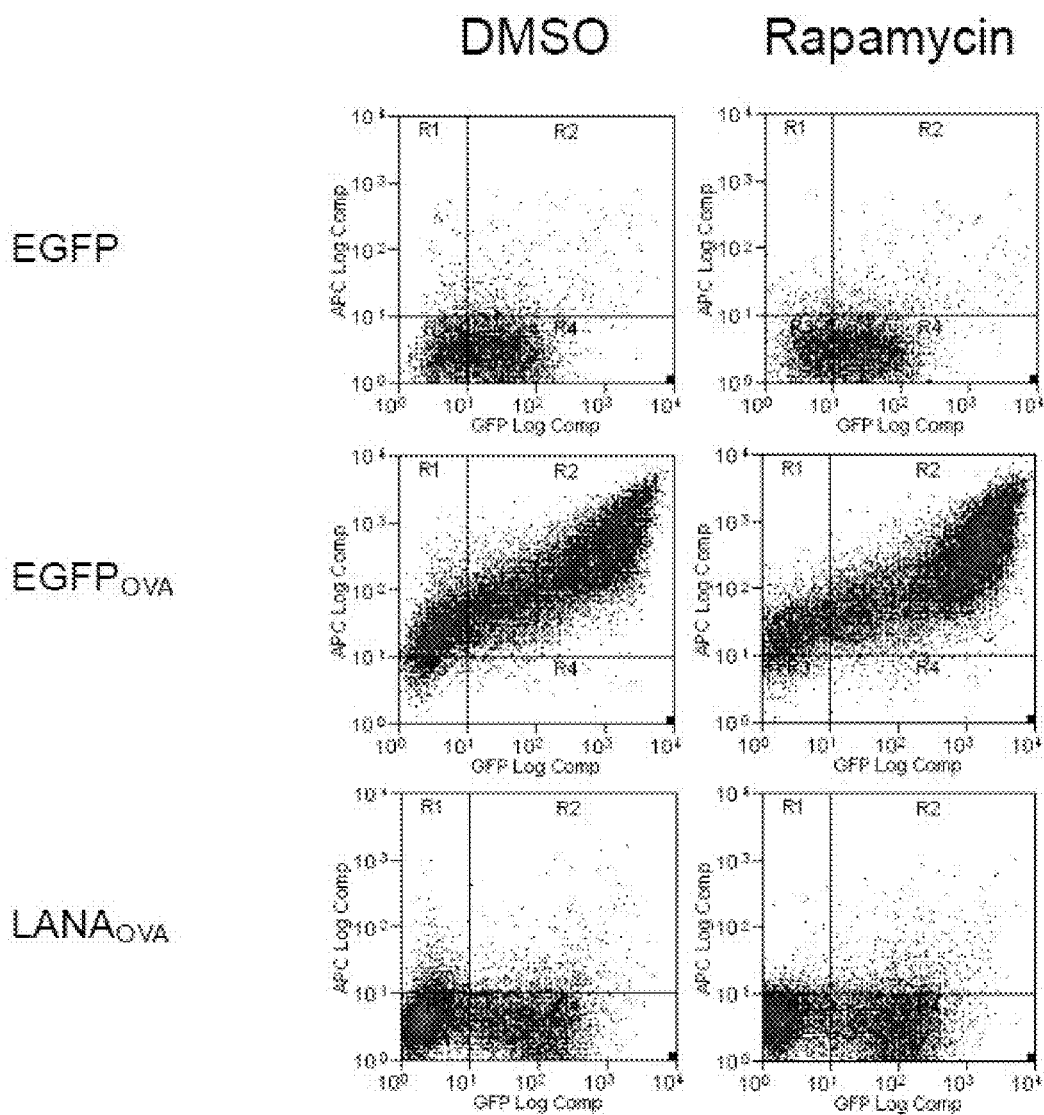
Figures 2, 8C:
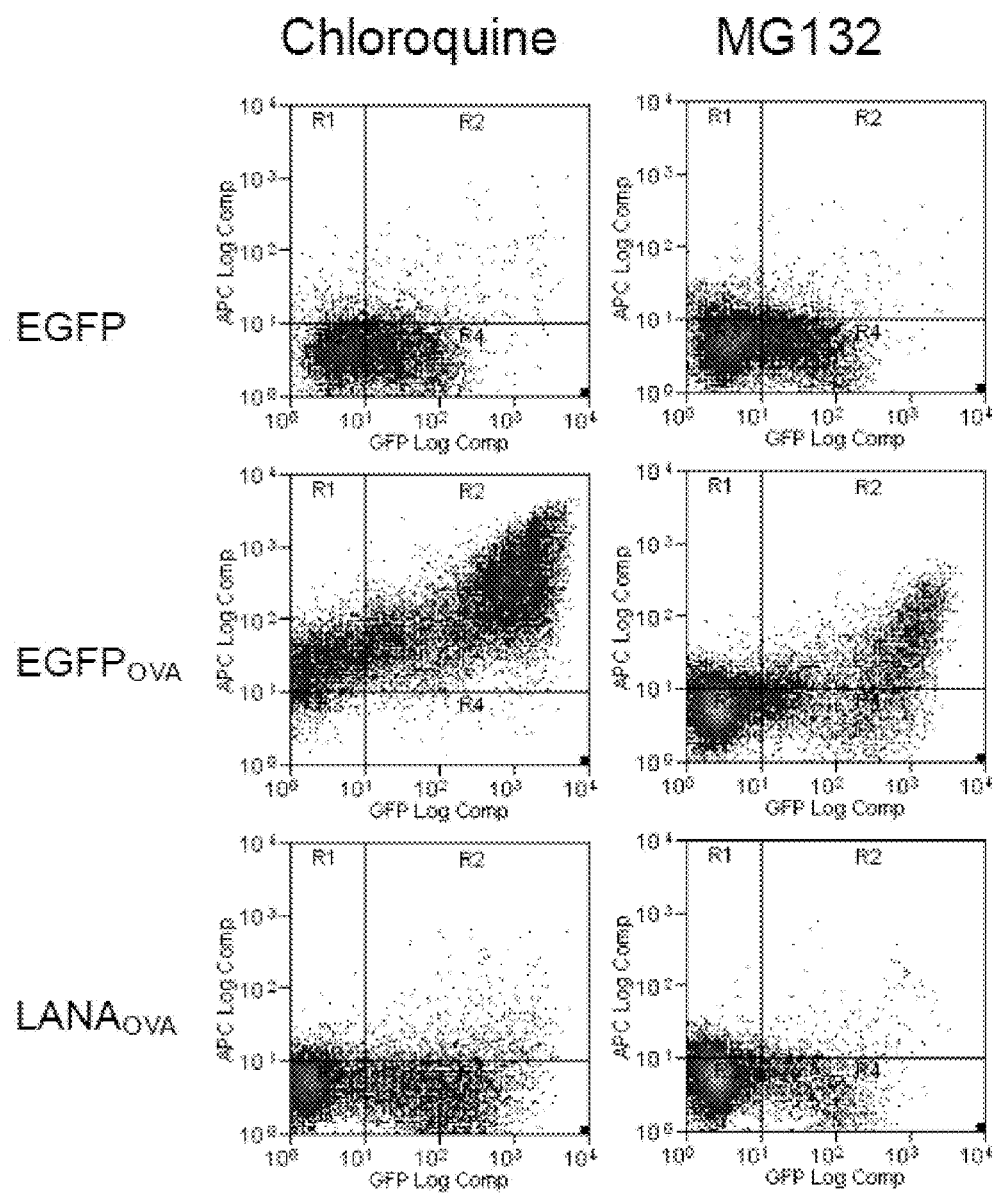
Figures 3, 8C:
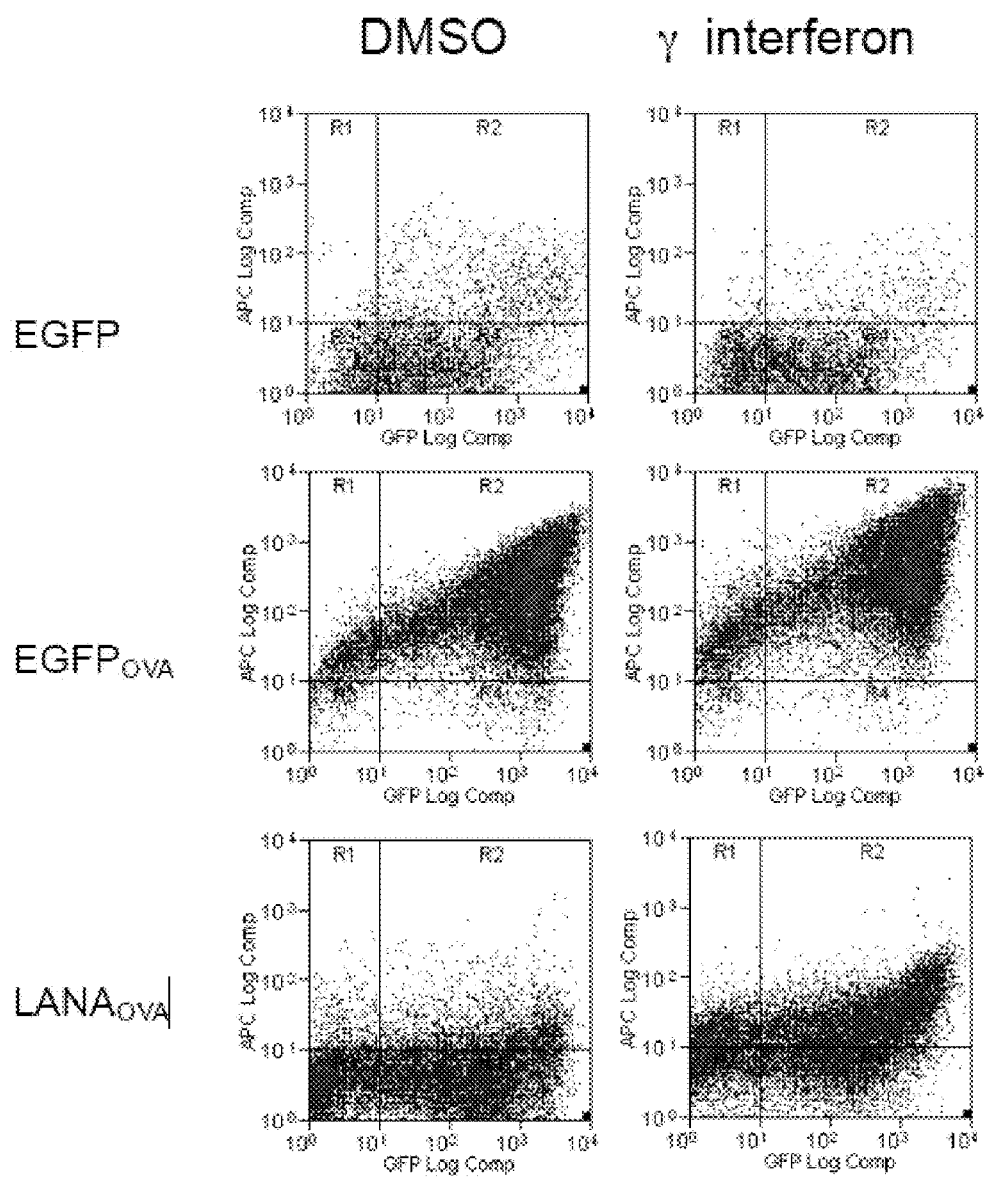

LANAΔCR3_OVA 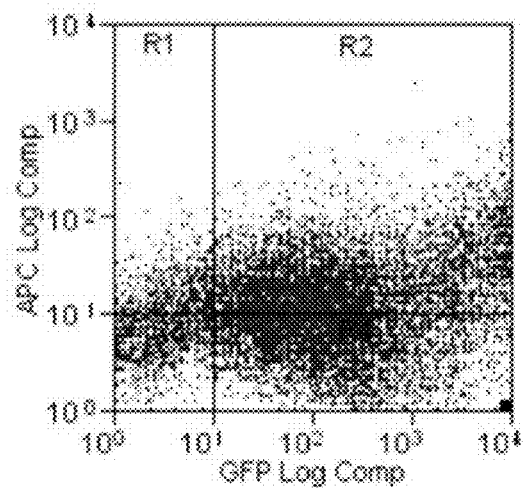
LANAΔCR23_OVA 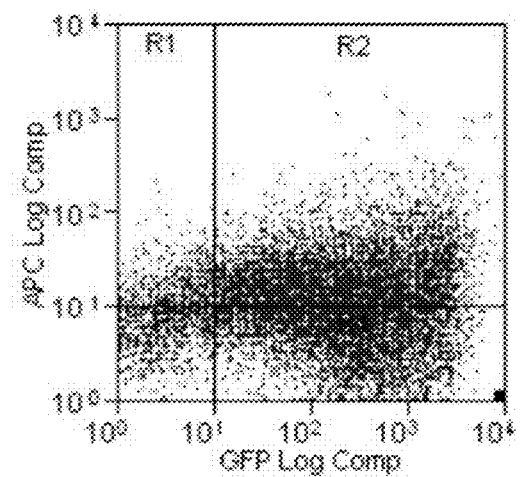
LANA_OVA 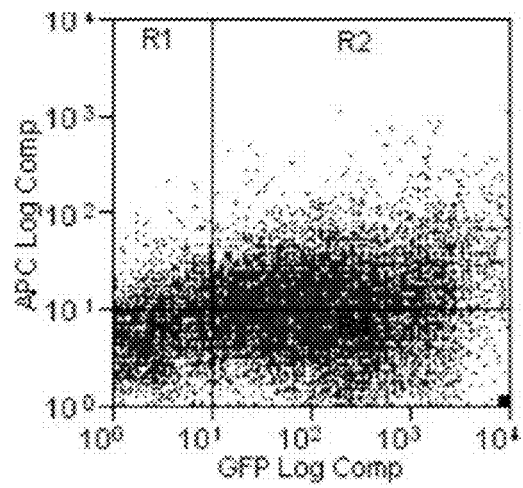
*Fig. 8A-2*

LANAΔCR1<sub>OVA</sub>
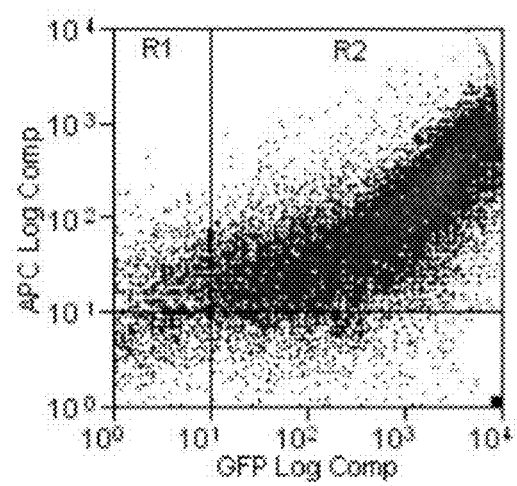
LANAΔCR123<sub>OVA</sub>
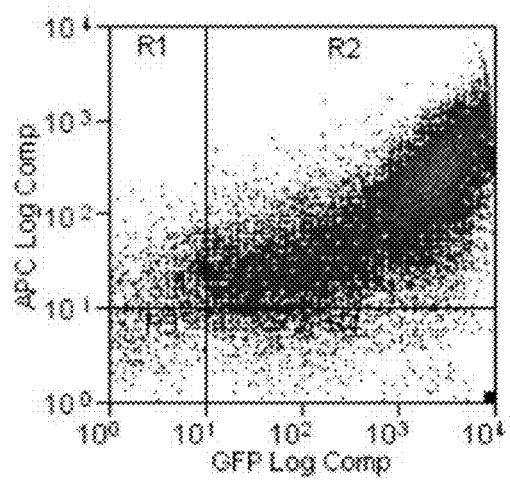
LANAΔCR12<sub>OVA</sub>
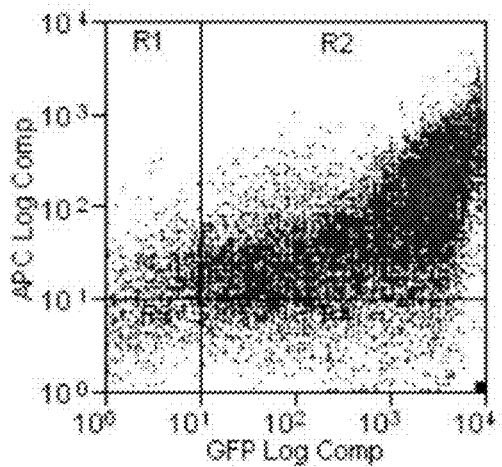
*Fig. 8A-3*

EGFP

EGFP<sub>OVA</sub>

LANA<sub>OVA</sub>

LANAΔCR1<sub>OVA</sub>

SEQUENCE LISTING

```
<160> NUMBER OF SEQ ID NOS: 43

<210> SEQ ID NO 1
<211> LENGTH: 1162
<212> TYPE: PRT
<213> ORGANISM: Homo sapiens

<400> SEQUENCE: 1

Met Ala Pro Pro Gly Met Arg Leu Arg Ser Gly Arg Ser Thr Gly Ala
1               5                   10                  15

Pro Leu Thr Arg Gly Ser Cys Arg Lys Arg Asn Arg Ser Pro Glu Arg
            20                  25                  30

Cys Asp Leu Gly Asp Asp Leu His Leu Gln Pro Arg Arg Lys His Val
        35                  40                  45

Ala Asp Ser Ile Asp Gly Arg Glu Cys Gly Pro His Thr Leu Pro Ile
    50                  55                  60

Pro Gly Ser Pro Thr Val Phe Thr Ser Gly Leu Pro Ala Phe Val Ser
65                  70                  75                  80

Ser Pro Thr Leu Pro Val Ala Pro Ile Pro Ser Pro Ala Pro Ala Thr
                85                  90                  95

Pro Leu Pro Pro Ala Leu Leu Pro Pro Val Thr Thr Ser Ser Ser
            100                 105                 110

Pro Ile Pro Pro Ser His Pro Val Ser Pro Gly Thr Thr Asp Thr His
        115                 120                 125

Ser Pro Ser Pro Ala Leu Pro Pro Thr Gln Ser Pro Glu Ser Ser Gln
    130                 135                 140

Arg Pro Pro Leu Ser Ser Pro Thr Gly Arg Pro Asp Ser Ser Thr Pro
145                 150                 155                 160

Met Arg Pro Pro Ser Gln Gln Thr Thr Pro Pro His Ser Pro Thr
                165                 170                 175

Thr Pro Pro Pro Glu Pro Pro Ser Lys Ser Ser Pro Asp Ser Leu Ala
            180                 185                 190

Pro Ser Thr Leu Arg Ser Leu Arg Lys Arg Arg Leu Ser Ser Pro Gln
        195                 200                 205

Gly Pro Ser Thr Leu Asn Pro Ile Cys Gln Ser Pro Pro Val Ser Pro
    210                 215                 220

Pro Arg Cys Asp Phe Ala Asn Arg Ser Val Tyr Pro Pro Trp Ala Thr
225                 230                 235                 240

Glu Ser Pro Ile Tyr Val Gly Ser Ser Ser Asp Gly Asp Thr Pro Pro
                245                 250                 255

Arg Gln Pro Pro Thr Ser Pro Ile Ser Ile Gly Ser Ser Ser Pro Ser
            260                 265                 270

Glu Gly Ser Trp Gly Asp Asp Thr Ala Met Leu Val Leu Leu Ala Glu
        275                 280                 285

Ile Ala Glu Glu Ala Ser Lys Asn Glu Lys Glu Cys Ser Glu Asn Asn
    290                 295                 300

Gln Ala Gly Glu Asp Asn Gly Asp Asn Glu Ile Ser Lys Glu Ser Gln
```

-continued

```
                305                 310                 315                 320
        Val Asp Lys Asp Asp Asn Asp Asn Lys Asp Asp Glu Glu Gln Glu
                        325                 330                 335

Thr Asp Glu Glu Asp Glu Asp Asp Glu Asp Asp Glu Glu Asp
                        340                 345                 350

Asp Glu Glu Asp Glu Glu Asp Glu Glu Asp Asp Glu Glu Asp
                        355                 360                 365

Asp Glu Glu Asp Glu Glu Asp Asp Glu Glu Asp Asp Glu Asp
                370                 375                 380

Asp Glu Glu Glu Asp Glu Glu Asp Glu Glu Asp Glu Glu Glu
        385                 390                 395                 400

Glu Asp Glu Glu Asp Asp Asp Glu Asp Asn Glu Asp Glu Glu Asp
                        405                 410                 415

Asp Glu Glu Glu Asp Lys Lys Glu Asp Glu Glu Asp Gly Gly Asp Gly
                        420                 425                 430

Asn Lys Thr Leu Ser Ile Gln Ser Ser Gln Gln Gln Glu Pro Gln
                        435                 440                 445

Gln Gln Glu Pro Gln Gln Gln Glu Pro Gln Gln Gln Glu Pro Leu Gln
        450                 455                 460

Glu Pro Gln Gln Gln Glu Pro Gln Gln Gln Glu Pro Gln Gln Gln Glu
        465                 470                 475                 480

Pro Leu Gln Glu Pro Gln Gln Gln Glu Pro Gln Gln Gln Glu Pro Leu
                        485                 490                 495

Gln Glu Pro Gln Gln Gln Glu Pro Gln Gln Gln Glu Pro Gln Gln Gln
                        500                 505                 510

Glu Pro Gln Gln Gln Glu Pro Gln Gln Gln Pro Gln Gln Gln Glu
                        515                 520                 525

Pro Gln Gln Gln Glu Pro Gln Gln Gln Glu Pro Gln Gln Gln Glu Pro
                530                 535                 540

Gln Gln Gln Glu Pro Gln Gln Arg Glu Pro Gln Gln Arg Glu Pro Gln
        545                 550                 555                 560

Gln Arg Glu Pro Gln Gln Arg Glu Pro Gln Gln Arg Glu Pro Gln Gln
                        565                 570                 575

Arg Glu Pro Gln Gln Arg Glu Pro Gln Gln Arg Glu Pro Gln Gln Arg
                        580                 585                 590

Glu Pro Gln Gln Gln Asp Glu Gln Gln Gln Asp Glu Gln Gln Gln Asp
                        595                 600                 605

Glu Gln Gln Gln Asp Glu Gln Gln Gln Asp Glu Gln Gln Gln Asp Glu
                        610                 615                 620

Gln Gln Gln Asp Glu Gln Gln Gln Asp Glu Gln Gln Asp Glu Gln
        625                 630                 635                 640

Gln Gln Asp Glu Gln Gln Asp Glu Gln Gln Gln Asp Glu Gln Gln
                        645                 650                 655

Gln Asp Glu Gln Gln Asp Glu Gln Gln Gln Asp Glu Gln Gln Gln
                        660                 665                 670

Asp Glu Gln Gln Gln Asp Glu Gln Gln Gln Asp Glu Gln Gln Gln Asp
                        675                 680                 685

Glu Gln Gln Gln Asp Glu Gln Gln Gln Asp Glu Gln Gln Gln Asp
                        690                 695                 700

Glu Gln Glu Gln Gln Asp Glu Gln Gln Gln Asp Glu Gln Gln Gln
        705                 710                 715                 720

Asp Glu Gln Gln Gln Gln Asp Glu Gln Gln Gln Asp Glu Gln Gln
                        725                 730                 735
```

```
Gln Gln Asp Glu Gln Gln Gln Gln Asp Glu Gln Gln Gln Asp Glu
        740                 745                 750
Gln Glu Gln Gln Glu Gln Glu Gln Glu Gln Glu Gln Glu Gln Glu
        755                 760                 765
Leu Glu Glu Gln Glu Gln Glu Leu Glu Asp Gln Glu Gln Leu Glu
        770                 775                 780
Glu Gln Glu Gln Glu Leu Glu Gln Glu Gln Glu Leu Glu Gln
785                 790                 795                 800
Glu Gln Glu Leu Glu Glu Gln Glu Gln Glu Leu Glu Gln Glu Gln
                805                 810                 815
Glu Leu Glu Glu Gln Glu Gln Glu Leu Glu Glu Gln Glu Gln Leu
            820                 825                 830
Glu Glu Gln Glu Gln Glu Leu Glu Glu Gln Glu Val Glu Gln Glu
        835                 840                 845
Gln Glu Val Glu Glu Gln Glu Gln Glu Gln Glu Gln Glu Leu Glu
        850                 855                 860
Glu Val Glu Glu Gln Glu Gln Glu Gln Glu Gln Glu Gln Gln Glu
865                 870                 875                 880
Leu Glu Glu Val Glu Glu Gln Glu Gln Glu Leu Glu Glu Val Glu
                885                 890                 895
Glu Gln Glu Gln Glu Gln Leu Glu Glu Val Glu Glu Gln Glu Gln
            900                 905                 910
Glu Leu Glu Glu Val Glu Glu Gln Glu Gln Gln Gly Val Glu Gln Gln
        915                 920                 925
Glu Gln Glu Thr Val Glu Glu Pro Ile Ile Leu His Gly Ser Ser
        930                 935                 940
Glu Asp Glu Met Glu Val Asp Tyr Pro Val Val Ser Thr His Glu Gln
945                 950                 955                 960
Ile Ala Ser Ser Pro Pro Gly Asp Asn Thr Pro Asp Asp Pro Gln
                965                 970                 975
Pro Gly Pro Ser Arg Glu Tyr Arg Tyr Val Leu Arg Thr Ser Pro Pro
            980                 985                 990
His Arg Pro Gly Val Arg Met Arg  Arg Val Pro Val Thr  His Pro Lys
        995                 1000                 1005
Lys Pro  His Pro Arg Tyr Gln  Gln Pro Pro Val Pro  Tyr Arg Gln
    1010                 1015                 1020
Ile Asp  Asp Cys Pro Ala Lys  Ala Arg Pro Gln His  Ile Phe Tyr
    1025                 1030                 1035
Arg Arg  Phe Leu Gly Lys Asp  Gly Arg Arg Asp Pro  Lys Cys Gln
    1040                 1045                 1050
Trp Lys  Phe Ala Val Ile Phe  Trp Gly Asn Asp Pro  Tyr Gly Leu
    1055                 1060                 1065
Lys Lys  Leu Ser Gln Ala Phe  Gln Phe Gly Gly Val  Lys Ala Gly
    1070                 1075                 1080
Pro Val  Ser Cys Leu Pro His  Pro Gly Pro Asp Gln  Ser Pro Ile
    1085                 1090                 1095
Thr Tyr  Cys Val Tyr Val Tyr  Cys Gln Asn Lys Asp  Thr Ser Lys
    1100                 1105                 1110
Lys Val  Gln Met Ala Arg Leu  Ala Trp Glu Ala Ser  His Pro Leu
    1115                 1120                 1125
Ala Gly  Asn Leu Gln Ser Ser  Ile Val Lys Phe Lys  Lys Pro Leu
    1130                 1135                 1140
```

Pro Leu Thr Gln Pro Gly Glu Asn Gln Gly Pro Gly Asp Ser Pro
    1145                1150                1155

Gln Glu Met Thr
    1160

<210> SEQ ID NO 2
<211> LENGTH: 3489
<212> TYPE: DNA
<213> ORGANISM: Homo sapiens

<400> SEQUENCE: 2

| | | |
|---|---|---|
| atggcgcccc cgggaatgcg cctgaggtcg ggacggagca ccggcgcgcc cttaacgaga | 60 |
| ggaagttgta ggaaacgaaa caggtctccg gaaagatgtg accttggcga tgacctacat | 120 |
| ctacaaccgc gaaggaagca tgtcgccgac tccatcgacg gccgggaatg tggaccccac | 180 |
| accttgccta tacctggaag tcccacagtg ttcacatccg ggctgccagc atttgtgtct | 240 |
| agtcctactt taccggtggc tcccattcct tcacccgctc ccgcaacacc tttacctcca | 300 |
| ccggcactct taccccccgt aaccacgtct tcctccccaa tccctccatc ccatcctgtg | 360 |
| tctccgggga ccacggatac tcattctcca tctcctgcat tgccaccac gcagtctcca | 420 |
| gagtcttctc aaaggccacc gctttcaagt cctacaggaa ggccagactc ttcaacacct | 480 |
| atgcgtccgc caccctcgca gcagactaca cctccacact cacccacgac tcctccaccc | 540 |
| gagcctccct ccaagtcgtc accagactct ttagctccgt ctaccctgcg tagcctgaga | 600 |
| aaaagaaggc tatcgtcccc ccaaggtccc tctacactaa acccaatatg tcagtcgccc | 660 |
| ccagtctctc ccctagatg tgacttcgcc aaccgtagtg tgtaccccc atgggccaca | 720 |
| gagtccccga tctacgtggg atcatccagc gatggcgata ctccgccacg ccaaccgcct | 780 |
| acatctccca tctccatagg atcatcatcc ccgtctgagg gatcctgggg tgatgacaca | 840 |
| gccatgttgg tgctccttgc ggagattgca gaagaagcat ccaagaatga aaagaatgt | 900 |
| tccgaaaata atcaggctgg cgaggataat ggggacaacg agattagcaa ggaaagtcag | 960 |
| gttgacaagg atgacaatga caataaggat gatgaggagg agcaggagac agatgaggag | 1020 |
| gacgaggagg atgacgagga ggatgacgag gaggatgacg aggaggatga cgaggaggat | 1080 |
| gacgaggagg atgacgagga ggatgacgag gaggatgacg aggaggatga cgaggaggat | 1140 |
| gacgaggagg atgacgagga ggaggacgag gaggaggacg aggaggga cgaggaggag | 1200 |
| gaggacgagg aggatgacga tgatgaggac aatgaggacg aggaggatga cgaggaggag | 1260 |
| gacaagaagg aggacgagga ggacgggggc gatggaaaca aaacgttgag catccaaagt | 1320 |
| tcacaacagc agcaggagcc acaacagcag gagccacagc agcaggagcc acagcagcag | 1380 |
| gagccctgc aggagccaca acagcaggag ccacagcagc aggagccaca gcagcaggag | 1440 |
| cccctgcagg agccacaaca gcaggagcca cagcagcagg agcccctgca ggagccacaa | 1500 |
| cagcaggagc acaacagca ggagccacag cagcaggagc acagcagca ggagccacag | 1560 |
| cagcaggagc acagcagca ggagccacag cagcaggagc acagcagca ggagccacag | 1620 |
| cagcaggagc acagcagca ggagccacag cagcgggagc acagcagcg ggagcccag | 1680 |
| cagcgggagc acagcagcg ggagccacag cagcgggagc acagcagcg ggagccacag | 1740 |
| cagcgggagc acagcagcg ggagccacag cagcgggagc acagcagca ggatgagcag | 1800 |
| cagcaggatg agcagcagca ggatgagcag cagcaggatg agcagcagca ggatgagcag | 1860 |
| cagcaggatg agcagcagca ggatgagcag cagcaggatg agcagcagca ggatgagcag | 1920 |
| cagcaggatg agcagcagca ggatgagcag cagcaggatg agcagcagca ggatgagcag | 1980 |

```
cagcaggatg agcagcagca ggatgagcag cagcaggatg agcagcagca ggatgagcag    2040
cagcaggatg agcagcagca ggatgagcag cagcaggatg agcagcagca ggatgagcag    2100
gagcagcagg atgagcagga gcagcaggat gagcaggagc agcaggatga gcagcagcag    2160
gatgagcagc agcagcagga tgagcagcag cagcaggatg agcagcagca gcaggatgag    2220
cagcagcagc aggatgagca gcagcagcag gatgaacagg agcagcagga ggagcaggag    2280
cagcaggagg agcaggagca ggagttagag gagcaggagc aggagttaga ggatcaggag    2340
caggagttag aggagcagga gcaggagtta gaggagcagg agcaggagtt agaggagcag    2400
gagcaggagt tagaggagca ggagcaggag ttagaggagc aggagcagga gttagaggag    2460
caggagcagg agttagagga gcaggagcag gagttagagg agcaggagca ggagttagag    2520
gagcaggagg tggaagagca agagcaggag gtggaagagc aagagcagga gcaggaagag    2580
caggaattag aggaggtgga ggagcaagag caggagcagg aggagcagga ggagcaggag    2640
ttagaggagg tggaagagca ggaagagcag gagttagagg aggtggaaga gcaggaagag    2700
caggagttag aggaggtgga agagcaggag cagcaggagt tagaggaggt ggaagagcag    2760
gagcagcagg gggtggaaca gcaggagcag gagacggtgg aagagcccat aatcttgcac    2820
gggtcgtcat ccgaggacga aatggaagtg gattaccctg ttgttagcac acatgaacaa    2880
attgccagta gcccaccagg agataataca ccagacgatg acccacaacc tggcccatct    2940
cgcgaatacc gctatgtact cagaacatca ccaccccaca gacctggagt tcgtatgagg    3000
cgcgttccag ttacccaccc aaaaaagcca catccaagat accaacaacc accggtccct    3060
tacagacaga tagatgattg tcctgcgaaa gctaggccac aacacatctt ttatagacgc    3120
tttttgggaa aggatggaag acgagatcca aagtgtcaat ggaagtttgc agtgattttt    3180
tggggcaatg acccatacgg acttaaaaaa ttatctcagg ccttccagtt tggaggagta    3240
aaggcaggcc ccgtgtcctg cttgccccac cctggaccag accagtcgcc cataacttat    3300
tgtgtatatg tgtattgtca gaacaaagac acaagtaaga aagtacaaat ggcccgccta    3360
gcctgggaag ctagtcaccc cctggcagga aacctacaat cttccatagt taagtttaaa    3420
aagcccctgc cattaaccca gccagggaaa accaaggtc ctgggactc tccacaggaa    3480 atgacataa                                                            3489
```

<210> SEQ ID NO 3
<211> LENGTH: 5
<212> TYPE: PRT
<213> ORGANISM: Artificial Sequence
<220> FEATURE:
<223> OTHER INFORMATION: Derivative of the portion of a LANA1 central
      repeat domain

<400> SEQUENCE: 3

Gln Gln Gln Asp Glu
1               5

<210> SEQ ID NO 4
<211> LENGTH: 5
<212> TYPE: PRT
<213> ORGANISM: Artificial Sequence
<220> FEATURE:
<223> OTHER INFORMATION: Derivative of the portion of a LANA1 central
      repeat domain

<400> SEQUENCE: 4

Gln Gln Gln Glu Pro

-continued

```
<210> SEQ ID NO 5
<211> LENGTH: 5
<212> TYPE: PRT
<213> ORGANISM: Artificial Sequence
<220> FEATURE:
<223> OTHER INFORMATION: Derivative of the portion of a LANA1 central
      repeat domain

<400> SEQUENCE: 5

Gln Glu Leu Glu Glu
1               5

<210> SEQ ID NO 6
<211> LENGTH: 7
<212> TYPE: PRT
<213> ORGANISM: Artificial Sequence
<220> FEATURE:
<223> OTHER INFORMATION: Derivative of the portion of a LANA1 central
      repeat domain
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 6

Gln Glu Gln Xaa Glu Xaa Xaa
1               5

<210> SEQ ID NO 7
<211> LENGTH: 6
<212> TYPE: PRT
<213> ORGANISM: Artificial Sequence
<220> FEATURE:
<223> OTHER INFORMATION: Derivative of the portion of a LANA1 central
      repeat domain

<400> SEQUENCE: 7

Gln Gln Gln Gln Glu Pro
1               5

<210> SEQ ID NO 8
<211> LENGTH: 6
<212> TYPE: PRT
<213> ORGANISM: Artificial Sequence
<220> FEATURE:
<223> OTHER INFORMATION: Derivative of the portion of a LANA1 central
      repeat domain

<400> SEQUENCE: 8

Gln Gln Gln Glu Pro Leu
1               5

<210> SEQ ID NO 9
<211> LENGTH: 5
<212> TYPE: PRT
<213> ORGANISM: Artificial Sequence
<220> FEATURE:
<223> OTHER INFORMATION: Derivative of the portion of a LANA1 central
      repeat domain

<400> SEQUENCE: 9

Gln Gln Arg Glu Pro
1               5
```

```
<210> SEQ ID NO 10
<211> LENGTH: 6
<212> TYPE: PRT
<213> ORGANISM: Artificial Sequence
<220> FEATURE:
<223> OTHER INFORMATION: Derivative of the portion of a LANA1 central
      repeat domain

<400> SEQUENCE: 10

Gln Glu Gln Gln Asp Glu
1               5

<210> SEQ ID NO 11
<211> LENGTH: 6
<212> TYPE: PRT
<213> ORGANISM: Artificial Sequence
<220> FEATURE:
<223> OTHER INFORMATION: Derivative of the portion of a LANA1 central
      repeat domain

<400> SEQUENCE: 11

Gln Gln Gln Gln Asp Glu
1               5

<210> SEQ ID NO 12
<211> LENGTH: 6
<212> TYPE: PRT
<213> ORGANISM: Artificial Sequence
<220> FEATURE:
<223> OTHER INFORMATION: Derivative of the portion of a LANA1 central
      repeat domain

<400> SEQUENCE: 12

Gln Glu Gln Gln Glu Glu
1               5

<210> SEQ ID NO 13
<211> LENGTH: 7
<212> TYPE: PRT
<213> ORGANISM: Artificial Sequence
<220> FEATURE:
<223> OTHER INFORMATION: Derivative of the portion of a LANA1 central
      repeat domain

<400> SEQUENCE: 13

Gln Glu Gln Glu Leu Glu Asp
1               5

<210> SEQ ID NO 14
<211> LENGTH: 7
<212> TYPE: PRT
<213> ORGANISM: Artificial Sequence
<220> FEATURE:
<223> OTHER INFORMATION: Derivative of the portion of a LANA1 central
      repeat domain

<400> SEQUENCE: 14

Gln Glu Gln Glu Leu Glu Glu
1               5

<210> SEQ ID NO 15
<211> LENGTH: 7
<212> TYPE: PRT
<213> ORGANISM: Artificial Sequence
<220> FEATURE:
<223> OTHER INFORMATION: Derivative of the portion of a LANA1 central
      repeat domain
```

-continued

<400> SEQUENCE: 15

Gln Glu Gln Glu Val Glu Glu
1               5

<210> SEQ ID NO 16
<211> LENGTH: 8
<212> TYPE: PRT
<213> ORGANISM: Artificial Sequence
<220> FEATURE:
<223> OTHER INFORMATION: Derivative of the portion of a LANA1 central
      repeat domain

<400> SEQUENCE: 16

Gln Glu Leu Glu Glu Val Glu Glu
1               5

<210> SEQ ID NO 17
<211> LENGTH: 11
<212> TYPE: PRT
<213> ORGANISM: Artificial Sequence
<220> FEATURE:
<223> OTHER INFORMATION: Derivative of the portion of a LANA1 central
      repeat domain

<400> SEQUENCE: 17

Gln Glu Glu Gln Glu Leu Glu Glu Val Glu Glu
1               5                   10

<210> SEQ ID NO 18
<211> LENGTH: 5
<212> TYPE: PRT
<213> ORGANISM: Artificial Sequence
<220> FEATURE:
<223> OTHER INFORMATION: Derivative of the portion of a LANA1 central
      repeat domain

<400> SEQUENCE: 18

Asp Glu Gln Gln Gln
1               5

<210> SEQ ID NO 19
<211> LENGTH: 15
<212> TYPE: RNA
<213> ORGANISM: Artificial Sequence
<220> FEATURE:
<223> OTHER INFORMATION: Example of single interation

<400> SEQUENCE: 19
caagacgagc aacaa                                              15

<210> SEQ ID NO 20
<211> LENGTH: 15
<212> TYPE: DNA
<213> ORGANISM: Artificial Sequence
<220> FEATURE:
<223> OTHER INFORMATION: Example of single interation

<400> SEQUENCE: 20
ttgttgttgc tcgtc                                              15

<210> SEQ ID NO 21
<211> LENGTH: 30
<212> TYPE: DNA
<213> ORGANISM: Artificial Sequence
<220> FEATURE:
<223> OTHER INFORMATION: Example of double iteration

<400> SEQUENCE: 21
caagacgagc aacaacaaga tgaacagcaa                                    30

<210> SEQ ID NO 22
<211> LENGTH: 30
<212> TYPE: DNA
<213> ORGANISM: Artificial Sequence
<220> FEATURE:
<223> OTHER INFORMATION: Example of double iteration

<400> SEQUENCE: 22
ttgttgctgt tcatcttgtt gttgctcgtc                                    30

<210> SEQ ID NO 23
<211> LENGTH: 8
<212> TYPE: PRT
<213> ORGANISM: Artificial Sequence
<220> FEATURE:
<223> OTHER INFORMATION: dominant H2-Kb restricted chicken ovalbumin
      epitope

<400> SEQUENCE: 23

Ser Ile Ile Asn Phe Glu Lys Leu
1               5

<210> SEQ ID NO 24
<211> LENGTH: 9
<212> TYPE: PRT
<213> ORGANISM: Artificial Sequence
<220> FEATURE:
<223> OTHER INFORMATION: Potential binding epitope to H2-Kd

<400> SEQUENCE: 24

Ala Met Leu Val Leu Leu Ala Glu Ile
1               5

<210> SEQ ID NO 25
<211> LENGTH: 9
<212> TYPE: PRT
<213> ORGANISM: Artificial Sequence
<220> FEATURE:
<223> OTHER INFORMATION: Potential binding epitope for H2-Kd

<400> SEQUENCE: 25

Ser Ser Pro Gln Gly Pro Ser Thr Leu
1               5

<210> SEQ ID NO 26
<211> LENGTH: 9
<212> TYPE: PRT
<213> ORGANISM: Artificial Sequence
<220> FEATURE:
<223> OTHER INFORMATION: Potential binding epitope for H2-Kd

<400> SEQUENCE: 26

Leu Ala Pro Ser Thr Leu Arg Ser Leu
1               5

<210> SEQ ID NO 27
<211> LENGTH: 27
<212> TYPE: DNA
<213> ORGANISM: Artificial Sequence
<220> FEATURE:
<223> OTHER INFORMATION: LANA1 heterologous constructs

<400> SEQUENCE: 27

```
gaatccatgg cgcccccggg aatgcgc                                        27
```

<210> SEQ ID NO 28
<211> LENGTH: 29
<212> TYPE: DNA
<213> ORGANISM: Artificial Sequence
<220> FEATURE:
<223> OTHER INFORMATION: LANA1 heterologous constructs

<400> SEQUENCE: 28

```
ccgatatcct tattgtcatt gtcatcctt                                      29
```

<210> SEQ ID NO 29
<211> LENGTH: 28
<212> TYPE: DNA
<213> ORGANISM: Artificial Sequence
<220> FEATURE:
<223> OTHER INFORMATION: LANA1 heterologous constructs

<400> SEQUENCE: 29

```
cgatatcatc ttgcacgggt cgtcatcc                                       28
```

<210> SEQ ID NO 30
<211> LENGTH: 29
<212> TYPE: DNA
<213> ORGANISM: Artificial Sequence
<220> FEATURE:
<223> OTHER INFORMATION: LANA1 heterologous constructs

<400> SEQUENCE: 30

```
ccaagctttg tcatttcctg tggagagtc                                      29
```

<210> SEQ ID NO 31
<211> LENGTH: 29
<212> TYPE: DNA
<213> ORGANISM: Artificial Sequence
<220> FEATURE:
<223> OTHER INFORMATION: LANA1 heterologous constructs

<400> SEQUENCE: 31

```
ccgaattcga caaggatgac aatgacaat                                      29
```

<210> SEQ ID NO 32
<211> LENGTH: 29
<212> TYPE: DNA
<213> ORGANISM: Artificial Sequence
<220> FEATURE:
<223> OTHER INFORMATION: LANA1 heterologous constructs

<400> SEQUENCE: 32

```
ccgatatcga caaggatgac aatgacaat                                      29
```

<210> SEQ ID NO 33
<211> LENGTH: 29
<212> TYPE: DNA
<213> ORGANISM: Artificial Sequence
<220> FEATURE:
<223> OTHER INFORMATION: LANA1 heterologous constructs

<400> SEQUENCE: 33

```
cgatatcgct caacgttttg tttccatcg                                      29
```

<210> SEQ ID NO 34
<211> LENGTH: 30
<212> TYPE: DNA

```
<213> ORGANISM: Artificial Sequence
<220> FEATURE:
<223> OTHER INFORMATION: LANA1 heterologous constructs

<400> SEQUENCE: 34
gaattcggcg atggaaacaa aacgttgagc                                    30

<210> SEQ ID NO 35
<211> LENGTH: 30
<212> TYPE: DNA
<213> ORGANISM: Artificial Sequence
<220> FEATURE:
<223> OTHER INFORMATION: LANA1 heterologous constructs

<400> SEQUENCE: 35
gatatcggcg atggaaacaa aacgttgagc                                    30

<210> SEQ ID NO 36
<211> LENGTH: 29
<212> TYPE: DNA
<213> ORGANISM: Artificial Sequence
<220> FEATURE:
<223> OTHER INFORMATION: LANA1 heterologous constructs

<400> SEQUENCE: 36
gatatcctcc tgctcctgct cctcctgct                                     29

<210> SEQ ID NO 37
<211> LENGTH: 30
<212> TYPE: DNA
<213> ORGANISM: Artificial Sequence
<220> FEATURE:
<223> OTHER INFORMATION: LANA1 heterologous constructs

<400> SEQUENCE: 37
gaattcttag aggagcagga gcaggagtta                                    30

<210> SEQ ID NO 38
<211> LENGTH: 30
<212> TYPE: DNA
<213> ORGANISM: Artificial Sequence
<220> FEATURE:
<223> OTHER INFORMATION: LANA1 heterologous constructs

<400> SEQUENCE: 38
gatatcttag aggagcagga gcaggagtta                                    30

<210> SEQ ID NO 39
<211> LENGTH: 30
<212> TYPE: DNA
<213> ORGANISM: Artificial Sequence
<220> FEATURE:
<223> OTHER INFORMATION: LANA1 heterologous constructs

<400> SEQUENCE: 39
gatatccaag attatgggct cttccaccgt                                    30

<210> SEQ ID NO 40
<211> LENGTH: 30
<212> TYPE: DNA
<213> ORGANISM: Artificial Sequence
<220> FEATURE:
<223> OTHER INFORMATION: Primer for clones fused with GFP

<400> SEQUENCE: 40
catggatccg ccaccatggt gagcaagggc                                    30
```

```
<210> SEQ ID NO 41
<211> LENGTH: 29
<212> TYPE: DNA
<213> ORGANISM: Artificial Sequence
<220> FEATURE:
<223> OTHER INFORMATION: Primer for clones fused with GFP

<400> SEQUENCE: 41
cttgaattcc ttgtacagct cgtccatgc                                    29

<210> SEQ ID NO 42
<211> LENGTH: 30
<212> TYPE: DNA
<213> ORGANISM: Artificial Sequence
<220> FEATURE:
<223> OTHER INFORMATION: Primer for C-terminus GFP constructs

<400> SEQUENCE: 42
cataagcttg tgagcaaggg cgaggagctg                                   30

<210> SEQ ID NO 43
<211> LENGTH: 6
<212> TYPE: PRT
<213> ORGANISM: Artificial Sequence
<220> FEATURE:
<223> OTHER INFORMATION: Derivative of the portion of a LANA1 central
      repeat domain

<400> SEQUENCE: 43

Gln Gln Gln Arg Glu Pro
1               5
```

METHOD OF ENHANCING KSHV LANA1 IMMUNOGENICITY

CROSS-REFERENCE TO RELATED APPLICATIONS

This application is a Divisional of U.S. patent application Ser. No. 13/334,657, filed on Dec. 22, 2011, which is a Continuation-In-Part of U.S. patent application Ser. No. 13/221,040, filed on Aug. 30, 2011, now abandoned, which is a Continuation of U.S. patent application Ser. No. 12/191,698, filed on Aug. 14, 2008, now abandoned, which claims the benefit under 35 U.S.C. § 119(e) to U.S. Provisional Patent Application No. 60/955,898, filed on Aug. 15, 2007, and also claims the benefit under 35 U.S.C. § 119(e) to U.S. Provisional Patent Application No. 61/427,225, filed on Dec. 27, 2010, each of which is incorporated herein by reference in its entirety.

STATEMENT REGARDING FEDERAL FUNDING

This invention was made with government support under Grant Nos. R01 CA67391 and NCI121930 awarded by the National Institutes of Health. The government has certain rights in the invention.

The Sequence Listing associated with this application is filed in electronic format via EFS-Web and is hereby incorporated by reference into the specification in its entirety. The name of the text file containing the Sequence Listing is 1602823_ST25.txt. The size of the text file is 23,854 bytes, and the text file was created on Jun. 2, 2016.

An immunogenically-enhanced Kaposi sarcoma-associated herpesvirus latency-associated nuclear antigen 1 ("KSHV LANA1") polypeptide and related methods of eliciting an immune response to KSHV LANA1 are provided. Also described herein is a novel polypeptide capable of inhibiting degradation of a protein or retarding synthesis of a protein when attached to or incorporated within that protein.

Viral latency is one mechanism viruses use to reduce expression of proteins susceptible to immune recognition. During latency, the large human DNA tumor viruses, Epstein-Barr virus (EBV or HHV4) and Kaposi's sarcoma-associated herpesvirus (KSHV or HHV8) exist as episomes that replicate in tandem with the cell genome using host replication proteins. To be retained in cells, however, the expression of several viral proteins from the latent viral genome must be maintained. The Epstein-Barr nuclear antigen 1 (EBNA1) and latency-associated nuclear antigen 1 (LANA1) are analogous to each other and act to tether the viral episomes to the host genome for EBV and KSHV respectively, allowing proper segregation of virus during cell division. Both viral proteins have DNA binding domains at each end with long intervening central repeat sequences.

EBNA1 has been extensively studied for its intrinsic properties that retard peptide antigen presentation. The central EBNA1 Gly-Ala repeat region (GAr) was shown to inhibit its own proteosomal degradation in cis, thus reducing the pool of EBNA1 peptides available for antigen processing. Proteasomes are directly coupled to peptide translocation machinery that pump viral peptides into the lumen of the endoplasmic reticulum (ER), allowing efficient loading of viral peptides on the MHC I prior to transport to the plasma membrane. More recently it has been reported that misfolded proteins which are rapidly shuttled into proteasomal pathways comprise a major source for MHC-presented peptides. Up to 20% of all newly synthesized cellular proteins are misfolded, so-called defective ribosomal products (DRiPs), and processed in this manner allowing robust and rapid immune surveillance sampling of foreign proteins. EBNA1 GAr appears to avoid DRiP formation by retarding its own ribosomal translation. While slower EBNA1 translation generates fewer misfolded EBNA1 molecules, sufficient amounts of this viral protein accumulate because of its decreased proteasomal protein turnover. Since the EBNA1 GAr domain is responsible for both protein degradation inhibition and translation retardation, distinguishing the importance between these two effects for EBNA1 immune evasion has been difficult.

KSHV is a gammaherpesvirus relative of EBV that causes Kaposi's sarcoma (KS), primary effusion lymphoma and a portion of multicentric Castleman's disease. With the onset of the African AIDS pandemic, KS is now the most commonly reported neoplasm for adults in parts of sub-Saharan Africa. Although KS is a major unmet public health burden in Africa, this problem is only likely to be addressed through development of inexpensive vaccines or immunotherapy. Identifying mechanisms used by KSHV to avoid immune recognition will assist in the identification of effective KSHV vaccine antigens.

KSHV LANA1 has a central repeat (CR) domain (321-937 aa) comprising repeats rich in glutamine (Q), glutamate (E), and aspartate (D). While LANA1 and EBNA1 are functionally and structurally analogous, they do not share amino acid similarity in their canonical open reading frames. Unlike EBNA1 GAr repeats, the LANA1 repeats are imperfect and can be further divided into three subdomains: CR1, CR2, and CR3. Using the entire central repeat region, Zaldumbide et al. reported that the entire CR functions as a cis-acting inhibitor of MHC-antigen processing, analogous to EBNA1 GAr (Zaldumbide, A., et al., 2007. In cis inhibition of antigen processing by the latency-associated nuclear antigen I of Kaposi sarcoma herpes virus. *Mol. Immunol.* 44, 1352-1360). More detailed analyses have been hampered by the difficulty in cloning these extensively repeated domains.

SUMMARY

We previously showed that a junctional domain between CR2 and CR3 participates in retardation of LANA1 translation, like the EBNA1 GAr, and that this effect is likely to be caused by peptide rather than mRNA structures, we also found that some LANA1 isoforms have abnormally prolonged half-lives, suggesting that the CR may avoid CTL processing through the same mechanisms previously described for EBNA1 GAr.

Here, however, we map the individual CR domains involved in surface presentation of ovalbumin peptides fused to various LANA1 constructs. We find that neither CR2 nor CR3 are primarily responsible for peptide presentation evasion. Instead, CR1 appears to block peptide presentation prior to translocation of peptides into the ER. These data show for the first time that that LANA1 and EBNA1 use different mechanisms to avoid antiviral CTL recognition and indicate that gammaherpesvirus immune evasion is more complex than previously assumed.

The central repeat domain 1 of Kaposi's sarcoma-associated herpesvirus (KSHV) latency associated-nuclear antigen 1 (LANA1) act prior to peptide transport to the endoplasmic reticulum to prevent cis MHC class I antigen presentation KSHV LANA1, a latent protein that must be expressed during chronic infection to maintain the viral genome, inhibits in cis major histocompatibility complex (MHC) class I peptide presentation as a means of immune evasion. Through deletional cloning, we have the localized MHC I immune evasion function to the LANA1 central repeat 1 (CR1) subregion. Other LANA1 CR regions retard LANA1 translation and proteasomal processing in cis but do not markedly inhibit LANA1 peptide processing by MHC I Inhibition of proteasomal processing, but not autophagy, ablates LANA1 peptide presentation. Direct expression of LANA1 into the endoplasmic reticulum (ER) overcomes CR1 inhibition suggesting that CR1 acts prior to peptide translocation into the ER. By physically separating CR1 from these domains, we show that LANA1 evades MHC I peptide processing through a mechanism that is distinct from other herpesviruses such as Epstein-Barr virus (EBV). Although KSHV LANA1 and EBV EBNA1 are functionally similar, they appear to use different mechanisms to evade host cytotoxic lymphocyte surveillance.

The described novel properties and portions of the KSHV LANA1 protein can be exploited in producing an immunogenic composition, such as a vaccine, useful in eliciting cell-mediated immunity to LANA1 and therefore to KSHV. Provided therefore are: an immunogenic composition comprising immunologically-enhanced LANA1 (ieLANA1), a method of making an immunogenic composition comprising ieLANA1, a method of using an immunogenic composition comprising ieLANA1 to vaccinate an individual and a commercial kit for distributing an immunogenic composition comprising ieLANA1 in order to implement the described methods.

In one embodiment, a method is provided of eliciting and/or increasing an immune response to KSHV LANA1 in a subject comprising introducing into a cell of the subject (in vivo or ex vivo) an immunologically-enhanced LANA1 (ieLANA1) polypeptide for eliciting an immune response to LANA1 (e.g. as shown in FIG. 1). The peptide comprises a LANA1 amino acid sequence comprising one or more LANA1 T-cell epitopes, and wherein the LANA1 amino acid sequence is modified to exhibit increased CTL immune response as compared to wild-type LANA1 protein. In one non-limiting embodiment, the polypeptide does not comprise a portion of LANA1 CR1 region, so that the immunologically-enhanced LANA1 polypeptide exhibits increased ability to elicit a CTL immune response as compared to wild-type LANA1 protein. In another non-limiting embodiment, the LANA1 polypeptide comprises the amino acid sequence of FIG. 1 in which a portion of a LANA1 central repeat domain having the capacity to inhibit elicitation of a CTL immune response to LANA1 is modified to decrease the ability of that portion to inhibit elicitation of a CTL immune response to LANA1. For example and without limitation, wherein the LANA1 polypeptide may comprise the amino acid sequence of FIG. 1 in which from amino acids 321-331 to from amino acids 427-428 (including, e.g., amino acids 321-427, 321-428, 331-427, or 331-428) are deleted or replaced in the LANA1 polypeptide are deleted. This would yield an ieLANA, for illustration purposes only and without limitation, having bases 1-320 attached to bases 428-1162 of the amino acid sequence of FIG. 1, or a sequence as depicted in the Examples below in which CR1 is deleted or essentially deleted. In another non-limiting embodiment, the LANA1 polypeptide comprises a LANA1 amino acid sequence in which a portion of CR1 of the LANA1 amino acid sequence is modified to decrease the ability of that portion of CR1 to inhibit a CTL immune response to LANA1. For example, the LANA1 amino acid sequence may be modified such that CR1 is substantially or completely deleted, that is, the LANA1 amino acid sequence comprises the amino acid sequence of FIG. 1 in which from about 50 to 107 amino acids of from amino acids 321-331 to from amino acids 427-428 are deleted or replaced in the LANA1 polypeptide. In another non-limiting embodiment, the LANA1 amino acid sequence comprises a LANA1 sequence in which at least about 50%-100%, e.g., 50%, 75%, 95% of CR1 and/or DEED (SEQ ID NO: 8) and DEEE (SEQ ID NO: 9) amino acid sequences are deleted. For abbreviation, an ieLANA1 in which CR1 is partially or wholly removed is referred to herein as a "deltaCR1 LANA1".

In a further embodiment of the methods of eliciting and/or increasing an immune response to KSHV LANA1 in a patient, the method comprises obtaining a cell from the patient, transforming the cell with a nucleic acid capable of expressing the immunologically-enhanced LANA1 polypeptide (e.g., deltaCR1 LANA1) in the cell, and transferring the transformed cell back into the patient thereby eliciting the immune response. The cell may be obtained from Peripheral Blood Lymphocytes or may be a dendritic cell. In an alternate embodiment, the polypeptide is administered parenterally to the patient with a pharmaceutically-acceptable excipient, such as an adjuvant.

In yet another embodiment of the method of eliciting and/or increasing an immune response to KSHV LANA1 in a patient, the method comprises transferring a nucleic acid comprising a gene into a cell of the patient, wherein the gene encodes and expresses an ieLANA1 polypeptide, such as a deltaCR1 LANA1 polypeptide. The nucleic acid may be transferred in vivo by, e.g., direct injection or viral-mediated transduction, in a pharmaceutically-acceptable carrier, optionally including an adjuvant, or ex vivo by, e.g., common transformation or transduction methods.

In a further embodiment of the method of eliciting and/or increasing an immune response to KSHV LANA1 in a patient, the method comprises introducing into the cells of the patient an ieLANA1 polypeptide, wherein the polypeptide comprises a LANA1 amino acid sequence comprising one or more LANA1 T-cell epitopes and a protein destabilization domain and the ieLANA1 polypeptide exhibits increased elicitation of a CTL immune response to wild-type LANA1 protein. Non-limiting examples of suitable protein destabilization domains include: D-Box, KEN, PEST, Cyclin A and UFD domain/substrate, attached to the LANA1 sequences (directly or indirectly through a linker or other intervening amino acid sequence) as is appropriate to obtain enhanced CTL response of the LANA1 sequences.

In another embodiment, an ieLANA1 polypeptide for eliciting a CTL immune response to LANA1 is provided. The LANA1 polypeptide comprises a LANA1 amino acid sequence (e.g., as shown in FIG. 1) comprising one or more LANA1 T-cell epitopes, wherein the LANA1 amino acid sequence is modified to exhibit increased elicitation of a CTL immune response as compared to wild-type LANA1 protein. Various non-limiting embodiments of the polypeptide are described above in connection with the methods, and/or are described throughout this document. In one non-limiting embodiment, the polypeptide is a deltaCR1 LANA1 polypeptide, so that the ieLANA1 polypeptide exhibits increased elicitation of a CTL immune response as compared to wild-type LANA1 protein. In another non-limiting embodiment, the ieANA1 polypeptide comprises a LANA1 amino acid sequence comprising one or more LANA1 T-cell epitopes and a protein destabilization domain and the ieLANA1 polypeptide elicits an increased CTL response as compared to wild-type LANA1 protein.

In another non-limiting embodiment, a polypeptide other than full-length LANA1 is provided that, comprising at the N-terminal or C-terminal end of the polypeptide, or inserted within the polypeptide an amino acid sequence obtained from or derived from a CR1 region of a LANA1 CR domain and having the capacity to inhibit a CTL immune response as compared to the same polypeptide without the amino acid sequence. In one example, the polypeptide comprises from amino acids 321-331 to from amino acids 427-428 of SEQ ID NO: 1 (FIG. 1). In another example, the polypeptide comprises 50 or more, or from about 50 to 107, consecutive amino acids of from amino acids 321-331 to from amino acids 427-428 of SEQ ID NO: 1. In one non-limiting embodiment, the polypeptide comprises from 50% to 100% of a LANA1 CR1 polypeptide. In another non-limiting embodiment, the polypeptide may comprise a derivative of the portion of a LANA1 CR domain having five or more iterations of one or both of the amino acid sequences DEED (SEQ ID NO: 8) and DEEE (SEQ ID NO: 9) or can be a polypeptide comprising from 50 to 107 consecutive amino acids comprising at least about 95%, 96%, 97% 98%, 99% or 100% iterations of one or both of the amino acid sequences DEED (SEQ ID NO: 8) and DEEE (SEQ ID NO: 9). The polypeptide also may comprise, without limitation, at least about 25 consecutive polypeptides from a glycine alanine (GA) repeat region of an EBV EBNA1 protein.

In yet another non-limiting embodiment, a method is provided of inhibiting proteasomal degradation of a polypeptide comprising attaching to the N-terminal or C-terminal end of the polypeptide an amino acid sequence obtained from or derived from a CR1 region of a LANA1 CR domain and having the capacity to inhibit elicitation of a CTL immune response as compared to the same polypeptide without the amino acid sequence. For example and without limitation, the polypeptide comprises from amino acids 321-331 to from amino acids 427-428 of (SEQ ID NO: 1) or the polypeptide may comprise at least about 50 consecutive amino acids of from amino acids 321-331 to from amino acids 427-428 of (SEQ ID NO: 1). Other useful embodiments of a polypeptide useful in this method are described in the preceding paragraph and throughout the present document.

Any of the polypeptides described herein may be prepared by gene expression (that is, recombinant methods). As such nucleic acids encoding and, optionally comprising a gene for expression any of the polypeptides described herein are provided. The nucleic acid optionally comprises vector sequences, such as viral vector sequences, for propagating the nucleic acid in a suitable host cell, for packaging the nucleic acid into a viral transducing particle and/or for otherwise facilitating transfer and propagation of the nucleic acid. In one non-limiting example, an isolated nucleic acid is provided comprising an open reading frame encoding a polypeptide other than full-length LANA1 protein, comprising at the N-terminal or C-terminal end of the polypeptide, or inserted within the polypeptide an amino acid sequence obtained from or derived from amino acids 321-331 to from amino acids 427-428 of (SEQ ID NO: 1). For example, the amino acid sequence may consist of 50 or more, e.g., from about 50 to 107, consecutive amino acids of from amino acids 321-331 to from amino acids 427-428 of (SEQ ID NO: 1). In one non-limiting embodiment, the polypeptide comprises from 50% to 100% of a LANA1 CR1 polypeptide and having the capacity to inhibit a CTL immune response to the polypeptide as compared to the same polypeptide without the amino acid sequence. The nucleic acid typically comprises a gene for expressing the open reading frame. The nucleic acid or gene may be contained in a vector and the vector may be a viral vector. In another non-limiting embodiment, the nucleic acid encodes an immunologically-enhanced LANA1 polypeptide for eliciting a CTL immune response to LANA1, as described above and throughout this document.

In the methods described herein, a polypeptide (for example and without limitation, a protein) or nucleic acid comprising a gene for expressing a protein as described herein may be contacted with a cell by any of a number of methods by which a CTL response can be generated. In one embodiment, a polypeptide or nucleic acid is injected parenterally in a patient (in vivo), for example and without limitation intramuscularly, in order to elicit an immune response to the injected polypeptide or protein product of the nucleic acid. In another example, cells from a patient, for example and without limitation, peripheral blood lymphocytes ("PBL") or dendritic cells ("DC"), are transformed or transduced ex vivo with the nucleic acid, optionally contained within a viral transducing particle, or a polypeptide is administered ex vivo to the cells. The cells would then be transferred back into the patient to elicit an immune response. In any case, for parenteral administration of any polypeptide or nucleic acid described herein, including proteins and transducing particles, the polypeptide or nucleic acid is administered in a composition comprising a pharmaceutically-acceptable carrier, optionally including an adjuvant.

Ideally, the immunogenically-enhanced LANA1 polypeptide comprises highly immunogenic domains of native LANA1 while lacking domains that would inhibit the efficacy of the ieLANA1. Unexpected results were obtained when the CR1 domain of LANA1 was deleted, as indicated in the example below.

BRIEF DESCRIPTION OF THE DRAWINGS

FIG. 1 provides an amino acid sequence of KSHV LANA1 (GenBank Accession No. AAC55944, SEQ ID NO: 1).

FIGS. 2A-2B provide a nucleotide sequence of KSHV LANA1 (GenBank Accession No. U52064, SEQ ID NO: 2).

FIG. 3 shows the overall structure of the KSHV LANA1 protein. Shown are the major domains of LANA1 together with known sites of interaction with cellular proteins and the viral replication origin. Used with permission from Lieberman, P. M., J. Hu, and R. Renne. 2006. KSHV and EBV Maintenance and Replication During Latency. In A. Arvin, A. Mocarski, P. S. Moore, B. Roizman, and R. J. Whitley (ed.), Human Herpesviruses: Biology, Therapy and Immunoprophylaxis, vol. in press. Cambridge University Press, Cambridge.

FIGS. 4A-4C provide a non-limiting list of human Class I MHC alleles.

FIG. 5. The CR domain of LANA1 inhibits LANA1 turnover. LANA1 deletion constructs of CR domains (LANAΔCR123) and each CR subdomain (LANAΔCR1, LANAΔCR2, LANAΔCR3) in the context of full-length LANA1 were fused to a PEST-sequence destabilized EGFP (d1EGFP) in the N-terminus and protein turnover rates were assessed by fluorescence. P value=0.0097 (d1EGFP and d1EGFP-LANA), 0.0101 (d1EGFP-LANA and d1EGFP-LANAΔCR123), 0.0199 (d1EGFP-LANA and d1EGFP-LANAΔCR2).

Figure 6:
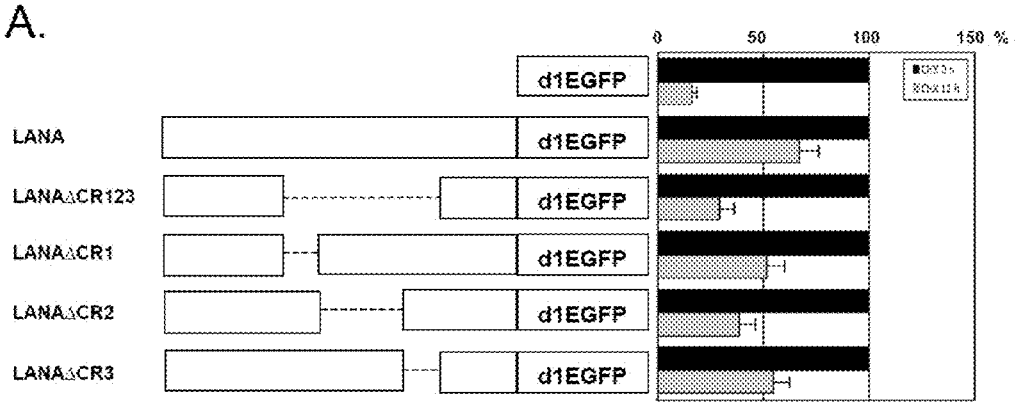
Figure 6:
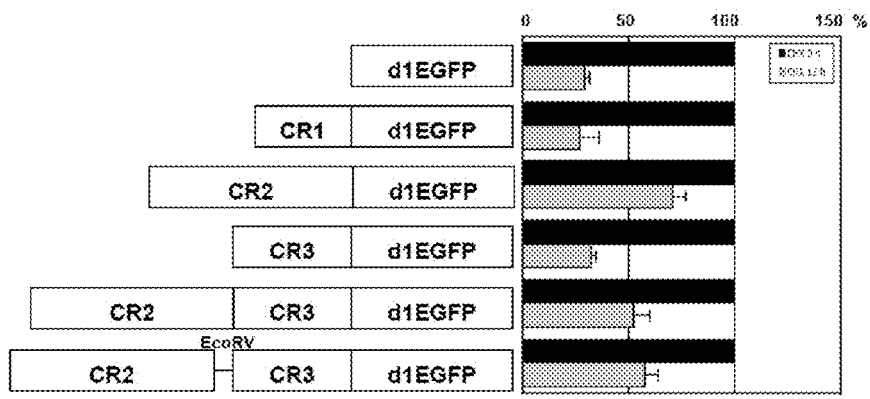

FIG. 6. CR 2 domain of LANA1 inhibits LANA1 turnover. (A) LANA1 repeat regions (CR1, CR2, CR3) were individually and in combination deleted from full-length LANA1, and cloned as fusion proteins with a destabilized enhanced green fluorescent protein (d1EGFP) (left panel) to ensure rapid proteasomal turnover. P value=0.007 (d1EGFP and LANAd1EGFP), 0.065 (LANAd1EGFP and LANAΔCR123d1EGFPd), 0.0225 (LANAd1EGFP and LANAΔCR2d1EGFP). (B) Turnover of individual LANA1 CR regions and subregions cloned into d1EGFP were also determined. P value=0.0441 (d1EGFP and CR2-d1EGFP), 0.022 (CR2-d1EGFP and CR1-d1EGFP), 0.0106 (CR2-d1EGFP and CR3-d1EGFP), 0.0325 (CR2-d1EGFP and CR2 CR3-d1EGFP). Normalized EGFP fluorescence at time 0 (A and B right panel, black bars) was used as a reference to compare EGFP fluorescence 12 hours after CHX treatment (grey bars) to assess protein turnover. Results are average values performed in triplicate from independent experiments. P values between different groups were obtained by two-tailed Student's t test using Prism software GraphPad).

Figure 7A:
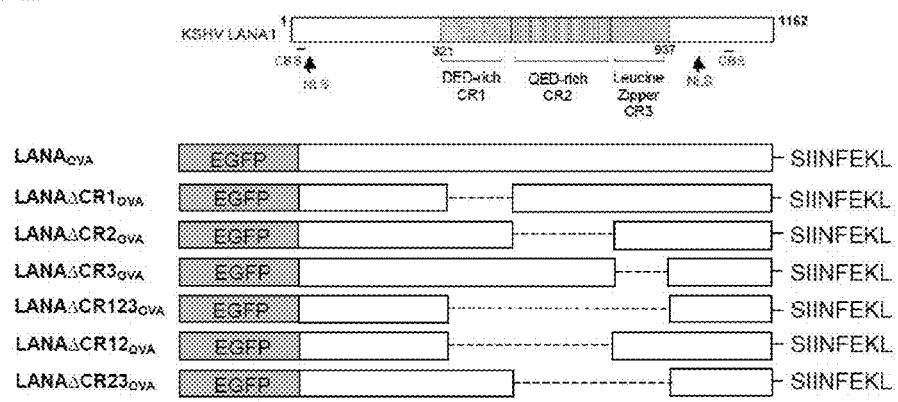
Figure 7A:
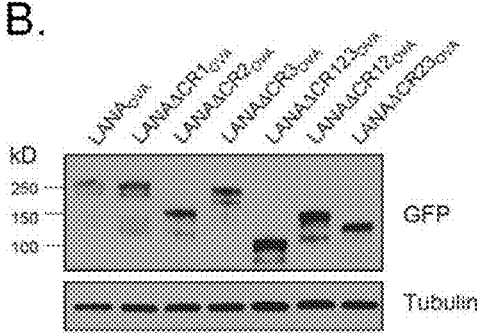
Figure 7A:
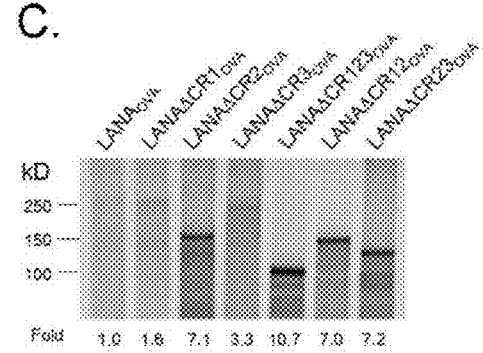
Figure 7B:
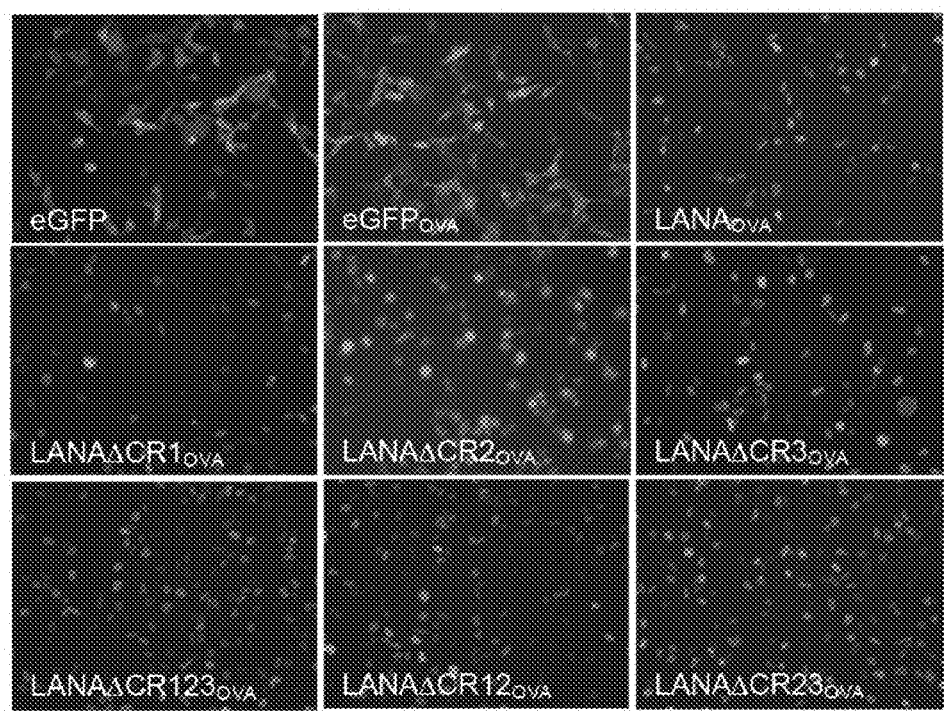

FIGS. 7A-7B. Construction and expression of EGFP-LANA$_{OVA}$. (7A-A) Schematic diagram of EGFP-LANA1$_{OVA}$ constructs used to measure SIINFEKL (SEQ ID NO: 3) antigen presentation. Protein expression was determined by immunoblotting (7A-B), in vitro translation labeled with [$^{35}$S]-Met (7A-C) and fluorescence of the EGFP-LANA1 fusion proteins (7B-D).

FIGS. 8A-8C. The CR1 region of LANA1 inhibits MHC I peptide antigen presentation in cis. (A) Representative results from flow cytometry analysis for SIINFEKL (SEQ ID NO: 3) presentation on 293KbC2 cells expressing EGFP-LANA1$_{OVA}$ constructs (FIG. 7A). Cells were stained with APC anti-mouse MHC class I Kb-SIINFEKL (25-D1.16, (SEQ ID NO: 3)) 24 h after transfection. Samples were gated for EGFP positivity to ensure construct expression and then the percentage SIINFEKL (SEQ ID NO: 3) presenting cells were determined by APC positivity. All experiments were repeated at least three times using either APC or Phycoerythrin (PE) 25-D1.16 (eBioscience) for detection and show similar results. (B) Quantitation of SIINFEKL (SEQ ID NO: 3) presentation from three independent experiments (mean±S.D.). P=0.0001 (EGFP and EGFP$_{OVA}$), 0.0023 (EGFP$_{OVA}$ and LANA$_{OVA}$), 0.0049 (LANA$_{OVA}$ and LANAΔCR1$_{OVA}$), 0.0135 (LANA$_{OVA}$ and LANAΔCR123$_{OVA}$), 0.0311 (LANA$_{OVA}$ and LANAΔCR12$_{OVA}$). P values between different groups were obtained by two-tailed Student's t test using Prism software (GraphPad). (C) The effect of different pretreatment conditions on antigen presentation. Cells were pretreated with rapamycin (autophagy inducer), Chloroquine (autophagy inhibitor), MG132 (proteasome inhibitor), interferon gamma (immunoproteasome inducer) and SIINFEKL (SEQ ID NO: 3) peptide presentation was determined by flow cytometry analysis.

Figure 9A:
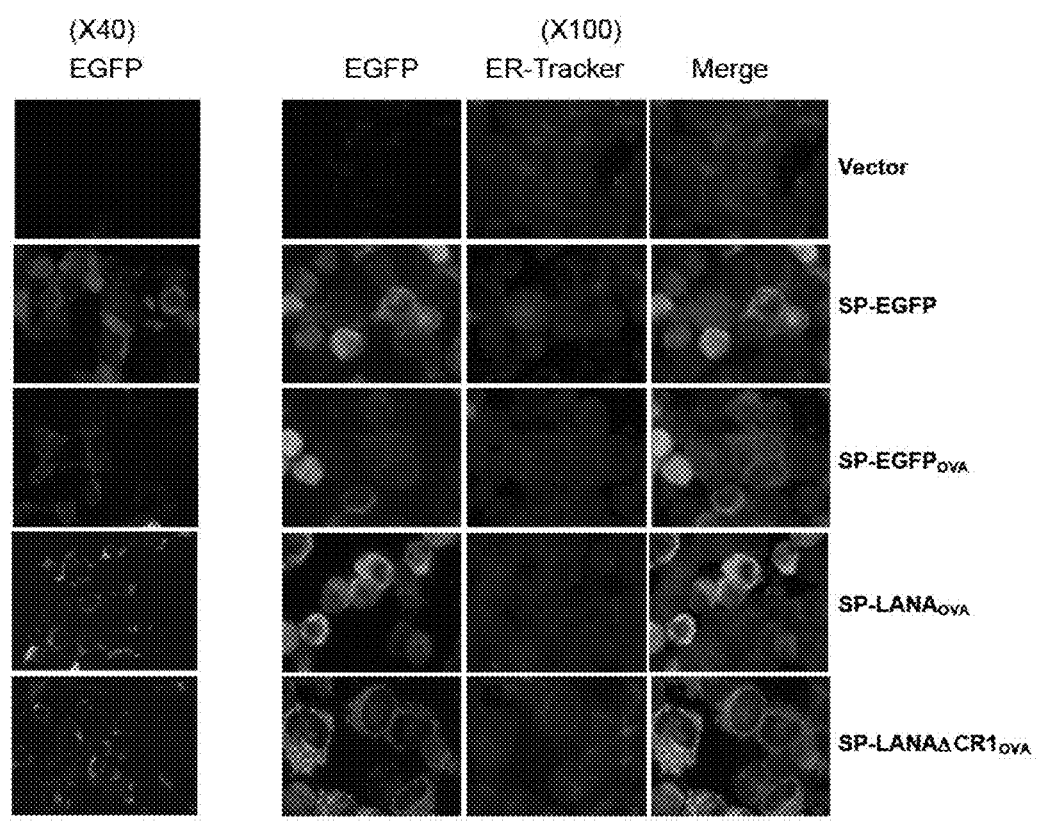
Figure 9B:
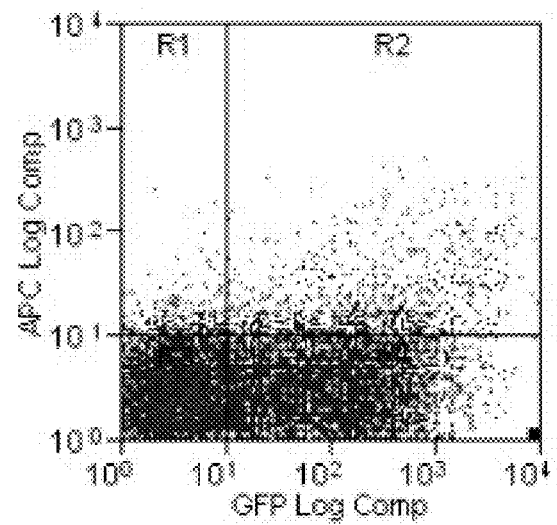
Figure 1:
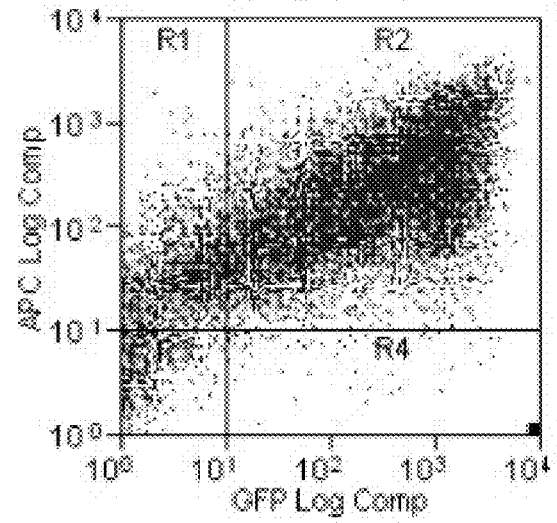
Figure 9B:
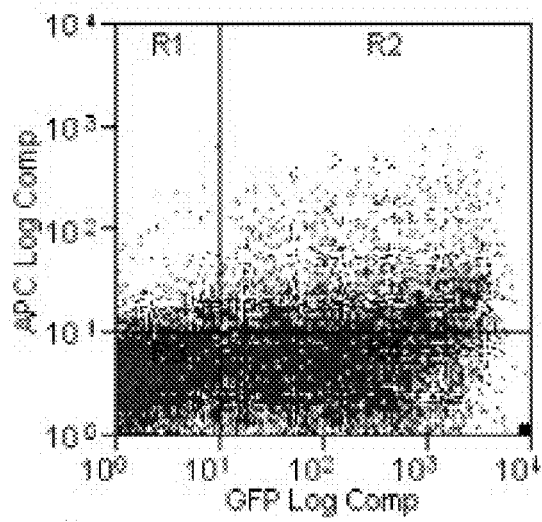
Figure 2:
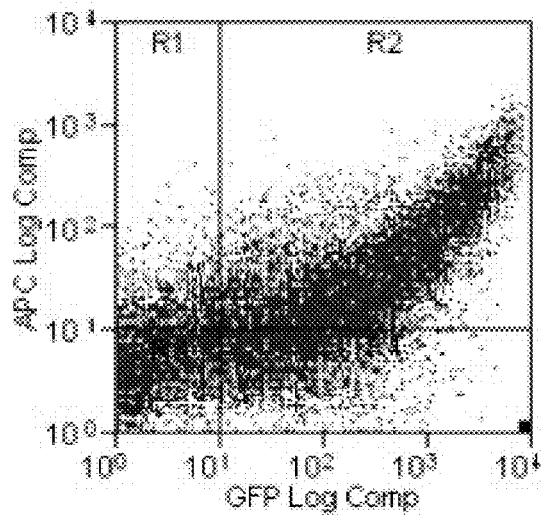
Figures 3, 9B:
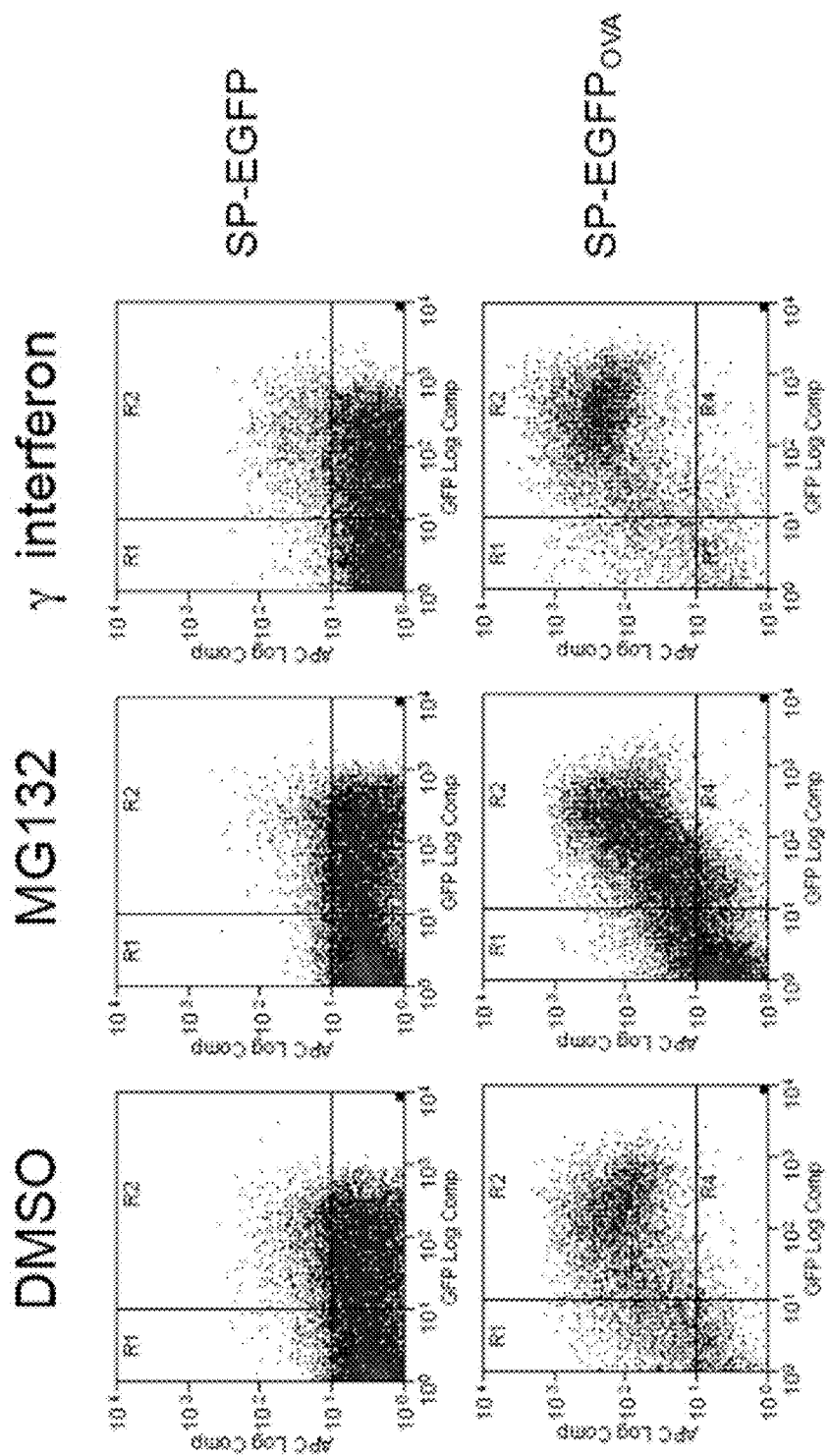
Figures 4, 9B:
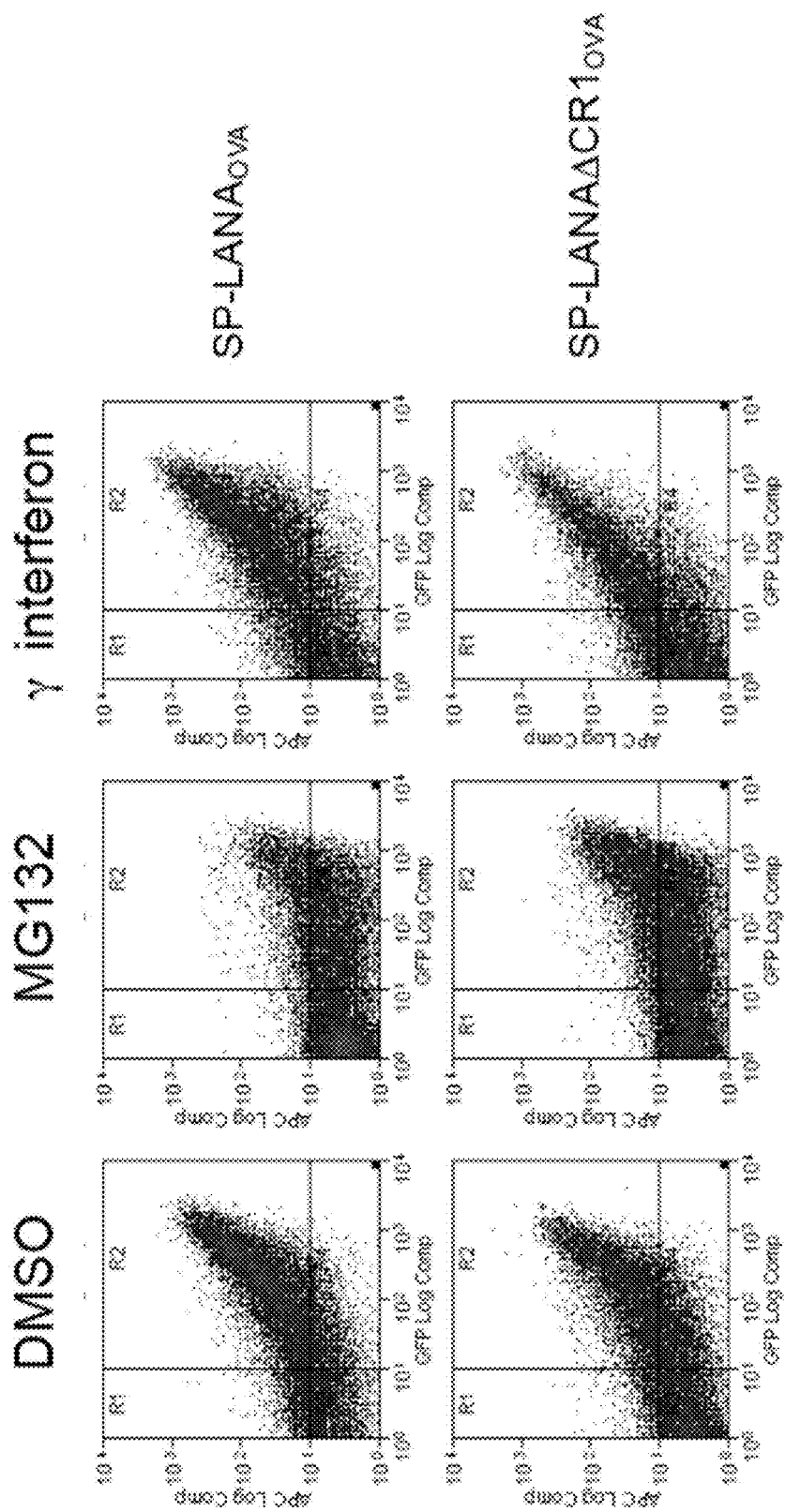

FIGS. 9A-9B. The Effect of endoplasmic reticulum (ER) targeting signal peptide (SP) on LANA1 antigen presentation. (A) LANA1 expression in ER was determined with EGFP (green) and ER-Tracker (red) fluorescence in living cells. The EGFP signal precisely overlapped with that of the ER-Tracker. (B) Flow cytometry analysis for SIINFEKL (SEQ ID NO: 3) presentation on 293KbC2 cells expressing either EGFP-LANA1$_{OVA}$ or SP-EGFP-LANA1$_{OVA}$ constructs with pretreatment of MG132 and interferon gamma.

Figure 10:
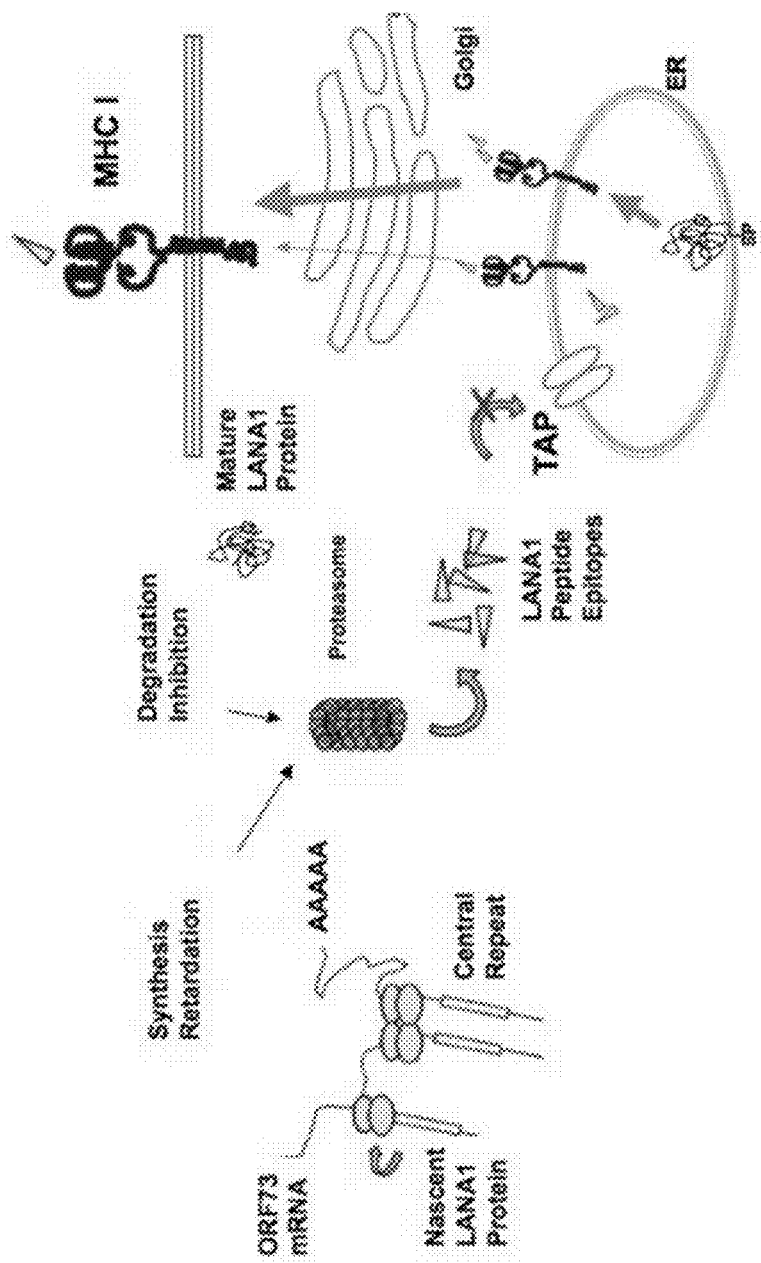

FIG. 10. Mechanism for CTL immune evasion by the DED-rich central repeat 1 (CR1) domain of LANA1. LANA1 repeat retards protein synthesis and inhibit degradation of mature LANA1 protein. LANA1 peptide processed by ubiquitin/proteasome dependent pathway can be presented to the cell surface through endoplasmic reticulum (ER) and golgi apparatus transports. TAP-independent processing (post-ER process) of LANA1 results from direct translocation of proteins into the ER lumen by signal peptide (SP) sensitizes LANA1 MHC class I antigen presentation. Although KSHV LANA1 has the same inhibitory function on translation and proteasomal processing as EBV EBNA1, LANA1, especially CR1 domain, has independent mechanism that it may affect on pre-ER processing such as peptide transport and peptide loading of MHC class I.

DETAILED DESCRIPTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values.

As indicated above, provided herein are: an immunogenic composition comprising immunologically-enhanced LANA1 (ieLANA1), a method of making an immunogenic composition comprising ieLANA1, a method of using an immunogenic composition comprising ieLANA1 to vaccinate an individual and a commercial kit for distributing an immunogenic composition comprising ieLANA1 in order to implement the described methods. Although described herein in the context of LANA1, the methods and compositions described herein are equally applicable to other proteins comprising synthesis retardation and/or degradation inhibitory sequences, including, without limitation, gammaherpesvirus latency proteins, such as, without limitation, EBV EBNA1.

As used herein, the term "vaccine" or other forms thereof refer to an immunogenic composition capable of eliciting an immune response to an antigen in a patient. The terms "vaccinate," "vaccination" or other forms thereof refer to the act of administering a vaccine to a patient in order to elicit an immune response to an antigen in the patient. As used herein, a vaccine can be a population of cells obtained from a patient, manipulated ex vivo and re-administered to the patient in order to elicit an immune response in the patient. In the methods described herein, a polypeptide (for example and without limitation, a protein) or nucleic acid comprising a gene for expressing a protein as described herein may be contacted with a cell by any of a number of methods by which a CTL response can be generated. In one embodiment, a polypeptide or nucleic acid is injected parenterally in a patient (in vivo), for example and without limitation intramuscularly, in order to elicit an immune response to the injected polypeptide or protein product of the nucleic acid. In another example, cells from a patient, for example and without limitation, peripheral blood lymphocytes (PBL) or dendritic cells (DC), are transformed or transduced ex vivo with the nucleic acid, optionally contained within a viral transducing particle, or a polypeptide is administered ex vivo to the cells. The cells would then be transferred back into the patient to elicit an immune response.

A "patient" refers to a live subject, such as a human subject or an animal subject. A vaccine may be administered for any number of reasons, including, without limitation, to elicit protective immunity (partial or complete, humoral or cellular) or to induce a specific immune cell population for, without limitation, research purposes or for commercial purposes, such as, without limitation, to study the effect of such immunization, to produce specific cell populations in a patient, to produce cell products, including, without limitation, effectors (such as, without limitation, antibodies and cytokines) and other uses. Cell populations and cell products may be used, for example and without limitation, in diagnostic assays, in research or therapeutically, such as, without limitation, in adoptive transfer of cells. Uses or cells or cell products may be syngeneic (including self), allogeneic or xenogeneic.

The term "comprising" in reference to a given element of a method, composition, apparatus, etc., means that the method, composition or apparatus includes that element, but also may contain other non-specified elements. "A" or "an" refer to one or more.

LANA1 (in one embodiment, Genbank Accession Nos. AAC55944 (SEQ ID NO: 1, protein) and U52064 (SEQ ID NO: 2, nucleotide), FIGS. 1 and 2, respectively, is one of a few KSHV proteins obligatorily expressed during latent replication. Amino acid residue numbering for LANA1, unless stated otherwise, is in reference to the amino acid sequence provided in FIG. 1 (SEQ ID NO: 1). LANA1 has basic N-terminal (amino acids 1-329) and C-terminal (amino acids 915-1162) domains and an acidic central repeat domain. The central repeat domain can be further divided into three regions, from N- to C-terminal direction: a DED-rich region (amino acids 330-428), a Q-rich region (amino acids 442-767) and a Leucine zipper region (amino acids 769-914).

Provided therefore, according to one embodiment, is an immunogenically-enhanced LANA1 protein (ieLANA1) in which a portion of the central repeat domain is modified to increase the ability of the protein to elicit a CTL response against LANA1, and thus latent and active KSHV infections. Removal of a sufficient number of amino acid residues from the LANA1 CR1 region to increase proteasomal degradation of LANA1 would produce an ieLANA1 protein. By "immunogenically-enhanced," it is meant that the ieLANA1 protein elicits (is capable of eliciting) an increased CTL immune response as compared to wild-type (wt) LANA1 protein, without any intent to be bound by this theory, by virtue of increased presentation by Class 1 MHC chaperones. The LANA1 protein is immunogenically-enhanced by removal of or modification of substantially all of the central repeat (CR) domain, CR1, or enough of the CR1 domain to increase the ability of the protein to elicit a CTL response against LANA1 as compared to wt LANA1.

CR1, as shown in FIG. 1, consists of an amino acid sequence that is highly enriched for "D" (aspartic acid, Asp) and "E" (glutamic acid, Glu) residues, including multiple iterations of certain 4 amino acid motifs, DEEE (SEQ ID NO: 8) and DEED (SEQ ID NO: 9), between amino acid residues 321 and 428 of LANA1 (SEQ ID NO: 1). The iterative nature of these repeats indicates that the identity of the sequences of CR1 to be removed is of less importance than removing or otherwise mutating a critical number of the repeats to achieve the goal of enhancing immunogenicity. A person of ordinary skill can determine the percentage of these repeats.

In one embodiment, the ieLANA1 protein comprises a polypeptide comprising the N-terminal and C-terminal regions of LANA1, in which the central repeat region or CR1 is completely or substantially deleted so as to decrease degradation inhibition and/or synthesis retardation attributable to sequences of the central repeat domain. In another non-limiting embodiment, the ieLANA1 protein comprises amino acids 1-321 or 1-330 of LANA1 (SEQ ID NO: 1) attached directly to amino acids 429-1162 or 939-1162 of SEQ ID NO: 1. In a further embodiment, the ieLANA1 is a polypeptide comprising nine or more consecutive amino acids of a LANA1 protein comprising an MHC Class I antigen, wherein the polypeptide excludes CR1 or the motifs: DEED (SEQ ID NO: 8) and/or DEEE (SEQ ID NO: 9).

As used herein, in the context of an ieLANA1 polypeptide for eliciting or increasing a CTL immune response to LANA1, comprising a LANA1 amino acid sequence comprising one or more LANA1 T-cell epitopes, the phrase "wherein the polypeptide does not comprise a portion of a LANA1 CR1 having the capacity to inhibit CTL immune response means enhanced LANA1 polypeptide elicits increased CTL response as compared to wild-type LANA1 protein" means that the polypeptide contains one or more Class I MHC epitopes of LANA1, but all or a portion of the central repeat domain CR1 is removed or otherwise modified to elicit increased CTL response as compared to wild-type LANA1 protein. This does not necessarily mean that all CR1 sequences are removed, but either: 1) all sequences that contribute to the reduction of CTL response are removed or 2) some sequences that contribute to the reduction of CTL response are removed, leaving some sequences in the polypeptide that retain that capacity. A protein sequence can be "removed," by modification, such as by deletion of amino acids, substitution of amino acids and/or insertion of amino acids that disrupt the relevant function, that is, in the context of the present disclosure, a CTL immune response. LANA1 T-cell epitopes are, according to certain non-limiting embodiments of the methods and compositions described herein, portions of LANA1 amino acid sequence that do not include CR domain amino acid sequences, and in one embodiment do not comprises CR1 amino acid sequences.

An "MHC Class I antigen" is a polypeptide that is capable of eliciting a Cytotoxic T-Lymphocyte (CTL) immune response and which comprises an agretope (that part of a processed antigen that binds to the MHC molecule) and an epitope (that part of a processed antigen that binds to a T Cell receptor). In one non-limiting embodiment, the polypeptide is a nonamer that does not require proteasome digestion. In another non-limiting embodiment, the polypeptide is proteasomally-digestible, meaning that it is digestible by a proteasome to produce an MHC Class I antigen. In any case, whether the polypeptide is an MHC Class I antigen or requires proteasomal digestion to yield an MHC Class I antigen, it is useful in eliciting a CTL response by yielding an MHC Class I antigen that can be presented on the surface of a cell.

Figures 4, 8C:
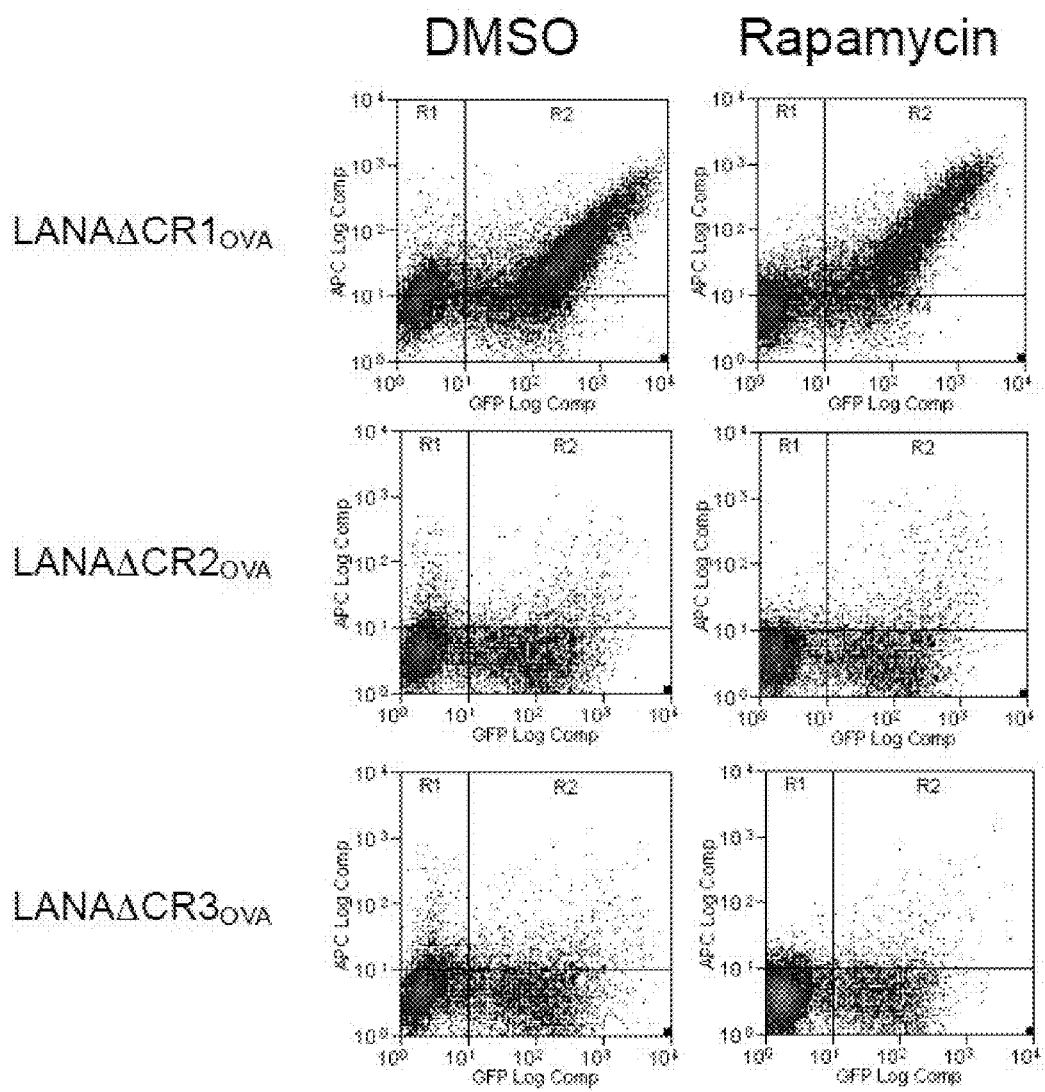
Figures 5, 8C:
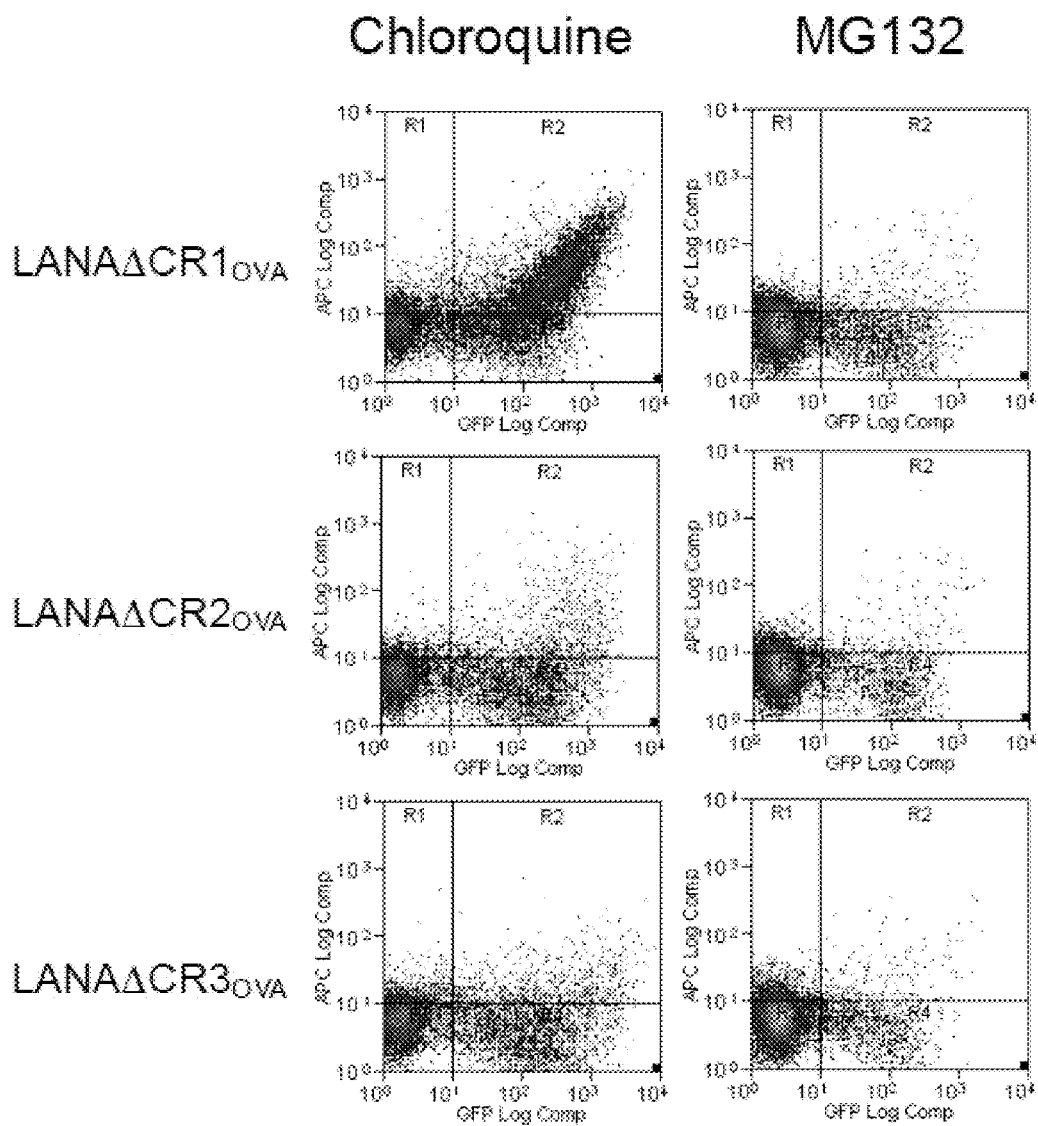
Figures 6, 8C:
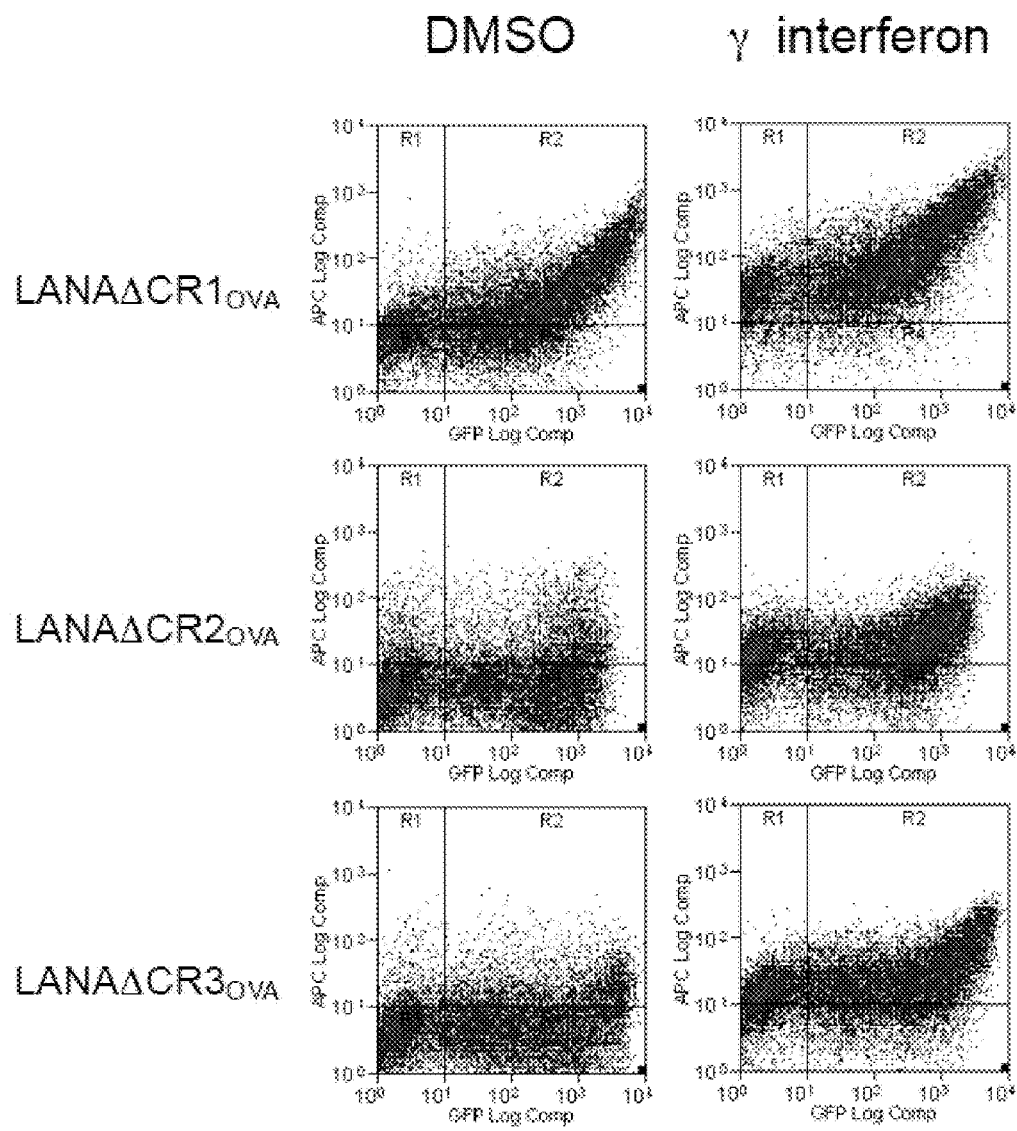
Figures 7, 8C:
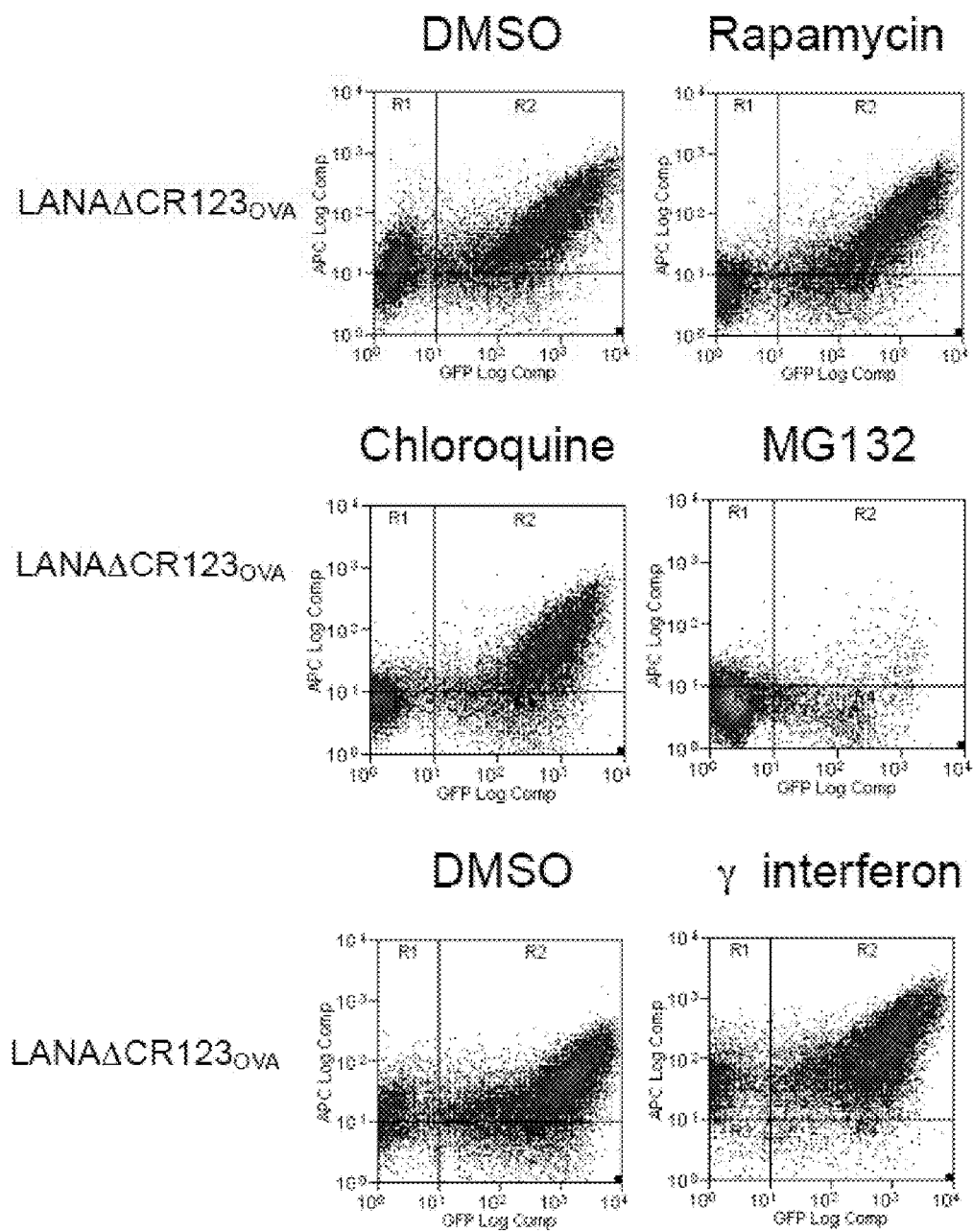

MHC Class I antigens may be determined readily by a person of ordinary skill in the art by using predictive algorithms, for example and without limitation, RANKPEP or the SYFPEITHI database (both of which are available on-line). Such predictive algorithms are capable of identifying determinants in the context of many MHC Class I alleles, such as, without limitation, HLA-A0201 (HLA-A2). A large number of MHC class I alleles other than HLA-A0201 also have been identified. Non-limiting examples of MHC class I HLA-A or HLA-B alleles are identified, for example and without limitation, those identified in FIG. 4 (Anthony Nolan, London). More common Class I MHC alleles include, without limitation: HLA-A1, HLA-A2, HLA-A3, HLA-B7 and HLA-B44. LANA1 Class I MHC antigens (determinants) can be identified for a huge variety or MHC alleles using any of a number of commercially-available software programs, such as those described above, and their determination is well within the ability of those of ordinary skill in the art. Strings of one or more LANA1 Class I MHC antigens may be strung together in a contiguous engineered polypeptide. The engineered polypeptide may comprise an "epitope string", an amino acid sequence that contains two or more iterations of any given antigen/epitope, with the object of increasing an immune response to that antigen, for example and without limitation, when that antigen includes a sub-dominant epitope.

One embodiment of the present invention provides a polypeptide capable of eliciting an enhanced CTL response as compared to wild-type LANA1 administered in the same manner. To achieve this, the polypeptide comprises one or more LANA1 MHC Class I antigens (antigenic amino acid sequences that are presentable by class I MHC molecules). The polypeptide, if requiring proteasomal degradation prior to association with Class I MHC, contains proteasomal target residues flanking the antigen and is therefore "preoteasomally digestible." Certain sequences present in the central repeat domain of LANA1 contribute to resistance to proteasomal degradation of the native LANA1 polypeptide. In order to obtain an ieLANA1, the CR1 central repeat domain, or a portion thereof able to inhibit CTL responsiveness, as compared to wild-type LANA1 is removed to increase proteasomal degradation. As shown below, the exact residues responsible for the decreased ability of LANA1 to elicit a CTL immune response are predominantly present within the CR1 portion of the central repeat domain and can be identified quite readily.

As will be recognized by those of ordinary skill in the arts, production of polypeptides can be accomplished by a variety of methods. Thus, any polypeptide described herein can be prepared and purified according to any one of those methods. Cell-free transcription and translation methods are on method of generating small quantities of polypeptides, and smaller polypeptides (generally less than 100 amino acids in length) can be produced by synthetic methods. Larger polypeptides and larger quantities are best produced by one of the many bacterial, yeast, mammalian cell, or insect cell systems available commercially. In many instances a yeast-based expression system is used to prepare larger quantities of protein, for example, the PichiaPink™ Yeast Expression System, Invitrogen, Carlsbad, Calif., see, e.g., PichiaPink™ Yeast Expression System User Manual (Aug. 6, 2010)). Companies, such as GenScript USA, Inc, Piscataway, N.J., can be employed to produce optimized vector systems and scale-ups to produce commercial grade and quantity of a desired protein.

In one non-limiting embodiment of the present invention, an ieLANA1 polypeptide is used in a method to elicit a CTL response against LANA1 in a subject, such as a human patient. To successfully elicit (raise) such an immune response, an MHC Class I antigen must be presented by a cell by a class I MHC molecule. In order to do so, the ieLANA1 polypeptide must be introduced into a cell for appropriate processing. By "introduced" it is meant physical introduction of a protein or introduction of a gene into a cell for production of the protein to be introduced. In one embodiment, and perhaps the simplest and safest method, cells, for example and without limitation, peripheral blood lymphocytes (PBLs) or Dendritic Cells (DCs) are obtained from a patient. A gene for expression of the LANA1 polypeptide in lymphocytes is transferred into the cells ex vivo and the cells are transferred back into the patient. In the patient, the cells express the ieLANA1, which is capable of eliciting a CTL response against LANA1 in the patient, thereby eradicating any cells expressing either LANA1 or ieLANA1. Viral vectors or other vectors can be used to transfer a gene in vivo, but the described ex vivo method may be preferred as a method to better control cell transformation and reduce any risk arising from the transfer of recombinant virus directly to a patient, typically by a parenteral route. In vitro or ex vivo, a gene can be transferred into a cell by a number of common methods, including without limitation: viral transduction using a recombinant viral vector incorporated into a viral transducing particle, such as a recombinant Adenovirus, Adeno-associated virus, vaccine virus or retrovirus, among others; liposome transfer; electroporation; particle bombardment and calcium phosphate precipitation. In vivo transfer of genetic material to cells can be accomplished using naked DNA, viral transducing particles and liposome preparation as described above and in the art. The in vivo route of delivery can vary so long as an immune response can be generated. It may be preferred to inject DNA, viral transducing particles or liposome preparations locally, such as intramuscularly, to minimize broad dissemination of the injected material.

In one embodiment, an ieLANA1 protein or a nucleic acid containing a gene encoding the protein can be administered parenterally, such as, without limitation, intramuscularly or subcutaneously, in order to elicit a CTL response against LANA1. In this method, an ieLANA1 is administered in a pharmaceutically-acceptable carrier, which can include an adjuvant and other suitable carriers. The composition administered parenterally comprises an carrier which comprises acceptable excipients, such as, without limitation, one or more suitable: vehicle(s), solvent(s), diluent(s), pH modifier(s), buffer(s), salt(s), colorant(s), rheology modifier(s), lubricant(s), filler(s), antifoaming agent(s), erodeable polymer(s), hydrogel(s), surfactant(s), emulsifier(s), adjuvant(s), preservative(s), phospholipid(s), fatty acid(s), mono-, di- and tri-glyceride(s) and derivatives thereof, wax(es), oil(s) and water, as are broadly known in the pharmaceutical arts. In one embodiment, the carrier is water, in another normal saline and in yet another, phosphate-buffered saline. Adjuvants include, without limitation, Freund's Complete Adjuvant (FCA), Freund's Incomplete Adjuvant (FIA), Montanide ISA Adjuvants (Seppic, Paris, France), Ribi's Adjuvants (Ribi ImmunoChem Research, Inc., Hamilton, Mont.), Gerbu Adjuvant (Gerbu Biotechnik GmbH, Gaiberg, Germany/C-C Biotech, Poway, Calif.), Hunter's TiterMax (CytRx Corp., Norcross, Ga.), aluminum salt adjuvants (typically aluminum phosphate or aluminum hydroxide) and nitrocellulose-adsorbed protein.

Irrespective of the method and route of delivery, the treatments are administered as many times, over intervals and for a duration effective to elicit a CTL response against LANA1. In the case of the ex vivo methods, cells transfected, transduced or transformed with a gene for expressing ieLANA1 can be administered intravenously over a time period of minutes, hours, days, etc. The entire batch of cells can be administered to a patient as a single bolus, or in multiple doses over hours, days or weeks. Likewise, cells expressing ieLANA1 can be administered parenterally by routes other than intravenous in any effective dosage regimen.

In one embodiment, an amino acid sequence obtained from or derived from a CR1 region and/or a junction therebetween, of a LANA1 central repeat domain and having the capacity to decrease CTL response to a polypeptide in which the amino acid sequence is inserted as compared to the same polypeptide without the amino acid sequence is provided. That amino acid sequence may be used to alter (e.g., decrease) the CTL immunogenicity of a chimeric protein comprising the LANA1 CR1 sequence attached to a second polypeptide. Such a chimeric polypeptide had a multitude of uses, including, without limitation, production of recombinant proteins that are less immunogenic. In one non-limiting embodiment, that amino acid sequence comprises 25 or more consecutive amino acids of amino acids 321-428 of FIG. 1. In another embodiment, the amino acid sequence comprises from about 25 to 107 consecutive amino acids of amino acids 330-428 of FIG. 1. In another embodiment, a chimeric protein with increased resistance to proteasomal degradation comprises at its N-terminus, C-terminus or internally five or more iterations, e.g., 10-25 iterations, of one or both of the motifs DEED (SEQ ID NO: 8) or DEEE (SEQ ID NO: 8), though the portion may consist of more than 107 amino acids, for example 110, 125, 150, 175, 200, 225, 250, 275, 300, 325 and 350 amino acids consisting of at least about 95% of the motifs (4-mer amino acid sequences) DEED (SEQ ID NO: 8) and/or DEEE (SEQ ID NO: 9).

In yet another embodiment, the polypeptide comprises a sequence having the structure N-A-C, in which A comprises at least 25 contiguous amino acids of residues 321-428 of FIG. 1, or five or more iterations, e.g., 10-25 iterations, of one or both of the motifs DEED (SEQ ID NO: 8) or DEEE (SEQ ID NO: 9), though the portion may consist of more than 107 amino acids, for example 110, 125, 150, 175, 200, 225, 250, 275, 300, 325 and 350 amino acids consisting of at least about 95% of the motifs (4-mer amino acid sequences) DEED (SEQ ID NO: 8) and/or DEEE (SEQ ID NO: 9). "N" and "C" refer to the N-terminus and C-terminus, respectively, or a polypeptide.

In one embodiment, a nucleic acid containing a sequence, such as an open reading frame (ORF), encoding an ieLANA1 polypeptide is provided. In one embodiment, a nucleic acid sequence encoding any of the above-described ieLANA1 polypeptides is incorporated into a gene for expressing that ieLANA1 polypeptide. In another, a nucleotide sequence encoding a CTL response-inhibitory polypeptide sequence, as described above, is attached, in-frame, with a nucleic acid encoding a protein to produce an ORF encoding a protein with decreased ability to elicit a CTL response. Non-limiting examples of candidates for proteins that could benefit from addition of a proteasome-degradation-inhibitory polypeptide sequence include indicator proteins, such as GFP, enzymes, particularly enzymes for use in vivo, such as, without limitation, adenosine deaminase to treat severe-combined immunodeficiency (SCID) (Mortellaro A, et al. Ex vivo gene therapy with lentiviral vectors rescues adenosine deaminase (ADA)-deficient mice and corrects their immune and metabolic defects. Blood. 2006 Jul. 11; Miseki T, et al. Suppression of tumor growth by intra-muscular transfer of naked DNA encoding adrenomedullin antagonist. Cancer Gene Ther. 2006 Jul. 14; Ponder K P. Gene therapy for hemophilia. Curr Opin Hematol. 2006 September; 13(5):301-7. PMID: 16888433 and Herrera J L, et al. Protective Role for Plasmid DNA-Mediated VIP Gene Transfer in Non-Obese Diabetic Mice. Ann N Y Acad. Sci. 2006 July; 1070:337-41). As described above, the proteasome-degradation-inhibitory polypeptide sequences can be attached to the N- or C-terminus of the protein, or even internally, so as to best retain the structure or function of the protein. Vectors containing expression cassettes are broadly available for expression of genes in various host cells, such as E. coli, S. cerevisiae, insect and mammalian cells, such as Chinese Hamster Ovary (CHO) cells or human cells. Although DNA consisting only of a gene for expressing a recombinant protein (an ieLANA1 or a protein containing a proteasome-degradation-inhibitory polypeptide sequence) can be used to transfect or transform a cell, a huge number of vector and transformation systems, many of which are well-known and beyond the scope of this disclosure, are useful in producing a cell that expresses a recombinant protein. Some of these vector systems are known, including, without limitation: yeast, insect, bacterial, mammalian and viral (for example, phage, retroviral, Adenoviral, and Adeno-associated virus) vector systems. Suitable vectors, cells and, in general, expression systems are available commercially from a large variety of sources, including without limitation, Stratagene of La Jolla, Calif. and the American Type Culture Collection (ATCC) of Manassass, Va. In another non-limiting example, plasmid- or episome-based systems useful in gene transfer and expression are broadly known. Any gene for expression of a given ieLANA1 polypeptide or protein containing a proteasome-degradation-inhibitory polypeptide sequence can be inserted into a suitable vector for transfer and expression in a cell.

By "expression" it is meant the overall flow of information from a gene (without limitation, a functional genetic unit for producing a gene product in a cell or other expression system encoded on a nucleic acid and comprising: a transcriptional promoter and other cis-acting elements, such as response elements and/or enhancers; an expressed sequence that typically encodes a protein (open-reading frame or ORF) or functional/structural RNA, and a polyadenylation sequence), to produce a gene product (typically a protein, optionally post-translationally modified or a functional/structural RNA). By "expression of genes under transcriptional control of," or alternately "subject to control by," a designated sequence, it is meant gene expression from a gene containing the designated sequence operably linked (functionally attached, typically in cis) to the gene. The designated sequence may be all or part of the transcriptional elements (without limitation, promoters, enhancers and response elements), and may wholly or partially regulate and/or affect transcription of a gene. A "gene for expression of" a stated gene product is a gene capable of expressing that stated gene product when placed in a suitable environment—that is, for example, when transformed, transfected, transduced, etc. into a cell, and subjected to suitable conditions for expression. In the case of a constitutive promoter "suitable conditions" means that the gene typically need only be introduced into a host cell. In the case of an inducible promoter, "suitable conditions" means when an amount of the respective inducer is administered to the expression system (e.g., cell) effective to cause expression of the gene.

Any nucleic acid encoding a given polypeptide sequence can be prepared by a variety of known methods. For example and without limitation, by direct synthesis of the primary DNA sequence for insertion in a gene, gene cassette, vector, etc., by PCR cloning methods, or by restriction and ligation or recombination according to extremely well-established practices. In the case of preparation of a nucleic acid sequence encoding a repetitive sequence, a nucleic acid encoding a single iteration of the repeat may be prepared with blunt or sticky ends, as is known in the art, and subsequently ligated to form multiple iterations. The ligated iterative sequences can then be ligated into a vector, gene or gene cassette by known methods. One example of such a single iteration is a sequence encoding the sequences DEED (SEQ ID NO: 8) and/or DEEE (SEQ ID NO: 9).

With regard to the ieLANA1 polypeptide, and in the context of the methods, compositions, polypeptide sequences and nucleic acid sequences, and other embodiments thereof described herein, a LANA1 polypeptide attached, in-frame to (fused with) a protein destabilization sequence is likely to be useful in enhancing CTL response to the LANA1 polypeptide. While the glycine-alanine repeat ("GAr") motif inhibits proteasomal processing of EBNA1, this can be overcome through the introduction of strong destabilizing motifs that enforce turnover of EBNA1 heterologous proteins possessing a GAr stabilization domain (Dantuma, N. P., et al. 2000 Inhibition of proteasomal degradation by the Gly-Ala repeat of Epstein-Barr virus is influenced by the length of the repeat and the strength of the degradation signal. *Proc Natl Acad Sci USA* 97:8381-5). As used herein, a "protein destabilization sequence" is a polypeptide sequence that, when fused (attached in-frame either directly or through an intervening sequence, such as a linker sequence) to LANA1 or a portion thereof, or another protein, will contribute to increased proteasomal degradation of that protein as compared to that same protein without the same destabilization sequence. LANA1 or a portion thereof fused to a protein destabilization sequence are useful in the methods described herein and therefore provided are methods of eliciting immune response to LANA1 comprising introducing into a cell of a subject LANA1 or a portion thereof which is fused to a destabilization sequence. As follows, also provided are polypeptides comprising a LANA1-protein destabilization sequence as well as nucleic acids encoding a LANA1-protein destabilization sequence polypeptide and compositions comprising either. In one embodiment, full-length LANA1 is fused to a protein destabilization domain. In another embodiment, from about 50 to 1161 contiguous amino acids, and integers therebetween of LANA1 are fused to a protein destabilization sequence.

There are several strategies to destabilize proteins to enforce their rapid proteasomal turnover. Cell cycle-dependent proteins must undergo rapid and complete ubiquitin-mediated proteolysis to achieve cycling within the cell cycle. Primary structural domains, including, without limitation, the nine residue D-box (Yamano, H., et al. 1998. The role of the destruction box and its neighbouring lysine residues in cyclin B for anaphase ubiquitin-dependent proteolysis in fission yeast: defining the D-box receptor. Embo J 17:5670-8), the KEN box (Pfleger, C. M., et al. 2000. The KEN box: an APC recognition signal distinct from the D box targeted by Cdh1. Genes Dev 14:655-65), A-box (Nguyen, H. G, et al. 2005. Mechanism of Aurora-B degradation and its dependency on intact KEN and A-boxes: identification of an aneuploidy-promoting property. Mol Cell Biol 25:4977-92) and PEST domains (Fung, T. K., et al. 2002. Cyclin F is degraded during G2-M by mechanisms fundamentally different from other cyclins. J Biol Chem 277:35140-9) have been used in heterologous fusion proteins to initiate rapid protein degradation. Cloning D-box/KEN domains into LANA1 will cause the fusion protein to become an anaphase-promoting complex/cyclosome (APC) E3 ligase target that should result in its rapid turnover. N-end rule proteins (containing an N-end rule substrate or N-degron) and ubiquitin-fusion degradation (UFD) proteins are rapidly processed for proteasomal destruction (Dantuma, N. P., et al. 2000. Short-lived green fluorescent proteins for quantifying ubiquitin/proteasome-dependent proteolysis in living cells. Nat Biotechnol 18:538-43 and Varshaysky, A. 1996. The N-end rule: functions, mysteries, uses. Proc Natl Acad Sci USA 93:12142-9).

In one embodiment, LANA1 or other polypeptides may be destabilized by cloning the N-terminal destruction region of cyclin A in-frame into LANA1 (Kaspar, M., et al. 2001. Mitotic degradation of cyclin A is mediated by multiple and novel destruction signals. Curr Biol 11:685-90). This is a simple modification that encodes multiple destruction sequences, and has been successful in initiating rapid degradation in a variety of proteins that have been modified. It is anticipated that the cyclin A-LANA1 fusion protein will undergo rapid proteolytic degradation that can be determined through the kinetics of [$^{35}$S]-methionine pulse-chase labeling and immunoprecipitation after transfection into 293 cells.

In another embodiment, as an alternative approach, a UFD substrate containing an N-terminal Ub-R fusion with linker sequence and lysine residue at position 17 can be engineered. This substrate has been shown to be a potent and nonspecific activator of proteasomal degradation (Dantuma, N. P., et al. 2000. Nat Biotechnol 18:538-43) and may be fused to the N-terminus of a LANA1 polypeptide.

In yet another embodiment of the ieLANA1 polypeptide fused with a destabilization sequence, and in the context of the methods, compositions, polypeptide sequences and nucleic acid sequences, and other embodiments thereof described herein, either a dibasic endopeptidase recognition site or a caspase-recognition site can be engineered on either side of the DI domain. In doing so, it is anticipated that the LANA1 protein will be cleaved after transfection into 293 cells, leading to rapid degradation of fragments. The cleavage product(s) lacking the DI domain should undergo rapid proteolysis.

By fusing a protein destabilization sequence, such as, without limitation, D-Box, KEN, PEST, Cyclin A and UFD domains/substrates, to a LANA1 polypeptide, it is expected that LANA1 will be destabilized Immunoblotting in the presence of proteasome inhibitors may be performed to investigate the mechanism of LANA1 degradation-inhibition. It is assumed that this will generate a polyubiquitinylated protein ladder for the LANA1 fusion protein but not for wild-type LANA1 if the DI domain inhibits ubiquitinylation. If the DI acts to inhibit proteasomal processing downstream from the ubiquitinylation step (such as by preventing proteasomal unfoldase activity), no change in polyubiquitinylation profiles are expected to be seen when cells transfected with the two LANA proteins are treated with proteasome inhibitors. Thus, either through use of destabilizing destruction domains or through endogenous proteolytic cleavage of LANA1, it is anticipated that it will be possible to generate a version of LANA1 protein that is rapidly processed through the cellular proteasome system.

EXAMPLES

Examples 1-15 presented in U.S. patent application Ser. Nos. 13/221,040, 12/191,698, and 60/955,898, to which the present application claims priority are incorporated herein by reference. Examples are provided as non-limiting examples and illustrations of the matter described and claimed herein.

Example 1

Materials and Methods
Plasmids

Figures 4C, 5:
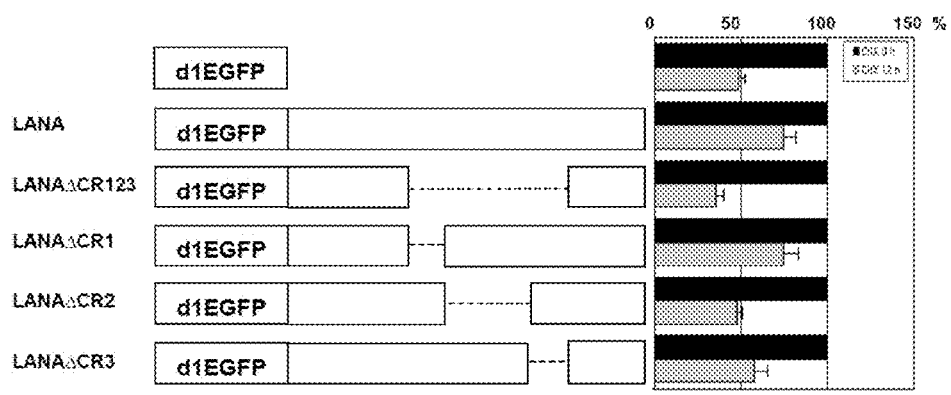

LANA1 full-length/deletion and the central repeat sub-domain (CR1, CR2, CR3 or CR2/CR3) containing constructs were generated by PCR with a BC-1 DNA template and fused to EcoRI/HindIII sites of pd1EGFP-N1 encoding a destabilized EGFP in the C-terminus as described previously (Kwun, H. J., et al., 2007. Kaposi's Sarcoma-Associated Herpesvirus Latency-Associated Nuclear Antigen 1 Mimics Epstein-Barr Virus EBNA1 Immune Evasion through Central Repeat Domain Effects on Protein Processing. J. Virol. 81, 8225-8235) to examine protein turnover. A destabilized EGFP was also amplified by PCR using primers (pd1EGFP-sense, GGA TCC GCC ACC ATG GTG AGC AAG GGC GAG GAG CTG (SEQ ID NO: 10); pd1EGFP-antisense, GAA TTC CAC ATT GAT CCT AGC AGA AGC ACA (SEQ ID NO: 11)) and inserted into BamHI/EcoRI sites in the N-terminus of LANA1 constructs (FIG. 5). For flow cytometry studies of antigen presentation, LANA1 full length or deletion mutants of CR region generated with various PCR reactions using primers (Kwun, H. J., et al., 2007 J. Virol. 81, 8225-8235) inserted into EcoRI/HindIII sites. The EGFP$_{OVA}$ expression construct, enhanced GFP (EGFP) was amplified from the pEGFP-C1 vector (Clontech) by PCR and inserted into BamHI/EcoRI sites (Id.). The chicken ovalabumin epitope SIINFEKL (SEQ ID NO: 3) peptide sequence was introduced into HindIII/XhoI sites using direct ligation of following primers: SIIN-Forward 5'-AAG CTT AGC ATA ATT AAT TTC GAA AAG CTC TAA GCG GCC GCG CTC GAG-3' (SEQ ID NO: 4); SIIN-Reverse 5'-CTC GAG CGC GGC CGC TTA GAG CTT TTC GAA ATT AAT TAT GCT AAG CTT-3' (SEQ ID NO: 5). For SP constructs, N-terminal ER signal peptide sequence was introduced in front of EGFP using following primers: SP-sense 5'-GGA TCC GCC ACC ATG AGG TAC ATG ATT TTA GGC TTG CTC GCC CTT GCG GCA GTC TGC AGC GCT ATG GTG AGC AAG GGC GAG GAG (SEQ ID NO: 6); EGFP-antisense 5'-CTT GAA TTC CTT GTA CAG CTC GTC CAT GC-3' (SEQ ID NO: 7). Correct insert sequences were determined by DNA sequencing for all plasmids.

In Vitro Transcription/Translation and Immunoblotting

LANA1 constructs (FIG. 7A) were digested and linearized with XhoI enzyme. DNA templates were in vitro transcribed using T3 RNA polymerase and Riboprobe in vitro transcription system (Promega). RNA concentrations were determined by UV spectroscopic measurement (NanoVue, GE Healthcare) at 260 nm, and 0.5 molar equivalents of RNA were calculated for use in uncoupled in vitro translation with a rabbit reticulocyte lysate system (Promega) and [$^{35}$S]-methionine (GE Healthcare). Reaction products were resolved on SDS-PAGE gel, dried, exposed overnight to screens, and read using a Typhoon imager (GE Healthcare). All the expression levels for LANA1 construct were also confirmed by immunoblotting with anti-GFP (Santa Cruz) or anti-alpha-tubulin (Sigma).

Analysis of GFP Fluorescence (Protein Turnover)

HEK293 cells were grown in Dulbeccos' Modified Eagle Medium (DMEM) supplemented with 10% FBS and transfected with Lipofectamine-2000 (Invitrogen), with either d1EGFP or LANA-d1EGFP constructs (FIG. 6). To examine inhibition of GFP turnover, pd1EGFP-N1 (Kwun, H. J., et al., 2007 J. Virol. 81, 8225-8235) encoding a destabilized EGFP with an estimated half-life ($t_{1/2}$) of 1 h was used for constructing fusions to CR subdomains or LANA full-length/deletion mutant constructs at the N-terminus of EGFP. Twenty-four hours after transfection, cells placed in DMEM with 100 μg/ml CHX (Sigma) to inhibit new protein synthesis or in an equal volume of DMSO diluent as control. Samples were harvested 12 h after CHX or control treatment and lysed in buffer (50 mM Tris-HCl [pH 8.0], 150 mM NaCl, 0.1% SDS, 3 mM EDTA, 1% Triton X-100, 1 mM NaF, and 1 mM Na orthovanadate) supplemented with proteinase inhibitors. Fluorescent protein determination was measured using 50 μg of protein in 100 μl of PBS using a Synergy 2 microplate reader (BioTek).

Flow Cytometry Analysis for Antigen Presentation

HEK293 cells stably expressing the mouse class I allele H-2K$^b$ (referred to as 293KbC2 kindly provided from Dr. Yewdell (Tscharke, D. C., et al. 2005. Identification of poxvirus CD8+ T cell determinants to enable rational design and characterization of smallpox vaccines. J. Exp. Med. 201, 95-104) were grown in DMEM with 10% FBS supplemented with 0.5 mg/ml G418 (Hyclone). For flow cytometry analysis, 293KbC2 cells were transfected with 1 μg of EGFP-LANA1$_{OVA}$ constructs (FIG. 8) or SP-EGFP-LANA1$_{OVA}$ constructs (FIG. 9) using Fugene 6 (Roche) and harvested and washed with PBS 24 hrs after transfection and stained with allophycocyanin (APC) or phycoerytherin (PE) anti-mouse MHC class I Kb-SIINFEKL (25-D1.16 (SEQ ID NO: 3)) (eBioscience) for 30 min at 4 degrees C. Cells were washed twice with PBS and analyzed using a DAKO CyAn high speed analyzer. For each experiment, gating was performed for positive EGFP fluorescence, and 25,000 events were collected and analyzed. The cells were treated with rapamycin (Sigma, 50 nM for 12 h) or chloroquine (Sigma, 100 μM for 12 h) or MG132 (Sigma, 20 μM for 12 h) or interferon gamma (eBioscience, 1000 U/mL for 24 h) before harvest. All experiments were repeated at least three times for reproducibility, with representative experiments shown.

Fluorescence Microscopy

For ER labeling, the cells were incubated at 37° C. for 30 min with ER-Tracker Red (Molecular Probes) and processed by manufacturer's method. Cells were analyzed using Nikon TS100 with Spot insight digital camera or an Olympus AX70 epifluorescence microscope equipped with a Spot RT digital camera.

Statistic Analysis.

Data were compared by analysis of variance with paired student's t-test using Prism software (GraphPad). Values were considered significant at $p<0.05$.

Results

To identify subregions responsible for self-inhibition of LANA1 protein degradation, we generated LANA1 deletion constructs of CR domains (LANAΔCR123) and each CR subdomain (LANAΔCR1, LANAΔCR2, LANAΔCR3) in the context of full-length LANA1 (Kwun, H. J., et al., 2007 J. Virol. 81, 8225-8235) fused to a PEST-sequence destabilized EGFP (d1EGFP) protein (Clontech) cloned into the C-terminus (FIG. 6A) or N-terminus (FIG. 5) and assessed protein turnover rates by fluorescence. LANA1 full-length and deletion mutant constructs were transfected into 293 cells and allowed to recover for 24 hours. Cells were then treated with 100 μg/ml cycloheximide (CHX) for 12 hours to inhibit new protein synthesis and residual EGFP-tagged protein was determined by fluorimetry.

As seen in FIG. 6A, full-length LANA1 protein markedly stabilizes the turnover of PEST-EGFP sequences: 67.5% of LANA1-d1EGFP protein remains 12 hours after CHX inhibition of new protein synthesis while nearly all unfused vector (d1EGFP) protein has undergone degradation during the same period. To exclude the possible effect of the position of GFP tag artificially affecting on the stabilization of the fusion proteins, both C- (FIG. 6A) and N-terminally (FIG. 5) fused PEST-EGFP construct was examined and show similar patterns. When each repeat domain is expressed as a PEST-EGFP expression construct individually or in combination with other repeat domains, only LANA1 CR2-containing peptides have significantly diminished protein turnover (FIG. 6B). Taken together, this data suggests that CR2 primarily inhibits cis protein turnover in the context of the larger LANA1 structure and the primary structure of CR2 alone is sufficient to retard proteasomal degradation.

To determine if, like EBNA1, LANA1 domains retarding cis LANA1 translation also inhibit proteasomal degradation, we examined a CR2-EcoRV-CR3 fragment containing an inserted EcoRV DNA sequence that disrupts the junction between the CR2 and CR3 domains. We previously found that this insertion diminishes LANA1 CR translation retardation mediated by the CR2 CR3 junction (Kwun et al., 2007). Turnover of CR2-EcoRV-CR3, however, is unchanged from the parental fragment having an intact CR2-CR3 junction suggesting that this region is not active in preventing protein turnover. Unlike EBNA1, the translation retardation for KSHV LANA1 (CR2-CR3 junction) can be physically separated from its proteasomal inhibition function (CR2 domain).

We took advantage of the ability to dissociate these two processing functions to determine their importance in MHC class I presentation. LANA1 full-length and deletion constructs were fused with EGFP in the N-terminus and the ovalbumin (Ova) peptide SIINFEKL (SEQ ID NO: 3) in the C-terminus (FIG. 7A). Surface presentation of SIINFEKL (SEQ ID NO: 3) by the murine MHC I allele H2K$^b$ can be detected with flow cytometry using the 25-D1.16 antibody (eBioscience) directed against the peptide bound in the H2K$^b$ cleft (Porgador et al., 1997). We expressed each construct in human 293KbC2 cells engineered for stable expression of murine H2K$^b$ Tscharke, D. C., et al. 2005 J. Exp. Med. 201, 95-104. Expression of each deletion construct was confirmed by immunoblotting (FIG. 7B), in vitro translation (FIG. 7C) and fluorescence microscopy (FIG. 7D).

As expected, construct with deleted CR2 or CR3 domain deletions have higher translation efficiency compared to full-length LANA1 since this disrupts the CR2-CR3 junction (FIG. 7C). Further, expression of the CR1 deletion construct has similar translation efficiency as full-length LANA1, consistent with the site of translation retardation lying between CR2 and CR3. These proteins accumulate in the nucleus similar to parental LANA1 due to retention of nuclear localization signals present in the N and C-termini of LANA1 (FIG. 7D).

Two color flow cytometry for allophycocyanin (APC)-conjugated 25-D1.16 antibody (eBioscience) and EGFP were used to measure SIINFEKL (SEQ ID NO: 3) surface expression in cells expressing the various LANA1 deletion constructs. EGFP vector and EGFP$_{OVA}$ constructs were used as negative and positive controls, respectively. Consistent with the results of Zaldumbide et al. (2007, Mol. Immunol. 44, 1352-1360), the LANA1-SIINFEKL (SEQ ID NO: 3) fusion protein shows marked reduction of SIINFEKL (SEQ ID NO: 3) presentation compared to the EGFP$_{OVA}$ control. We also confirm that LANA1 inhibition of antigen presentation is dependent on the central repeat region since the fusion protein lacking this region (LANAΔCR123$_{OVA}$) is presented at levels similar to the EGFP$_{OVA}$ control protein (FIGS. 8A and 8B). Surprisingly, we find that neither the CR2-CR3 junction, which impedes LANA1 translation (FIG. 7C), nor the CR2 domain, which inhibits proteasomal processing (FIGS. 6A and B) are predominantly responsible for SIINFEKL (SEQ ID NO: 3) immune evasion (FIGS. 8A and 8B). Instead, all LANA1 constructs lacking CR1, including deletion of CR1 alone (LANAΔCR1$_{OVA}$), deletion of the entire CR region (LANAΔCR123$_{OVA}$) and deletion of CR1 CR2 (LANAΔCR12$_{OVA}$), show markedly increased SIINFEKL (SEQ ID NO: 3) peptide presentation compared to LANA$_{OVA}$. In contrast, LANA1 proteins with the CR2 region deleted (LANAΔCR2$_{OVA}$ and LANAΔCR23$_{OVA}$) inhibit MHC I peptide presentation similar to the parental LANA1 molecule. Transfection efficiency for each of the constructs was relatively similar (FIG. 7D), and as monitored through the expression of EGFP protein by flow cytometry analysis (50 to 60% of 25,000 cells were positive for EGFP expression, R1, FIG. 8A) regardless of translation efficiency (FIG. 7C). The amount of total MHC class I level on the surface determined by flow cytometry analysis using anti-mouse MHC class I (H-2Kb) (clone AF6-88.5.5.3, eBioscience) was unchanged with LANA1 expression (data not shown) indicating that inhibition of SIINFEKL (SEQ ID NO: 3) peptide presentation is not due to a general downregulation of MHC I surface expression by LANA1. In addition, co-transfection of CR1 and EGFP$_{OVA}$ from separate plasmids does not inhibit SIINFEKL (SEQ ID NO: 3) presentation (data not shown), indicating that CR1 acts in cis to prevent MHC presentation of SIINFEKL (SEQ ID NO: 3) rather than in trans. Since surface expression level of MHC I is not changed by LANA1, it is unlikely that total MHC I is targeted for trans downregulation as occurs with the KSHV K3 and K5 proteins (Coscoy, L., 2007 Immune evasion by Kaposi's sarcoma-associated herpesvirus. Nat. Rev. Immunol. 7, 391-401).

We next examined whether LANA1 antigen is processed with proteasomal-dependent or -independent fashion (e.g., autophagy) using pretreatment with MG132, rapamycin or chloroquine on 293KbC2 cells transfected with various LANA1$_{OVA}$ constructs (FIG. 8C). Autophagy is one mechanism that might be involved in endogenous LANA1 antigen cross-presentation by MHC class I, as has been described for HSV-1 antigens (English, L., et al., 2009. Autophagy enhances the presentation of endogenous viral antigens on MHC class I molecules during HSV-1 infection. Nat Immunol 10, 480-487). As seen in FIG. 8C, there is no difference in the inhibition of antigen presentation with an autophagy inducer (rapamycin) or inhibitor (chloroquine). In contrast, presentation is largely abolished by MG132 pretreatment, indicating that LANA1 is processed for MHC I presentation through canonical proteasomal processing. To determine if immunoproteasomal processing is critical to LANA1 presentation, we pretreated with interferon gamma (FIG. 8C). Relatively higher antigen presentation of LANA1 suggests that immunoproteasomal processing enhances LANA1 presentation.

That LANA1 CR1 inhibits presentation in cis but does not either retard synthesis of LANA1 or its proteasomal degradation suggests that it might reduce translocation of LANA1 peptides from the cytosol into the ER for loading onto MHC I. We therefore bypassed this step by introducing endoplasmic reticulum (ER) signal peptide (SP) sequences (Persson, H., et al. 1980. Multiple mRNA species for the precursor to an adenovirus-encoded glycoprotein: identification and structure of the signal sequence. Proc Natl Acad Sci USA 77, 6349-6353) into the N-terminal of EGFP-LANA1$_{OVA}$ constructs (SP-LANA$_{OVA}$, SP-LANADΔCR1$_{OVA}$) and examined expression and antigen presentation. SP constructs expressing cells (green) were also loaded with ER-tracker (red), a marker for the ER, to determine the localization of LANA1 (FIG. 9A). In contrast to LANA$_{OVA}$ without SP, SP-LANA$_{OVA}$ is efficiently processed for MHC I presentation (FIG. 9B). Both LANADΔCR1$_{OVA}$ proteins, with or without the SP, undergo similar levels of antigen presentation suggesting that CR1 inhibits pre-ER steps in peptide presentation (FIG. 9B). Pretreatment of SP-LANA$_{OVA}$ with MG132 diminished peptide presentation and so we cannot exclude that this protein undergoes retro-translocation and proteasomal degradation.

Discussion

Cytotoxic T lymphocyte (CTL) recognition of infected host cells is critical to immune control of KSHV infection. The response is initiated when intracellular viral proteins are degraded by the proteasomal machinery, allowing short peptide sequences to be processed and presented on the infected cell surface bound to major histocompatibility class I (MHC I) antigens. Using ova-fusion constructs, we examined LANA1 cis-inhibition of antigen presentation. While our studies provide general insights into LANA1 antigen presentation, caution is needed in interpreting them and our results require confirmation under more natural settings.

To understand the mechanisms of LANA1 CTL immune evasion, we previously examined LANA1's translational retardation and turnover inhibition properties (Kwun, H. J., et al., 2007 J. Virol. 81, 8225-8235). We found that a LANA1 peptide sequence at the junction of the CR2 and CR3 subdomains was required to retard translation of LANA1 mRNA, an effect similar to the EBNA1 GAr. We also found that LANA1 proteins containing the entire CR domain inhibit proteasomal turnover as has been previously described. Although these findings could suggest the possibility for common mechanisms to evade MHC I presentation for latent viral protein peptides by the large DNA tumor viruses, this is not always the case as the herpesvirus saimiri (HVS) reduces mRNA levels of the open reading frame (ORF73) protein homologous to KSHV LANA1 to avoid MHC class I antigen presentation. Careful analysis of the individual LANA1 CR domains also indicates that KSHV and EBV use different mechanisms to evade CTL immune responses against their major latency proteins.

Here we show that the LANA1 CR1 domain is primarily responsible for in cis prevention of MHC I presentation of LANA1 peptides. Unlike EBV EBNA1, this effect can be physically separated from translation retardation and proteasome inhibition domains, suggesting that neither is critical for LANA1 evasion of antigen presentation. Surprisingly, CR1's immune evasion mechanism appears to be more complex than simple inhibition of proteasomal processing. The CR2 domain expressed as an isolated fragment markedly retards cis proteasomal processing yet its contribution to inhibition of MHC I peptide presentation is minimal compared to CR1.

Since MHC I presentation inhibition occurs in cis and yet proteasomal processing is not markedly inhibited by CR1, one possibility is that CR1 domain decouples proteasomes processing LANA1 from the ER translocation machinery Immunoproteasomal processing is tightly linked to cytosolic surface of the ER membrane so that peptides generated by processing are efficiently translocated by transporter associated with antigen presentation 1 (TAP1). Herpes simplex virus ICP47 binds to TAP1 and blocks transport of viral peptides into the ER. Cytomegalovirus also blocks peptide transport by producing a protein, US6, which blocks TAP1. When we bypass this machinery using a signal peptide to directly translocate LANA1 into the ER, both LANA1 and LANA1 lacking a CR1 domain are efficiently presented to MHC I (LANA1 expressed into the lumen of the ER might be processed by ER aminopeptidase associated with antigen processing (ERAAP) or by retrotranslocation and proteasomal processing of LANA1 protein). This raises the possibility that CR1 delocalizes the active immunoproteasome from the TAP machinery so that peptides generated in cis are not efficiently translocated into the ER. LANA1 does not affect expression of TAP1 or immunoproteasome components LMP2 or LMP7 (data not shown), consistent with CR1 not disrupting the processing and translocation machinery itself. Despite their functional similarities, EBV EBNA1 and KSHV LANA1 avoid CTL recognition through different mechanisms and LANA1 serves as a unique model for interrogating this system.

KSHV proteins have been shown to possess a remarkable array of immune evasion activities. Understanding how KSHV avoids effective immune responses during latency is critical for effective vaccines to prevent and treat tumors caused by this virus. Our findings suggest that a LANA1 therapeutic vaccine candidate lacking the CR1 domain may be more effective than the parental molecule in inducing a functional CTL response against virus infected cells. Regardless of whether or not CR1 deletion candidates ultimately are useful for therapeutic vaccines, there is a striking need for KSHV vaccine candidates that can be employed in sub-Saharan Africa where KSHV is near-ubiquitous and where KS is now one of the most commonly reported tumors.

Example 2

Ex Vivo Vaccination Using Recombinant Virus Particles

Genes encoding LANA1 CR1 deletion mutants are prepared by insertion of an open-reading frame encoding a LANA1 CR1 deletion protein as described in Example 1 into a multiple-cloning site of pAAV-MCS (Cell Biolabs, Inc, San Diego Calif.). Plasmid structure is verified by sequencing. pAAV-MCS having the deltaCR1 LANA1 sequence is cotransfected into 293AAV cells with pAAV-RC and pHelper according to Cell Biolabs AAV-1 Helper Free Expression System Product Manual. Transducing particles are titered.

Dendritic cells are isolated from a patient according to standard protocol and are maintained in culture according to standard protocol. The dendritic cells are transduced with the transducing particles at a multiplicity of infection ranging from 1:1 to 1:10$^6$ ratios of dendritic cells to transducing particles. Expression of deltaCR1-LANA1 polypeptide is confirmed by immunohistochemistry performed on a portion of the transduced dendritic cells. The transduced dendritic cells are then transferred back into the patient thereby eliciting an immune response to LANA1.

Example 3

Vaccination Using deltaCR1-LANA1 Polypeptide

DeltaCR1-LANA1 polypeptide, for example as described in Example 1, is prepared by gene expression in yeast by subcloning of the deltaCR1-LANA1 open-reading frame into pPinka-HC plasmid (PichiaPink™ Yeast Expression System, Invitrogen, Carlsbad, Calif.). deltaCR1-LANA1 protein was prepared according to the PichiaPink™ Yeast Expression System User Manual (Aug. 6, 2010). Recombinant deltaCR1-LANA1 protein is purified by precipitation and/or chromatographic methods and is combined into a vaccine with a suitable adjuvant. Unit doses of the vaccine range from 0.1 to 2 mL and comprise protein ranging from 0.01 ng to 1 mg per unit dose and include a suitable adjuvant, such as aluminum phosphate or aluminum hydroxide. Vaccine is administered intramuscularly or subcutaneously in one or more unit doses.

Whereas, particular embodiments of the invention have been described above for purposes of description, it will be appreciated by those skilled in the art that numerous variations of the details may be made without departing from the invention as described in the appended claims.

We claim:

1. A nucleic acid encoding a Kaposi sarcoma associated herpes virus latency associated nuclear antigen amino acid sequence ("KSHV LANA1") having the amino acid sequence of SEQ ID NO: 1, wherein the amino acid sequence is modified by the deletion of from 20 to 98 amino acids between amino acids 330 and 428.

2. The nucleic acid according to claim 1, wherein the deletion of 20 to 98 amino acids of SEQ ID NO: 1 includes the deletion of one or more amino acid motifs selected from the group consisting of SEQ ID NO: 8 and SEQ ID NO: 9.

3. The nucleic acid according to claim 1, wherein the deletion of 20 to 98 amino acids of SEQ ID NO: 1 includes the removal of at least one aspartic acid or glutamic acid residue between amino acids 330 and 428 of SEQ ID NO: 1.

4. A nucleic acid encoding a Kaposi sarcoma associated herpes virus latency associated nuclear antigen amino acid sequence ("KSHV LANA1") and having the amino acid sequence of SEQ ID NO: 1 and a protein destabilization domain, wherein the amino acid sequence is modified by removing or replacing at least one amino acid between amino acid 330 and amino acid 428 of SEQ ID NO: 1.

5. The nucleic acid according to claim 4, wherein the protein destabilization domain is one of a D-Box, KEN, PEST, Cyclin A, and a ubiquitin fusion degradation (UFD) domain/substrate.

6. A method of eliciting an immune response to Kaposi sarcoma associated herpes virus latency associated nuclear antigen ("KSHV LANA1") in a patient comprising introducing into the patient a nucleic acid encoding a Kaposi sarcoma associated herpes virus latency associated nuclear antigen amino acid sequence ("KSHV LANA1") having the amino acid sequence of SEQ ID NO: 1, wherein the amino acid sequence is modified such that 20 to 98 amino acids between amino acids 330 and 428 are deleted.

7. The method according to claim 6, wherein the deletion of 20 to 98 amino acids of SEQ ID NO: 1 includes the deletion of one or more amino acid motifs selected from the group consisting of SEQ ID NO: 8 and SEQ ID NO: 9.

8. The method according to claim 6, wherein the deletion of 20 to 98 amino acids of SEQ ID NO: 1 includes the removal of at least one aspartic acid or glutamic acid residue between amino acids 330 and 428 of SEQ ID NO: 1.

9. The method according to claim 6, wherein the nucleic acid is introduced into the patient in a viral transducing particle.

10. The method according to claim 6, wherein the nucleic acid is introduced into the patient in a liposome.

11. The method according to claim 6, wherein the nucleic acid is introduced into the patient in a composition comprising one or more pharmaceutically-acceptable carriers or adjuvants.

12. The method according to claim 11, wherein the composition comprising the nucleic acid is administered to the patient parenterally.

13. The method according to claim 11, wherein the composition comprising the nucleic acid is introduced into the patient via an intramuscular injection.

14. The method according to claim 6, wherein SEQ ID NO: 1 is modified by a deletion of amino acids 330-428.

* * * * *